(12) United States Patent
Olson et al.

(10) Patent No.: US 6,730,690 B2
(45) Date of Patent: May 4, 2004

(54) 11-β-HYDROXYSTEROID DEHYDROGENASE 1 INHIBITORS USEFUL FOR THE TREATMENT OF DIABETES, OBESITY AND DYSLIPIDEMIA

(75) Inventors: Steven H. Olson, Metuchen, NJ (US); James M. Balkovec, Martinsville, NJ (US); Yuping Zhu, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/457,682

(22) Filed: Jun. 9, 2003

(65) Prior Publication Data

US 2004/0048912 A1 Mar. 11, 2004

Related U.S. Application Data

(60) Provisional application No. 60/387,385, filed on Jun. 10, 2002.

(51) Int. Cl.[7] .................. A61K 31/4196; A61P 3/06; C07D 249/08
(52) U.S. Cl. .................. 514/383; 548/262.2; 548/269.4
(58) Field of Search .................. 548/262.2, 269.4; 514/383

(56) References Cited

FOREIGN PATENT DOCUMENTS

| WO | WO 99/29674 | 6/1999 |
|---|---|---|
| WO | WO 00/07997 | 2/2000 |
| WO | WO 01/60802 | 8/2001 |
| WO | WO 03/004497 | 1/2003 |

*Primary Examiner*—Robert W. Ramsuer
(74) *Attorney, Agent, or Firm*—Philippe L. Durette; Melvin Winokur

(57) ABSTRACT

Compounds having Formula I, including pharmaceutically acceptable salts, hydrates and solvates thereof:

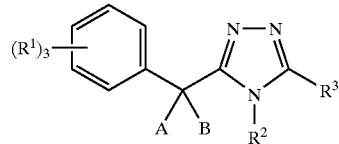

are selective inhibitors of the 11β-HSD1 enzyme. The compounds are useful for the treatment of diabetes, such as noninsulin-dependent diabetes (NIDDM), hyperglycemia, obesity, insulin resistance, dylsipidemia, hyperlipidemia, hypertension, Syndrome X, and other symptoms associated with NIDDM.

42 Claims, No Drawings

11-β-HYDROXYSTEROID DEHYDROGENASE 1 INHIBITORS USEFUL FOR THE TREATMENT OF DIABETES, OBESITY AND DYSLIPIDEMIA

CROSS-REFERENCE TO RELATED APPLICATIONS

The present invention is related to U.S. provisional application Ser. No. 60/387,385, filed Jun. 10, 2002, the contents of which are hereby incorporated by reference.

FIELD OF THE INVENTION

The present invention relates to inhibitors of the enzyme 11-beta-hydroxysteroid dehydrogenase Type I (11β-HSD-1 or HSD-1), and methods of treatment using such compounds. The compounds are useful for the treatment of diabetes, such as non-insulin dependent type 2 diabetes mellitus (NIDDM), insulin resistance, obesity, lipid disorders and other diseases and conditions.

BACKGROUND OF THE INVENTION

Diabetes is caused by multiple factors and is most simply characterized by elevated levels of plasma glucose (hyperglycemia) in the fasting state. There are two generally recognized forms of diabetes: type 1 diabetes, or insulin-dependent diabetes mellitus (IDDM), in which patients produce little or no insulin, the hormone which regulates glucose utilization, and type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver.

Persistent or uncontrolled hyperglycemia that occurs in diabetics is associated with increased morbidity and premature and mortality. Abnormal glucose homeostasis is also associated both directly and indirectly with obesity, hypertension and alterations in lipid, lipoprotein and apolipoprotein metabolism. Type 2 diabetics are at increased risk of cardiovascular complications, e.g., atherosclerosis, coronary heart disease, stroke, peripheral vascular disease, hypertension, nephropathy, neuropathy and retinopathy. Therefore, therapeutic control of glucose homeostasis, lipid metabolism, obesity and hypertension are critically important in the clinical management and treatment of diabetes mellitus.

Many patients who have insulin resistance but have not developed type 2 diabetes are also at a risk of developing symptoms referred to as "Syndrome X", or the "metabolic syndrome". Syndrome X is characterized by insulin resistance, along with abdominal obesity, hyperinsulinemia, high blood pressure, low HDL and high VLDL. These patients, whether or not they develop overt diabetes mellitus, are at increased risk of developing the cardiovascular complications listed above.

Treatment of type 2 diabetes typically includes physical exercise and dieting. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate insulin-resistant tissues. However, dangerously low levels of plasma glucose can result, and an increased level of insulin resistance can ultimately occur.

Biguanides increase insulin sensitivity, resulting in some correction of hyperglycemia. However, many biguanides, e.g., phenformin and metformin, cause lactic acidosis, nausea and diarrhea.

The glitazones (i.e. 5-benzylthiazolidine-2,4-diones) form a newer class of compounds with the potential for ameliorating hyperglycemia and other symptoms of type 2 diabetes. These agents substantially increase insulin sensitivity in muscle, liver and adipose tissue, resulting in partial or complete correction of the elevated plasma levels of glucose substantially without causing hypoglycemia. The glitazones that are currently marketed are agonists of the peroxisome proliferator activated receptor (PPAR) gamma subtype. PPAR-gamma agonism is generally believed to be responsible for the improved insulin sensitization that is observed with the glitazones. Newer PPAR agonists that are being developed for treatment of Type 2 diabetes and/or dyslipidemia are agonists of one or more of the PPAR alpha, gamma and delta subtypes.

There is a continuing need for new methods of treating diabetes and related conditions. The present invention meets this and other needs.

SUMMARY OF THE INVENTION

The present invention relates to a compound represented by Formula I:

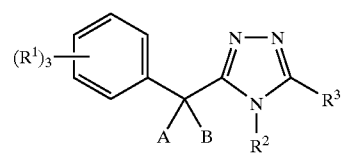

or a pharmaceutically acceptable salt or solvate thereof, wherein:

A and B may be taken separately or together;
when taken separately,
A represents halo, $C_{1-6}$alkyl, $OC_{1-6}$alkyl or phenyl, said alkyl, phenyl and the alkyl portion of $OC_{1-6}$alkyl being optionally substituted with 1–3 halo groups; and
B represents represents H, halo, $C_{1-6}$alkyl, $—OC_{1-6}$alkyl, $—SC_{1-6}$alkyl, $C_{2-6}$alkenyl, phenyl or naphthyl, said alkyl, alkenyl, phenyl, naphthyl, and the alkyl portions of $—OC_{1-6}$alkyl and $—SC_{1-6}$alkyl being optionally substituted with 1–3 groups selected from halo, OH, $CH_3O$, $CF_3$ and $OCF_3$; and
when taken together, A and B together represents (a) $A_{1-4}$alkylene optionally substituted with 1–3 halo groups, and 1–2 $R^a$ groups wherein $R^a$ represents $C_{1-3}$alkyl, $OC_{1-3}$alkyl, $C_{6-10}arC_{1-6}$alkylene or phenyl optionally substituted with 1–3 halo groups, or (b) $C_{2-5}$alkanediyl such that they form a 3–6 membered ring with the carbon atom to which they are attached, said ring optionally containing 1 double bond or 1–2 heteroatoms selected from O, S and N, said 3–6 membered ring being optionally substituted with $C_{1-4}$alkylene, oxo, ethylenedioxy or propylenedioxy, and being further optionally substituted with 1–4 groups selected from halo, $C_{1-4}$alkyl, halo$C_{1-4}$alkyl, $C_{1-3}$acyl, $C_{1-3}$acyloxy, $C_{1-3}$alkoxy, $C_{1-6}$alkylOC(O)—, $C_{2-4}$alkenyl, $C_{2-4}$alkynyl, $C_{1-3}$alkoxy$C_{1-3}$alkyl, $C_{1-3}$alkoxy$C_{1-3}$alkoxy, phenyl, CN, OH, D, $NH_2$, $NHR^a$ and $N(R^a)_2$ wherein $R^a$ is as previously defined;

each $R^1$ represents H or is independently selected from the group consisting of: OH, halo, $C_{1-10}$alkyl, $C_{1-6}$alkoxy and $C_{6-10}$aryl, said $C_{1-10}$alkyl, $C_{6-10}$aryl and the alkyl portion of $C_{1-6}$alkoxy being optionally substituted with 1–3 halo, OH, $OC_{1-3}$alkyl, phenyl or naphthyl groups, said phenyl and naphthyl being optionally substituted with 1–3 substituents independently selected from halo, $OCH_3$, $OCF_3$, $CH_3$, $CF_3$ and phenyl, wherein said phenyl is optionally substituted with 1–3 halo groups, or two $R^1$ groups taken together represent a fused $C_{5-6}$alkyl or aryl ring, which may be optionally substituted with 1–2 OH or $R^a$ groups, wherein $R^a$ is as defined above;

$R^2$ and $R^3$ are taken together or separately;

when taken together, $R^2$ and $R^3$ represent (a) a $C_{3-8}$ alkanediyl forming a fused 5–10 membered non-aromatic ring optionally interrupted with 1–2 double bonds, and optionally interrupted by 1–2 heteroatoms selected from O, S and N; or (b) a fused 6–10 membered aromatic monocyclic or bicyclic group, said alkanediyl and aromatic monocyclic or bicyclic group being optionally substituted with 1–6 halo atoms, and 1–4 of OH, $C_{1-3}$alkyl, $OC_{1-3}$alkyl, halo$C_{1-3}$alkyl, halo$C_{1-3}$alkoxy, and phenyl, said phenyl being optionally substituted with 1–4 groups independently selected from halo, $C_{1-3}$alkyl, $OC_{1-3}$alkyl, and said $C_{1-3}$alkyl and the $C_{1-3}$alkyl portion of $OC_{1-3}$alkyl being optionally substituted with 1–3 halo groups;

when taken separately, $R^2$ is selected from the group consisting of: (a) $C_{1-14}$alkyl optionally substituted with 1–6 halo groups and 1–3 substituents selected from OH, $OC_{1-3}$alkyl, and phenyl, said phenyl being optionally substituted with 1–4 groups independently selected from halo, $OCH_3$, $OCF_3$, $CH_3$ and $CF_3$, and said $C_{1-3}$alkyl portion of $OC_{1-3}$alkyl being optionally substituted with 1–3 halo groups; (b) phenyl or pyridyl optionally substituted with 1–3 halo, OH or $R^a$ groups, with $R^a$ as previously defined; (c) $C_{2-10}$ alkenyl, optionally substituted with 1–3 substituents independently selected from halo, OH and $OC_{1-3}$alkyl, said $C_{1-3}$alkyl portion of $OC_{1-3}$alkyl being optionally substituted with 1–3 halo groups; (d) $CH_2CO_2H$; (e) $CH_2CO_2C_{1-6}$alkyl; (f) $CH_2C(O)NHR^a$ wherein $R^a$ is as previously defined; (g) $NH_2$, $NHR^a$ and $N(R^a)_2$ wherein $R^a$ is as previously defined;

and $R^3$ is selected from the group consisting of: $C_{1-14}$alkyl, $C_{2-10}$alkenyl, $SC_{1-6}$alkyl, $C_{6-10}$aryl, heterocyclyl and heteroaryl, said alkyl, alkenyl, aryl, heterocyclyl, heteroaryl and the alkyl portion of $SC_{1-6}$alkyl being optionally substituted with (a) R; (b) 1–6 halo groups and (c) 1–3 groups selected from OH, $NH_2$, $NHC_{1-4}$alkyl, $N(C_{1-4}$alkyl$)_2$, $C_{1-4}$alkyl, $OC_{1-4}$alkyl, CN, $C_{1-4}$alkylS(O)$_x$— wherein x is 0, 1 or 2, $C_{1-4}$alkylSO$_2$NH—, $H_2NSO_2$—, $C_{1-4}$alkylNHSO$_2$— and $(C_{1-4}$alkyl$)_2$NSO$_2$—, said $C_{1-4}$alkyl and the $C_{1-4}$alkyl portions of said groups being optionally substituted with phenyl and 1–3 halo groups, and R is selected from heterocyclyl, heteroaryl and aryl, said group being optionally substituted with 1–4 groups selected from halo, $C_{1-4}$alkyl, $C_{1-4}$alkylS(O)$_x$—, with x as previously defined, $C_{1-4}$ alkylSO$_2$NH—, $H_2NSO_2$—, $C_{1-4}$alkylNHSO$_2$—, $(C_{1-4}$ alkyl$)_2$NSO$_2$—, CN, OH, $OC_{1-4}$alkyl, and, said $C_{1-4}$alkyl and the $C_{1-4}$alkyl portions of said groups being optionally substituted with 1–5 halo and 1 group selected from OH and $OC_{1-3}$alkyl.

DETAILED DESCRIPTION OF THE INVENTION

The present invention relates to a compound represented by Formula I:

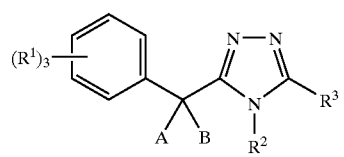

or a pharmaceutically acceptable salt or solvate thereof, wherein:

A and B may be taken separately or together;

when taken separately,

A represents halo, $C_{1-6}$alkyl, $OC_{1-6}$alkyl or phenyl, said alkyl, phenyl and the alkyl portion of $OC_{1-6}$alkyl being optionally substituted with 1–3 halo groups; and B represents represents H, halo, $C_{1-6}$alkyl, —$OC_{1-6}$alkyl, —$SC_{1-6}$alkyl, $C_{2-6}$alkenyl, phenyl or naphthyl, said alkyl, alkenyl, phenyl, naphthyl, and the alkyl portions of —$OC_{1-6}$alkyl and —$SC_{1-6}$alkyl being optionally substituted with 1–3 groups selected from halo, OH, $CH_3O$, $CF_3$ and $OCF_3$; and when taken together, A and B together represents (a) $C_{1-4}$alkylene optionally substituted with 1–3 halo groups, and 1–2 $R^a$ groups wherein $R^a$ represents $C_{1-3}$alkyl, $OC_{1-3}$alkyl, $C_{6-10}arC_{1-6}$alkylene or phenyl optionally substituted with 1–3 halo groups, or (b) $C_{2-5}$alkanediyl such that a 3–6 membered ring is formed with the carbon atom to which they are attached, said ring being optionally interrupted with 1 double bond or 1–2 heteroatoms selected from O, S and N, said 3–6 membered ring being optionally substituted with $C_{1-4}$alkylene, oxo, ethylenedioxy or propylenedioxy, and being further optionally substituted with 1–4 groups selected from halo, $C_{1-4}$alkyl, halo$C_{1-4}$alkyl, $C_{1-3}$acyl, $C_{1-3}$acyloxy, $C_{1-3}$alkoxy, $C_{1-6}$alkylOC(O)—, $C_{2-4}$alkenyl, $C_{2-4}$alkynyl, $C_{1-3}$alkoxy$C_{1-3}$alkyl, $C_{1-3}$alkoxy$C_{1-3}$alkoxy, phenyl, CN, OH, D, $NH_2$, $NHR^a$ and $N(R^a)_2$ wherein $R^a$ is as previously defined;

each $R^1$ represents H or is independently selected from the group consisting of: OH, halo, $C_{1-10}$alkyl, $C_{1-6}$alkoxy and $C_{6-10}$aryl, said $C_{1-10}$alkyl, $C_{6-10}$aryl and the alkyl portion of $C_{1-6}$alkoxy being optionally substituted with 1–3 halo, OH, $OC_{1-3}$alkyl, phenyl or naphthyl groups, said phenyl and naphthyl being optionally substituted with 1–3 substituents independently selected from halo, $OCH_3$, $OCF_3$, $CH_3$, $CF_3$ and phenyl, wherein said phenyl is optionally substituted with 1–3 halo groups, or two $R^3$ groups taken together represent a fused $C_{5-6}$alkyl or aryl ring, which may be optionally substituted with 1–2 OH or $R^a$ groups, wherein $R^a$ is as defined above;

$R^2$ and $R^3$ are taken together or separately;

when taken together, $R^2$ and $R^3$ represent (a) a $C_{3-8}$ alkanediyl forming a fused 5–10 membered non-aromatic ring optionally interrupted with 1–2 double bonds, and optionally interrupted by 1–2 heteroatoms selected from O, S and N; or (b) a fused 6–10 membered aromatic monocyclic or bicyclic group, said alkanediyl and aromatic monocyclic or bicyclic group being optionally substituted with 1–6 halo atoms, and 1–4 of OH, $C_{1-3}$alkyl, $OC_{1-3}$alkyl, halo$C_{1-3}$alkyl, halo$C_{1-3}$alkoxy, and phenyl, said phenyl being optionally substituted with 1–4 groups independently selected from halo, $C_{1-3}$alkyl, $OC_{1-3}$alkyl, and said $C_{1-3}$alkyl and the $C_{1-3}$alkyl portion of $OC_{1-3}$alkyl being optionally substituted with 1–3 halo groups;

when taken separately, $R^2$ is selected from the group consisting of: (a) $C_{1-14}$alkyl optionally substituted with 1–6 halo groups and 1–3 substituents selected from OH, $OC_{1-3}$alkyl, and phenyl, said phenyl being optionally substituted with 1–4 groups independently selected from halo, $OCH_3$, $OCF_3$, $CH_3$ and $CF_3$, and said $C_{1-3}$alkyl portion of $OC_{1-3}$alkyl being optionally substituted with 1–3 halo groups; (b) phenyl or pyridyl optionally substituted with 1–3 halo, OH or $R^a$ groups, with $R^a$ as previously defined; (c) $C_{2-10}$ alkenyl, optionally substituted with 1–3 substituents independently selected from halo, OH and $OC_{1-3}$alkyl, said $C_{1-3}$alkyl portion of $OC_{1-3}$alkyl being optionally substituted with 1–3 halo groups; (d) $CH_2CO_2H$; (e) $CH_2CO_2C_{1-6}$alkyl; (f) $CH_2C(O)NHR^a$ wherein $R^a$ is as previously defined; (g) $NH_2$, $NHR^a$ and $N(R^a)_2$ wherein $R^a$ is as previously defined;

and $R^3$ is selected from the group consisting of: $C_{1-14}$alkyl, $C_{2-10}$alkenyl, $SC_{1-6}$alkyl, $C_{6-10}$aryl, heterocyclyl and heteroaryl, said alkyl, alkenyl, aryl, heterocyclyl, heteroaryl and the alkyl portion of $SC_{1-6}$alkyl being optionally substituted with (a) R; (b) 1–6 halo groups and (c) 1–3 groups selected from OH, $NH_2$, $NHC_{1-4}$alkyl, $N(C_{1-4}$alkyl$)_2$, $C_{1-4}$alkyl, $OC_{1-4}$alkyl, CN, $C_{1-4}$alkylS(O)$_x$— wherein x is 0, 1 or 2, $C_{1-4}$alkylSO$_2$NH—, $H_2NSO_2$—, $C_{1-4}$alkylNHSO$_2$— and $(C_{1-4}$alkyl$)_2$NSO$_2$—, said $C_{1-4}$alkyl and the $C_{1-4}$alkyl portions of said groups being optionally substituted with phenyl and 1–3 halo groups, and R is selected from heterocyclyl, heteroaryl and aryl, said group being optionally substituted with 1–4 groups selected from halo, $C_{1-4}$alkyl, $C_{1-4}$alkylS(O)$_x$—, with x as previously defined, $C_{1-4}$ alkylSO$_2$NH—, $H_2NSO_2$—, $C_{1-4}$alkylNHSO$_2$—, $(C_{1-4}$ alkyl$)_2$NSO$_2$—, CN, OH, $OC_{1-4}$alkyl, and, said $C_{1-4}$alkyl and the $C_{1-4}$alkyl portions of said groups being optionally substituted with 1–5 halo and 1 group selected from OH and $OC_{1-3}$alkyl.

As used herein the following definitions are applicable.

"Ac" is acetyl, which is $CH_3C(O)$—.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_3$–$C_{10}$, the term alkyl also includes cycloalkyl groups, and combinations of linear or branched alkyl chains combined with cycloalkyl structures. When no number of carbon atoms is specified, $C_{1-6}$ is intended.

"Alkenyl" means carbon chains which contain at least one carbon-carbon double bond, and which may be linear or branched or combinations thereof, unless the carbon chain is defined otherwise. Examples of alkenyl include vinyl, allyl, isopropenyl, pentenyl, hexenyl, heptenyl, 1-propenyl, 2-butenyl, 2-methyl-2-butenyl, and the like. Where the specifice number of carbon atoms permits, e.g., from $C_5$–$C_{10}$, the term alkenyl also includes cycloalkenyl groups, and combinations of linear, branched and cyclic structures. When no number of carbon atoms is specified, $C_{2-6}$ is intended "Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Alkanediyl" refers to carbon chains that are bifunctional, such as —$CH_2$—, —$(CH_2)_2$—, —$(CH_2)_3$—, and the like. Alkanediyl groups are linear or branched, unless otherwise indicated. For comparison, alkyl groups are monofunctional.

"Alkylene" as used herein refers to a carbon atom or carbon chain that is attached through a double bond.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, and the like. A cycloalkyl group generally is monocyclic unless stated otherwise. Cycloalkyl groups are saturated unless otherwise defined.

"Aryl" means a mono- or polycyclic aromatic ring system containing carbon ring atoms. The preferred aryls are monocyclic or bicyclic 6–10 membered aromatic ring systems. Phenyl and naphthyl are preferred aryls. The most preferred aryl is phenyl.

"Heterocycle" and "hetercyclyl" refer to saturated or unsaturated non-romatic rings or ring systems containing at least one heteroatom selected from O, S and N, further including the oxidized forms of sulfur, SO and $SO_2$). Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, teterhydropyran, dihydropyran, oxathiolane, dithiolane, 1,3-dioxane, 1,3-dithiane, oxathiane, thiomorpholine and the like.

"Heteroaryl" means an aromatic or partially aromatic heterocycle that contains at least one ring heteroatom selected from O, S and N, (including SO). Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, quinolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl (including S-oxide), quinolyl, indolyl, isoquinolyl, dibenzofuranyl, napthyridyl and the like. For heterocyclyl and heteroaryl groups, rings and ring systems containing from 3–15 atoms are included, forming 1–3 rings.

"Halo" and "Halogen" refer to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term "pharmaceutical composition" encompasses a product comprising the active ingredient(s) and a carrier, as well as any product which results, directly or indirectly, from the combination, complexation or aggregation of any two or more of the ingredients, or from a dissociation or another type of reaction of one or more of the ingredients. Accordingly, the pharmaceutical compositions of the present invention include those made by admixing a compound or compounds of the present invention and a pharmaceutically acceptable carrier.

Compounds of Formula I may contain one or more asymmetric centers and can thus occur as racemates and racemic mixtures, single enantiomers, diastereomeric mixtures and individual diastereomers. All such isomeric forms are included.

Some of the compounds described herein contain olefinic double bonds. Both E and Z geometric isomers are included in pure form as well as in admixture.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are included.

If desired, racemic mixtures of compounds of Formula I may be separated so that individual enantiomers are isolated. The separation can be carried out by methods well known in the art, such as the coupling of a racemic mixture of compounds of Formula I to an enantiomerically pure compound to form a diastereomeric mixture, which is then separated into individual diastereomers by standard methods, such as fractional crystallization or chromatography. The coupling reaction is often the formation of salts using an enantiomerically pure acid or base. The diastereomeric derivatives may then be converted to substantially pure enantiomers by cleaving the added chiral residue from the diastereomeric compound.

The racemic mixture of the compounds of Formula I can also be separated directly by chromatographic methods utilizing chiral stationary phases, which methods are well known in the art.

Alternatively, enantiomers of compounds of the general Formula I may be obtained by stereoselective synthesis using optically pure starting materials or reagents.

One aspect of the invention that is of particular interest relates to a compound of formula I wherein A and B are taken together and represent $C_{2-5}$alkanediyl such that a 3–6 membered ring is formed with the carbon atom to which they are attached, said ring optionally containing 1 double bond or 1–2 heteroatoms selected from O, S and N, said 3–6 membered ring being optionally substituted with $C_{1-4}$alkylene, oxo, ethylenedioxy or propylenedioxy, and being further optionally substituted with 1–4 groups selected from halo, $C_{1-4}$alkyl, halo$C_{1-4}$alkyl, $C_{1-3}$acyl, $C_{1-3}$acyloxy, $C_{1-3}$alkoxy, $C_{1-6}$alkylOC(O)—, $C_{2-4}$alkenyl, $C_{2-4}$alkynyl, $C_{1-3}$alkoxy$C_{1-3}$alkyl, $C_{1-3}$alkoxy$C_{1-3}$alkoxy, phenyl, CN, OH, D, $NH_2$, $NHR^a$ and $N(R^a)_2$ wherein $R^a$ represents $C_{1-3}$alkyl, $OC_{1-3}$alkyl, $C_{6-10}arC_{1-6}$alkylene or phenyl optionally substituted with 1–3 halo groups. Within this aspect of the invention, all other variables are as defined with respect to formula I.

Another aspect of the invention that is of more particular interest is a compound as described above wherein A and B are taken together and represent a $C_{2-4}$ membered alkanediyl group such that a 3 to 5 membered ring is formed with the carbon atom to which they are attached, optionally substituted with 1–2 groups selected from halo, $C_{1-4}$alkyl, halo$C_{1-4}$alkyl, $C_{1-3}$alkoxy, $C_{1-3}$alkoxy$C_{1-3}$alkyl, $C_{1-3}$alkoxy$C_{1-3}$alkoxy and phenyl. Within this aspect of the invention, all other variables are as defined with respect to formula I.

Even more particularly, an aspect of the invention that is of interest relates to a compound as described above wherein A and B are taken together and represent a $C_{2-4}$ alkanediyl group such that a 3–5 membered ring is formed with the carbon atom to which they are attached, said ring being unsubstituted or substituted with 1–2 halo groups. Within this aspect of the invention, all other variables are as defined with respect to formula I.

Even more particularly, an aspect of the invention that is of interest relates to a compound as described above wherein the 1–2 halo groups are fluoro groups. Within this aspect of the invention, all other variables are as defined with respect to formula I.

In another aspect of the invention that is of interest, a compound of formula I is disclosed wherein two $R^1$ groups represent H and one $R^1$ is selected from the group consisting of: OH, halo, $C_{1-10}$alkyl, $C_{1-6}$alkoxy and $C_{6-10}$aryl, said $C_{1-10}$alkyl, $C_{6-10}$aryl and the alkyl portion of $C_{1-6}$alkoxy being optionally substituted with 1–3 halo, OH, $OC_{1-3}$alkyl, phenyl or naphthyl groups, said phenyl and naphthyl being optionally substituted with 1–3 substituents selected from: halo, $OCH_3$, $OCF_3$, $CH_3$, $CF_3$ and phenyl, wherein said phenyl is optionally substituted with 1–3 halo groups. Within this aspect of the invention, all other variables are as defined with respect to formula I.

More particularly, an aspect of the invention that is of interest relates to a compound of formula I wherein one $R^1$ group represents H and two $R^1$ groups are selected from the group consisting of: OH, halo, $C_{1-10}$alkyl and $C_{1-6}$alkoxy, said $C_{1-10}$alkyl and the alkyl portion of $C_{1-6}$alkoxy being optionally substituted with 1–3 halo groups. Within this aspect of the invention, all other variables are as defined with respect to formula I.

Even more particularly, an aspect of the invention that is of interest relates to a compound of formula I wherein two $R^1$ groups represent halo or methyl. Within this aspect of the invention, all other variables are as defined with respect to formula I.

In another aspect of the invention, a compound of formula I is disclosed wherein $R^2$ is taken separately from $R^3$ and is selected from the group consisting of: (a) $C_{1-14}$alkyl optionally substituted with 1–6 halo groups and 1–3 substituents selected from OH, $OC_{1-3}$alkyl, and phenyl, said phenyl being optionally substituted with 1–4 groups independently selected from halo, $OCH_3$, $OCF_3$, $CH_3$ and $CF_3$, and said $C_{1-3}$alkyl portion of $OC_{1-3}$alkyl being optionally substituted with 1–3 halo groups; (b) phenyl or pyridyl optionally substituted with 1–3 halo, OH or $R^a$ groups; (c) $C_{2-10}$ alkenyl, optionally substituted with 1–3 substituents independently selected from halo, OH and $OC_{1-3}$alkyl, said $C_{1-3}$alkyl portion of $OC_{1-3}$alkyl being optionally substituted with 1–3 halo groups; (d) $CH_2CO_2H$; (e) $CH_2CO_2C_{1-6}$alkyl; (f) $CH_2C(O)NHR^a$ and (g) $NH_2$, $NHR^a$ and $N(R^a)_2$, and $R^a$ represents $C_{1-3}$alkyl, $OC_{1-3}$alkyl, $C_{6-10}arC_{1-6}$alkylene or phenyl optionally substituted with 1–3 halo groups.

Within this aspect of the invention, all other variables are as originally defined with respect to formula I.

More particularly, an aspect of the invention is disclosed wherein $R^2$ is taken separately from $R^3$ and is $C_{1-14}$alkyl optionally substituted with 1–6 halo groups and 1–3 substituents selected from OH, $OC_{1-3}$alkyl and phenyl, said phenyl being optionally substituted with 1–4 groups independently selected from halo, $OCH_3$, $OCF_3$, $CH_3$ and $CF_3$, and the alkyl portion of $OC_{1-3}$alkyl being optionally substituted with 1–3 halo groups. Within this aspect of the invention, all other variables are as originally defined with respect to formula I.

Even more particularly, an aspect of the invention that is of particular interest relates to a compound of formula I wherein $R^2$ is taken separately from $R^3$ and represents methyl or cyclopropyl. Within this aspect of the invention, all other variables are as originally defined with respect to formula I.

In a different aspect of the invention, a compound that is of interest is defined in accordance with formula I wherein $R^3$ is taken separately from $R^2$ and is selected from the group consisting of: $C_{1-14}$alkyl, $C_{2-10}$alkenyl, $SC_{1-6}$alkyl, $C_{6-10}$aryl, heterocyclyl and heteroaryl, said alkyl, alkenyl, aryl, heterocyclyl, heteroaryl and the alkyl portion of $SC_{1-6}$alkyl being optionally substituted with (a) R; (b) 1–6 halo groups and (c) 1–3 groups selected from OH, $NH_2$, $NHC_{1-4}$alkyl, $N(C_{1-4}alkyl)_2$, $C_{1-4}$alkyl, $OC_{1-4}$alkyl, CN, $C_{1-4}$alkylS$(O)_x$— wherein x is 0, 1 or 2, $C_{1-4}$alkylSO$_2$NH—, $H_2NSO_2$—, $C_{1-4}$alkylNHSO$_2$— and $(C_{1-4}alkyl)_2NSO_2$—, said $C_{1-4}$alkyl and the $C_{1-4}$alkyl portions of said groups being optionally substituted with phenyl and 1–3 halo groups, and R is selected from heterocyclyl, heteroaryl and aryl, said group being optionally substituted with 1–4 groups selected from halo, $C_{1-4}$alkyl, $C_{1-4}$alkylS$(O)_x$—, with x as previously defined, $C_{1-4}$ alkylSO$_2$NH—, $H_2NSO_2$—, $C_{1-4}$alkylNHSO$_2$—, $(C_{1-4}$ alkyl$)_2$—, CN, OH, $OC_{1-4}$alkyl, and, said $C_{1-4}$alkyl and the $C_{1-4}$alkyl portions of said groups being optionally substituted with 1–5 halo and 1 group selected from OH and $OC_{1-3}$alkyl. Within this aspect of the invention, all other variables are as originally defined with respect to formula I.

More particularly, a compound that is of interest is defined in accordance with formula I wherein $R^3$ is taken separately from $R^2$ and is selected from the group consisting of: $C_{1-14}$alkyl, $C_{6-10}$aryl, heterocyclyl and heteroaryl, said groups being optionally substituted with (a) R; (b) 1–6 halo groups and (c) 1–3 groups selected from OH, $NH_2$, $NHC_{1-4}$alkyl, $N(C_{1-4}alkyl)_2$, $C_{1-4}$alkyl, $OC_{1-4}$alkyl, CN, $C_{1-4}$alkylS$(O)_x$— wherein x is 0, 1 or 2, $C_{1-4}$alkylSO$_2$NH—, $H_2NSO_2$—, $C_{1-4}$alkylNHSO$_2$—, $(C_{1-4}alkyl)_2NSO_2$—, said $C_{1-4}$alkyl and the $C_{1-4}$alkyl portions of said groups being optionally substituted with phenyl and 1–3 halo groups. Within this aspect of the invention, all other variables are as originally defined with respect to formula I.

Even more particularly, a compound that is of interest is defined in accordance with formula I wherein $R_3$ is taken separately and is selected from the group consisting of: cyclopropyl optionally substituted with methyl or phenyl; phenyl optionally substituted with halo, OH, $OCH_3$ or $OCF_3$; heteroaryl selected from benzimidazolyl, indolyl, benzofuranyl, and dihydrobenzofuranyl, said heteroaryl groups being optionally substituted with: (a) R; (b) 1–6 halo groups or (c) 1–3 groups selected from OH, $NH_2$, $NHC_{1-4}$alkyl, $N(C_{1-4}alkyl)_2$, $C_{1-4}$alkyl, $OC_{1-4}$alkyl, CN, $C_{1-4}$alkylS$(O)_x$— wherein x is 0, 1 or 2, $C_{1-4}$alkylSO$_2$NH—, $H_2NSO_2$—, $C_{1-4}$alkylNHSO$_2$—, $(C_{1-4}alkyl)_2NSO_2$—, said $C_{1-4}$alkyl and the $C_{1-4}$alkyl portions of said groups being optionally substituted with phenyl and 1–3 halo groups, and R is selected from heterocyclyl, heteroaryl and aryl, said group being optionally substituted with 1–4 groups selected from halo, $C_{1-4}$alkyl, OH, $OC_{1-4}$alkyl, and, said $C_{1-4}$alkyl and the $C_{1-4}$alkyl portions of said groups being optionally substituted with 1–5 halo groups and 1 group selected from OH and $OC_{1-3}$alkyl. Within this aspect of the invention, all other variables are as originally defined with respect to formula I.

In a different aspect of the invention that is of interest, a compound of formula I is described wherein $R_1$ and $R_3$ are taken together and represent: (a) a $C_{3-8}$ alkanediyl forming a fused 5–10 membered non-aromatic ring optionally interrupted with 1 double bond, and optionally interrupted by 1 heteroatom selected from O, S and N; or (b) a fused 6–10 membered aromatic monocyclic or bicyclic group, said alkanediyl and aromatic monocyclic or bicyclic group being optionally substituted with 1–3 halo atoms, and 1–2 of OH, $C_{1-3}$alkyl, $OC_{1-3}$alkyl, halo$C_{1-3}$alkyl, halo$C_{1-3}$alkoxy and phenyl, said phenyl being optionally substituted with 1–2 groups independently selected from halo, $C_{1-3}$alkyl, $OC_{1-3}$alkyl, and said $C_{1-3}$alkyl and the $C_{1-3}$alkyl portion of $OC_{1-3}$alkyl being optionally substituted with 1–3 halo groups. Within this aspect of the invention, all other variables are as originally defined with respect to formula I.

More particularly, an aspect of the invention that is of interest relates to a compound of formula I wherein R is selected from heterocyclyl, heteroaryl and aryl, said group being optionally substituted with 1–4 halo groups and 1–2 groups selected from $C_{1-4}$alkyl, $C_{1-4}$alkylS$(O)_x$—, wherein x is 0, 1 or 2, $C_{1-4}$ alkylSO$_2$NH—, $H_2NSO_2$—, $C_{1-4}$alkylNHSO$_2$—, $(C_{1-4}alkyl)_2NSO_2$—, CN, OH and $OC_{1-4}$alkyl, said $C_{1-4}$alkyl and the $C_{1-4}$alkyl portions of said groups being optionally substituted with 1–3 halo groups and 1 group selected from OH and $OC_{1-3}$alkyl. Within this aspect of the invention, all other variables are as originally defined with respect to formula I.

Species falling within the scope of the invention include those disclosed in the examples. A compound that is of particular interest is defined as having the structural formula:

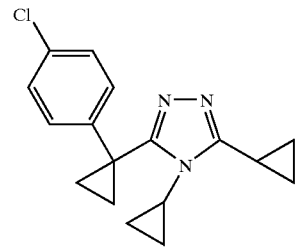

as well as pharmaceutically acceptable salts and solvates thereof.

Another compound that is of particular interest is defined as having the structural formula:

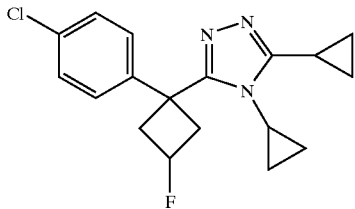

as well as pharmaceutically acceptable salts and solvates thereof.

Yet another compound that is of particular interest is defined as having the structural formula:

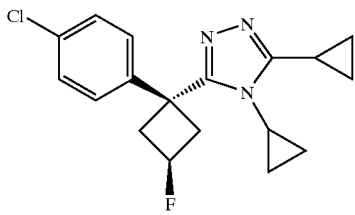

as well as pharmaceutically acceptable salts and solvates thereof.

In a different aspect of the invention, a pharmaceutical composition is addressed comprising a compound in accordance with formula I or a salt or hydrate thereof, in combination with a pharmaceutically acceptable carrier.

In another aspect of the invention, a method of treating hyperglycemia, diabetes or insulin resistance in a mammalian patient in need of such treatment is addressed, which comprises administering to said patient an effective amount of a compound in accordance with formula I or a salt or solvate thereof.

In another aspect of the invention, a method of treating non-insulin dependent diabetes mellitus is disclosed in a mammalian patient in need of such treatment comprising administering to the patient an anti-diabetic effective amount of a compound in accordance with formula I.

In another aspect of the invention, a method of treating obesity in a mammalian patient in need of such treatment is disclosed comprising administering to said patient a compound in accordance with formula I in an amount that is effective to treat obesity.

In another aspect of the invention, a method of treating Syndrome X in a mammalian patient in need of such treatment is disclosed, comprising administering to said patient a compound in accordance with formula I in an amount that is effective to treat Syndrome X.

In another aspect of the invention, a method of treating a lipid disorder selected from the group conisting of dyslipidemia, hyperlipidemia, hypertriglyceridemia, hypercholesterolemia, low HDL and high LDL in a mammalian patient in need of such treatment is disclosed, comprising administering to said patient a compound in accordance with formula I in an amount that is effective to treat said lipid disorder.

In another aspect of the invention, a method of treating atherosclerosis in a mammalian patient in need of such treatment is disclosed, comprising administering to said patient a compound in accordance with formula I in an amount effective to treat atherosclerosis.

In another aspect of the invention, a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalina patient in need of such treatment is disclosed, comprising administering to the patient a compound in accordance with formula I in an amount that is effective to treat said condition.

In another aspect of the invention, a method of delaying the onset of a condition selected from the group consisting of (1) hyperglycemia, (2) low glucose tolerance, (3) insulin resistance, (4) obesity, (5) lipid disorders, (6) dyslipidemia, 7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalina patient in need of such treatment is disclosed, comprising administering to the patient a compound in accordance with formula I in an amount that is effective to delay the onset of said condition.

In another aspect of the invention, a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment is disclosed, comprising administering to the patient a compound in accordance with formula I in an amount that is effective to reduce the risk of developing said condition.

In another aspect of the invention, a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient an effective amount of a compound as defined in formula I and a compound selected from the group consisting of:
  (a) DP-IV inhibitors;
  (b) insulin sensitizers selected from the group consisting of (i) PPAR agonists and (ii) biguanides;
  (c) insulin and insulin mimetics;
  (d) sulfonylureas and other insulin secretagogues;
  (e) (α-glucosidase inhibitors;
  (f) glucagon receptor antagonists;
  (g) GLP-1, GLP-1 mimetics, and GLP-1 receptor agonists;

(h) GIP,GIP mimetics, and GIP receptor agonists;
(i) PACAP, PACAP mimetics, and PACAP receptor 3 agonists;
(j) cholesterol lowering agents selected from the group consisting of
   (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption,
   (vii) acyl CoA:cholesterol acyltransferase inhibitors, and (viii) anti-oxidants;
(k) PPAR δ agonists;
(l) antiobesity compounds;
(m) an ileal bile acid transporter inhibitor
(n) anti-inflammatory agents excluding glucocorticoids; and
(o) protein tyrosine phosphatase-1B (PTP-1B) inhibitors, said compounds being administered to the patient in an amount that is effective to treat said condition.

In another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, comprising administering to the patient a therapeutically effective amount of a compound as defined in formula I and an HMG-CoA reductase inhibitor.

More particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin.

Even more particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin selected from the group consisting of lovastatin, simvastatin, pravastatin, fluvastatin, atorvastatin, itavastatin, ZD-4522 and rivastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound as defined in formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound as defined in formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin.

Even more particularly, a method for delaying the onset or reducing the risk of developing atherosclerosis in a human patient in need of such treatment is disclosed, wherein the HMG-Co A reductase inhibitor is a statin selected from the group consisting of: lovastatin, simvastatin, pravastatin, fluvastatin, atorvastatin, itavastatin, ZD-4522 and rivastatin.

Even more particularly, a method for delaying the onset or reducing the risk of developing atherosclerosis in a human patient in need of such treatment is disclosed, wherein the statin is simvastatin.

In another aspect of the invention, a method for delaying the onset or reducing the risk of developing atherosclerosis in a human patient in need of such treatment is disclosed, wherein the HMG-Co A reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises
(1) a compound according to formula I,
(2) a compound selected from the group consisting of:
   (a) DP-IV inhibitors;
   (b) insulin sensitizers selected from the group consisting of (i) PPAR agonists and (ii) biguanides;
   (c) insulin and insulin mimetics;
   (d) sulfonylureas and other insulin secretagogues;
   (e) α-glucosidase inhibitors;
   (f) glucagon receptor antagonists;
   (g) GLP-1, GLP-1 mimetics, and GLP-1 receptor agonists;
   (h) GIP, GIP mimetics, and GIP receptor agonists;
   (i) PACAP, PACAP mimetics, and PACAP receptor 3 agonists;
   (j) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
   (k) PPAR δ agonists;
   (l) antiobesity compounds;
   (m) an ileal bile acid transporter inhibitor;
   (n) anti-inflammatory agents other than glucocorticoids; and
   (o) protein tyrosine phosphatase-1B (PTP-1B) inhibitors; and
(3) a pharmaceutically acceptable carrier.

The term "pharmaceutically acceptable salt" refers to salts prepared from pharmaceutically acceptable bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts in the solid form may exist in more than one crystal structure, and may also be in the form of hydrates and polyhydrates.

Salts derived from pharmaceutically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred pharamaceutically acceptable acids include citric, hydrobromic, hydrochloric, maleic, phosphoric, sulfuric, and tartaric acids. In most cases, compounds of the present invention are basic because the triazole ring is basic. The triazole compounds of this invention may also be made and handled as non-pharmaceutically acceptable salts (e.g. trifluoroacetate salts) during synthesis before they are used in making pharmaceuticals.

It will be understood that, as used herein, references to the compounds of Formula I are meant to also include the pharmaceutically acceptable salts, and also salts that are not pharmaceutically acceptable when they are used as precursors to the free compounds or their pharmaceutically acceptable salts or in other synthetic manipulations.

"Solvates, and in particular, the hydrates of the compounds of formula I are included in the present invention as well.

Metabolites of the compounds of this invention that are therapeutically active and that are also defined by Formula I are also within the scope of this invention. Prodrugs are compounds that are converted to therapeutically active compounds as they are being administered to a patient or after they have been administered to a patient. Prodrugs, which themselves do not have the structures claimed herein, but which are converted to active compounds defined by Formula I during or after administration to a mammalian patient, are prodrugs and are compounds of this invention, as are their active metabolites that are defined by Formula I.

The compounds described herein are selective inhibitors of the 11β-HSD1 enzyme. Thus, the present invention relates to the use of the 11β-HSD1 inhibitor for inhibiting the reductase activity of 11β-hydroxysteroid dehydrogenase, which is responsible for the conversion of cortisone to cortisol. Excess cortisol is associated with numerous disorders, including NIDDM, obesity, dyslipidemia, insulin resistance and hypertension. Administration of the compounds decreases the level of cortisol and other 11β-hydroxysteroids in target tissues, thereby reducing the effects of excessive amounts of cortisol and other 11β-hydroxysteroids. Inhibition of 11β-HSD1 can be used to treat and control diseases mediated by abnormally high levels of cortisol and other 11β-hydroxysteroids, such as NIDDM, obesity, hypertension and dyslipidemia.

The present invention includes the use of an 11β-HSD1 inhibitor for the treatment, control, amelioration, prevention, delaying the onset of or reducing the risk of developing the diseases and conditions that are described herein, as mediated by excess or uncontrolled amounts of cortisol and/or other corticosteroids in a mammalian patient, particularly a human, by the administration of an effective amount of a compound of formula I or a pharmaceutically acceptable salt or solvate thereof. Inhibition of the 11β-HSD1 enzyme limits the conversion of cortisone, which is normally inert, to cortisol, which can cause or contribute to the symptoms of these diseases and conditions if present in excessive amounts.

NIDDM and Hypertension

The compounds of this invention are selective inhibitors of 11β-HSD1 over 11β-HSD2. While the inhibition of 11β-HSD1 is useful for reducing cortisol levels and treating conditions related thereto, inhibition of 11β-HSD2 is associated with serious side effects, such as hypertension.

Cortisol is an important and well recognized anti-inflammatory hormone, which also acts as an antagonist to the action of insulin in the liver, such that insulin sensitivity is reduced, resulting in increased gluconeogenesis and elevated levels of glucose in the liver. Patients who already have impaired glucose tolerance have a greater probability of developing type 2 diabetes in the presence of abnormally high levels of cortisol.

High levels of cortisol in tissues where the mineralocorticoid receptor is present often lead to hypertension. Inhibition of 11β-HSD1 shifts the ratio of cortisol and cortisone in specific tissues in favor of cortisone.

Administration of a therapeutically effective amount of an 11β-HSD1 inhibitor is effective in treating, controlling and ameliorating the symptoms NIDDM, and administration of a therapeutically effective amount of an 11β-HSD1 inhibitor on a regular basis delays or prevents the onset of NIDDM, particularly in humans.

Cushing's Syndrome

The effect of elevated levels of cortisol is also observed in patients who have Cushing's syndrome, which is a metabolic disease characterized by high levels of cortisol in the blood stream. Patients with Cushing's syndrome often develop NIDDM.

Obesity, Metabolic Syndrome, Dyslipidemia

Excessive levels of cortisol have been associated with obesity, perhaps due to increased hepatic gluconeogenesis. Abdominal obesity is closely associated with glucose intolerance, hyperinsulinemia, hypertriglyceridemia, and other factors of Syndrome X, such as high blood pressure, elevated VLDL and reduced HDL. Montague et al., Diabetes, 2000, 49: 883–888. Thus, the administration of an effective amount of an 11β-HSD1 inhibitor is useful in the treatment or control of obesity. Long-term treatment with an 11β-HSD1 inhibitor is also useful in delaying or preventing the onset of obesity, especially if the patient uses an 11β-HSD1 inhibitor in combination with controlled diet and exercise.

By reducing insulin resistance and maintaining serum glucose at normal concentrations, compounds of this invention also have utility in the treatment and prevention of conditions that accompany Type II diabetes and insulin resistance, including the metabolic syndrome ("Syndrome X"), obesity, reactive hypoglycemia and diabetic dyslipidemia.

Cognition and Dementia

Excessive levels of cortisol in the brain may also result in neuronal loss or dysfunction through the potentiation of neurotoxins. Cognitive impairment has been associated with aging, and excess levels of cortisol in the brain. See J. R. Seckl and B. R. Walker, Endocrinology, 2001, 142: 1371–1376, and references cited therein. Administration of an effective amount of an 11β-HSD1 inhibitor results in the reduction, amelioration, control or prevention of cognitive impairment associated with aging and of neuronal dysfunction.

Atherosclerosis

As described above, inhibition of 11β-HSD1 activity and a reduction in the amount of cortisol are beneficial in treating or controlling hypertension. Since hypertension and dyslipidemia contribute to the development of atherosclerosis, administration of a therapeutically effective amount of an 11β-HSD1 inhibitor of this invention may be especially beneficial in treating, controlling, delaying the onset of or preventing atherosclerosis.

Effects on Pancreas

Inhibition of 11β-HSD1 activity in isolated murine pancreatic β-cells improves glucose stimulated insulin secretion (B. Davani et al., J. Biol. Chem., 2000, 275: 34841–34844). Glucocorticoids have been shown to reduce insulin secretion in vivo. (B. Billaudel et al., Horm. Metab. Res., 1979, 11: 555–560).

Reduction of Intraocular Pressure

Recent data suggests a connection between the levels of glucocorticoid target receptors and the 11β-HSD enzymes and thesusceptibility to glaucoma (J. Stokes et al., Invest. Ophthamol., 2000, 41: 1629–1638). Therefore, inhibition of 11β-HSD1 activity is useful in reducing intraocular pressure in the treatment of glaucoma.

Immunomodulation

In certain disease states, such as tuberculosis, psoriasis, and even under conditions of excessive stress, high glucocorticoid activity shifts the immune response to a humoral response, when in fact a cell based response may be more beneficial to the patient. Inhibition of 11β-HSD1 activity and the attendant reduction in glucocorticoid levels shifts the immune response toward a cell based response. See D. Mason, Immunology Today, 1991, 12: 57–60, and G. A. W. Rook, Baillièr's Clin,Endocrinol. Metab., 1999, 13: 576–581.

Osteoporosis

Glucocorticoids can inhibit bone formation, which can result in a net bone loss. 11β-HSD1 has a role in bone resorption. Inhibition of 11β-HSD1 is beneficial in preventing bone loss due to osteoporosis. See C. H. Kim et al., J. Endocrinol., 1999, 162: 371–379; C. G. Bellows et al., Bone, 1998,23: 119–125; and M. S. Cooper et al., Bone, 2000, 27: 375–381.

Other Utilities

The following diseases, disorders and conditions can be treated, controlled, prevented or delayed, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other disorders where insulin resistance is a component.

The above diseases and conditions can be treated using the compounds of formula I, or the compound can be administered to prevent or reduce the risk of developintg the diseases and conditions described herein. Since concurrent inhibition of 11β-HSD2 may have deleterious side effects or may actually increase the amount of cortisol in the target tissue where reduction of cortisol is desired, selective inhibitors of 11β-HSD1 with little or no inhibition of 11β-HSD2 are desirable.

The 11β-HSD1 inhibitors of formula I generally have an inhibition constant $IC_{50}$ of less than about 500 nM, and preferably less than about 100 nM. Generally, the $IC_{50}$ ratio for 11β-HSD2 to 11β-HSD1 of a compound is at least about two or more, and preferably about ten or greater. Even more preferred are compounds with an $IC_{50}$ ratio for 11β-HSD2 to 11β-HSD1 of about 100 or greater. For example, for compounds having an $IC_{50}$ the compounds ideally demonstrate an inhibition constant $IC_{50}$ against 11β-HSD2 greater than about 500 nM, and preferably greater than 1000 nM.

Compounds of Formula I may be used in combination with one or more other drugs in the treatment, prevention, suppression or amelioration of diseases or conditions for which compounds of Formula I or the other drugs have utility. Typically the combination of the drugs is safer or more effective than either drug alone, or the combination is safer or more effective than would be expected based on the additive properties of the individual drugs. Such other drug(s) may be administered, by a route and in an amount commonly used contemporaneously or sequentially with a compound of Formula I. When a compound of Formula I is used contemporaneously with one or more other drugs, a combination product containing such other drug(s) and the compound of Formula I is preferred. However, combination therapy also includes therapies in which the compound of Formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and (ii) biguanides, such as metformin and phenformin;

(c) insulin or insulin mimetics;

(d) sulfonylureas and other insulin secretagogues such as tolbutamide and glipizide, meglitinide and related materials;

(e) β-glucosidase inhibitors (such as acarbose);

(f) glucagon receptor antagonists such as those disclosed in WO 98/04528, WO 99/01423, WO 00/39088 and WO 00/69810;

(g) GLP-1, GLP-1 mimetics, and GLP-1 receptor agonists such as those disclosed in WO00/42026 and WO00/59887;

(h) GIP, GIP mimetics such as those disclosed in WO00/58360, and GIP receptor agonists;

(i) PACAP, PACAP mimetics, and PACAP receptor 3 agonists such as those disclosed in WO 01/23420;

(j) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv)

inhibitors of cholesterol absorption, such as for example ezetimibe and beta-sitosterol, (v) acyl CoA::cholesterol acyltransferase inhibitors, such as for example avasimibe, and (vi) anti-oxidants such as probucol;

(k) PPARδ agonists, such as those disclosed in WO97/28149;

(l) antiobesity compounds such as fenfluramine, dexfenfluramine, phentermine, sibutramine, orlistat, neuropeptide Y5 inhibitors, CB1 receptor inverse agonists and antagonists, and $\beta_3$ adrenergic receptor agonists;

(m) an ileal bile acid transporter inhibitor;

(n) agents intended for use in inflammatory conditions other than glucocorticoids, such as aspirin, non-steroidal anti-inflammatory drugs, azulfidine, and cyclooxygenase 2 selective inhibitors, and (o) protein tyrosine phosphatase-1B (PTP-1B) inhibitors.

The above combinations include a compound of formula I, or a pharmaceutically acceptable salt, hydrate or solvate thereof, not only with one or more other active compounds. Non-limiting examples include combinations of compounds of Formula I with two or more active compounds selected from biguanides, sulfonylureas, HMG-CoA reductase inhibitors, PPAR agonists, PTP-1B inhibitors, DP-IV inhibitors and anti-obesity compounds.

Any suitable route of administration may be employed for providing a mammal, especially a human, with an effective dose of a compound of the present invention. For example, oral, rectal, topical, parenteral, ocular, pulmonary, nasal and the like may be employed. Dosage forms include tablets, troches, dispersions, suspensions, solutions, capsules, creams, ointments, aerosols and the like. Preferably the compound of Formula I is administered orally.

The effective dosage of the active ingredient varies depending on the particular compound employed, the mode of administration, the condition being treated and the severity of the condition. Such dosages may be ascertained readily by a person skilled in the art.

When treating or preventing the diseases and conditions described herein, for which compounds of Formula I are indicated, satisfactory results are obtained when the compounds of the invention are administered at a daily dosage of from about about 0.1 to about 100 milligram per kilogram (mpk) of body weight, preferably given as a single daily dose or in divided doses about two to six times a day. The total daily dosage thus ranges from about 0.1 mg.to about 1000 mgs., preferably from about 1 mg. to about 50 mgs. In the case of a typical 70 kg adult human, the total daily dose will range from about 7 mgs. to about 350 mgs. This dosage may be adjusted to provide the optimal therapeutic response.

Another aspect of the present invention relates to a pharmaceutical composition which comprises a compound of Formula I, or a pharmaceutically acceptable salt, hydrate otr solvate thereof, in combination with a pharmaceutically acceptable carrier.

The compositions include compositions suitable for oral, rectal, topical, parenteral (including subcutaneous, intramuscular, and intravenous), ocular (ophthalmic), transdermal, pulmonary (nasal or buccal inhalation), or nasal administration, although the most suitable route in any given case will depend on the nature and severity of the condition being treated and the active ingredient. They may be conveniently presented in unit dosage form and prepared by any of the methods well-known in the art of pharmacy.

The compound of Formula I can be combined with the pharmaceutical carrier according to conventional pharmaceutical compounding techniques. Carriers take a wide variety of forms. For example, carriers for oral liquid compositions include, e.g., water, glycols, oils, alcohols, flavoring agents, preservatives, coloring agents and other components used in the manufacture of oral liquid suspensions, elixirs and solutions. Carriers such as starches, sugars and microcrystalline cellulose, diluents, granulating agents, lubricants, binders, disintegrating agents and the like are used to prepare oral solid dosage forms, e.g., powders, hard and soft capsules and tablets. Solid oral preparations are preferred over oral liquids.

The oral solid dosage forms may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. Capsules may also contain a liquid carrier such as a fatty oil.

Various other materials may be present to act as coatings or to modify the physical form of the dosage unit. For instance, tablets may be coated with shellac, sugar or both.

Tablets may be coated by standard aqueous or nonaqueous techniques. The typical percentage of active compound in these compositions may, of course, be varied from about 2 percent to about 60 percent on a w/w basis. Thus, tablets contain a compound of formula I or a salt or hydrate thereof in an amount ranging from as low as about 0.1 mg to as high as about 1.5 g, preferably from as low as about 1.0 mg to as high as about 500 mg, and more preferably from as low as about 10 mg to as high as about 100 mg.

Oral liquids such as syrups or elixirs may contain, in addition to the active ingredient, sucrose as a sweetening agent, methyl and propylparabens as preservatives, a dye and a flavoring such as cherry or orange flavor.

Parenterals are typically in the form of a solution or suspension, typically prepared with water, and optionally including a surfactant such as hydroxypropylcellulose. Dispersions can be prepared in glycerol, liquid polyethylene glycols and mixtures thereof in oils. Typically preparations that are in diluted form also contain a preservative.

The pharmaceutical injectable dosage forms, including aqueous solutions and dispersions and powders for the extemporaneous preparation of injectable solutions or dispersions, are also sterile and must be fluid to the extent that easy syringability exists; they must be stable under the conditions of manufacture and storage and are usually preserved. The carrier thus includes the solvent or dispersion medium containing, for example, water, ethanol, polyol (e.g. glycerol, propylene glycol and liquid polyethylene glycol), suitable mixtures thereof, and vegetable oils.

ASSAYS: MEASUREMENT OF INHIBITION CONSTANTS

In vitro enzymatic activity was assessed for test compounds via a Scintillation Proximity Assay (SPA). In short, tritiated-cortisone substrate, NADPH cofactor and titrated compound were incubated with 11β-HSD1 enzyme at 37° C. to allow conversion to cortisol to progress. Following this incubation, a preparation of protein A coated SPA beads, pre-blended with anti-cortisol monoclonal antibody and a non-specific 11β-HSD inhibitor, was added to each well. The mixture was shaken at 15° C. and was then read on a liquid scintillation counter suitable for 96 well plates. Percent inhibition was calculated relative to a non-inhibited control well and $IC_{50}$ curves were generated. This assay was similarly applied to 11β-HSD2, whereby tritiated cortisol and NAD were used as the substrate and cofactor, respectively. To begin the assay, 40 μL of substrate (25 nM ³H-Cortisone+1.25 mM NADPH in 50 mM HEPES Buffer, pH 7.4) was added to designated wells on a 96 well plate. Solid compound was dissolved in DMSO at 10 mM followed by a subsequent 50 fold dilution in DMSO. The diluted material was then titrated 4 fold, seven times. 1 μL of each titrated compound was then added in duplicate to the substrate. To start the reaction, 10 μL of 11β-HSD1 microsome from CHO transfectants was added to each well at the appropriate concentration to yield approximately 10% conversion of the starting material. For ultimate calculation of percent inhibition, a series of wells were added that represented the assay minimum and maximum: one set that contained substrate without compound or enzyme (background), and another set that contained substrate and enzyme without any compound (maximum signal). The plates were spun briefly at a low speed in a centrifuge to pool the reagents, sealed with an adhesive strip, mixed gently, and incubated at 37° C. for 2 hours. After incubation, 45 μL of SPA beads, pre-suspended with anti-cortisol monoclonal antibody and non-specific 11β-HSD inhibitor, were added to each well. The plates were resealed and shaken gently for greater than 1.5 hours at 15° C. Data was collected on a plate based liquid scintillation counter such as a Topcount. To control for inhibition of anti-cortisol antibody/cortisol binding, substrate spiked with 1.25 nM $^3$H cortisol was added to designated single wells. 1 μL of 200 μM compound was added to each of these wells, along with 10 μL of buffer instead of enzyme. Any calculated inhibiton was due to compound interfering with the cortisol binding to the antibody on the SPA beads.

ASSAYS: MEASUREMENT OF IN VIVO INHIBITION

In general terms, the test compound was dosed orally to a mammal and a prescribed time interval was allowed to elapse, usually between 1 and 24 hours. Tritiated cortisone was injected intavenously, followed several minutes later by blood collection. Steroids were extracted from the separated serum and analyzed by HPLC. The relative levels of ³H-cortisone and its reduction product, ³H-cortisol, were determined for the compound and vehicle-dosed control groups. The absolute conversion, as well as the percentage of inhibtion, were calculated from these values.

More specifically, compounds were prepared for oral dosing by dissolving them in vehicle (5% hydroxypropyl-beta-cyclodextrin v/v H₂O, or equivalent) at the desired concentration to allow dosing at typically 10 milligrams per kilogram. Following an overnight fasting, the solutions were dosed to ICR mice (obtained from Charles River) by oral gavage, 0.5 mL per dose per animal, with three animals per test group.

After the desired time had passed, routinely either 1 or 4 hours, 0.2 mL of 3 μM ³H-cortisone in dPBS was injected by tail vein. The animal was caged for two minutes followed by euthanasia in a CO₂ chamber. Upon expiration, the mouse was removed and blood was collected by cardiac puncture. The blood was set aside in a serum separation tube for no less than 30 minutes at room temperature to allow for adequate coagulation. After the incubation period, blood was separated into serum by centrifugation at 300×g, 4° C., for 10 minutes.

To analyze the steroids in the serum they were first extracted with organic solvent. A 0.2 mL volume of serum was transferred to a clean microcentrifuge tube. To this a 1.0 mL volume of ethyl acetate was added, followed by vigorous vortexing for 1 minute. A quick spin on a microcentrifuge pelleted the aqueous serum proteins and clarified the organic supernatant. 0.85 mL of the upper organic phase was transferred to a fresh microcentrifuge tube and dried. The dried sample was resuspended in 0.250 mL of DMSO containing a high concentration of cortisone and cortisol for analysis by HPLC.

A 0.200 mL sample was injected onto a Metachem Inertsil C-18 chromatography column equilibrated in 30% methanol. A slow linear gradient to 50% methanol separated the target steroids; simultaneous monitoring by UV at 254 nM of the cold standards in the resuspension solution acted as an internal standard. The tritium signal was collected by a radiochromatography detector that uploaded data to software for analysis. The percent conversion of ³H-cortisone to ³H-cortisol was calculated as the ratio of AUC for cortisol over the combined AUC for cortisone and cortisol.

The following examples are illustrative only and should not be construed as limiting the invention.

EXAMPLE 1

General Scheme

R-C(=O)-OH (Starting Material (S.M.))  +  imino ether A  →  (1. TFFH, Hydrazine, Et₃N, DMF, 25° C., 1 hour; 2. 120° C., 12 hours)  →  triazole product

| Substance | Amount | MW | Conc. | Mmoles | equiv's |
|---|---|---|---|---|---|
| S.M. in DMF | 714 μL | N/A | 0.14 M in DMF | 0.1 | 1 |
| TFFH in DMF | 200 μL | N/A | 0.5 M in DMF | 0.1 | 1 |
| Triethylamine in DMF | 400 μL | N/A | 0.5 M in DMF | 0.2 | 2 |
| Hydrazine in DMF | 240 μL | N/A | 0.5 M in DMF | 0.12 | 1.2 |
| Imino ether A in DMF | 600 μL | N/A | 0.25 M in DMF | 0.15 | 1.5 |

The following synthesis of a 1-D, single, pure compound library was performed on a Myriad Core System. All reaction vessels were dried under a stream of nitrogen at 120° C. for 12 hours prior to use. Solvents were dried over sieves for at least 12 hours prior to use. Reagents and subunits (carboxylic acids and 8-methoxy-2,3,4,5,6,7-hexahydroazocine (imino ether A)) were dissolved in appropriate solvents immediately prior to use.

Synthesis

The carboxylic acids shown in the table below as starting materials were added to dry, 10 mL fritted Myriad reaction vessels under nitrogen (714 μL, 0.1 mmoles, 0.14 M in N,N-dimethylformamide (DMF)). Fluoro-N,N,N',N'-tetramethylformamidinium hexafluorophosphate (TFFH) (200 μL, 0.1 mmoles, 0.5M in DMF) followed by triethylamine (400 μL, 0.2 mmoles, 0.5 M in DMF) and hydrazine (240 μL, 0.12 mmoles, 0.5 M in DMF) was added to each of the reaction vessels under nitrogen. The reactions were aged 1 hour at 25° C.; the reactions were gas agitated (1 second pulse every 5 minutes) during the age. 8-Methoxy-2,3,4,5,6,7-hexahydroazocine (imino ether A, 600 μL, 0.15 mmoles, 0.25 M in DMF) was added to each reaction vessel under nitrogen. The reactions were aged 12 hours at 120° C. while gas agitating (1 second pulse every 5 minutes) and then cooled to room temperature. After cooling, the crude reaction mixtures were analyzed by LC-MS (Method 1). All 180 crude reactions were purified by preparative HPLC using mass based detection (Method 2). The collected fractions were then analyzed for purity by LC-MS (Method 1); fractions found to be greater than 90% purity were pooled into tared 40 mL EPA vials and lyophilized.

| HPLC Conditions Analytical LC Method 1: | |
|---|---|
| Column: | MetaChem Polaris C-18A, 30 mm × 4.6 mm, 5.0 μm |
| Eluent A: | 0.1% Trifluoroacetic acid (TFA) in Water |
| Eluent B: | 0.1% TFA in Acetonitrile |
| Gradient: | 5% B to 95% B in 3.3 minutes, ramp back to 5% B in 0.3 min |
| Flow: | 2.5 mL/min. |
| Column Temperature: | 50° C. |
| Injection amount: | 5 μL of undiluted crude reaction mixture or purified fraction. |
| Detection: | UV at 220 and 254 nm. MS: API-ES ionization mode, mass scan range (100–600 amu) ELSD: Light Scattering Detector |

| Preparative LC Method 2: | |
|---|---|
| Column: | MetaChem Polaris C-18A, 100 mm × 21.2 mm, 10 μm |
| Eluent A: | 0.1% TFA in Water |
| Eluent B: | 0.1% TFA in Acetonitrile |
| Pre-inject Equilibration: | 1.0 min |
| Post-Inject Hold: | 1.0 min |
| Gradient: | 10% B to 100% B in 6.0 minutes, hold at 100% B for an additional 2.0 minutes, ramp back from 100% B to 10% B in 1.5 minutes. |
| Flow: | 20 mL/min. |
| Column Temperature: | ambient |
| Injection amount: | 1.5 mL of undiluted crude reaction mixture. |
| Detection: | MS: API-ES ionization mode, mass scan range (100–600 amu), fraction collection triggered by detection of M + 1 |

Lyophilization Parameters

Initial Freeze Setpoint: 1 hour at −70° C.
Drying Phase Condenser Setpoint: −50° C.

| Drying Phase Table: | | |
|---|---|---|
| Shelf Temperature (° C.) | Duration (minutes) | Vacuum Setpoint (mTorr) |
| −60 | 240 | 25 |
| −40 | 240 | 25 |
| 5 | 480 | 25 |
| 20 | 1000 | 25 |

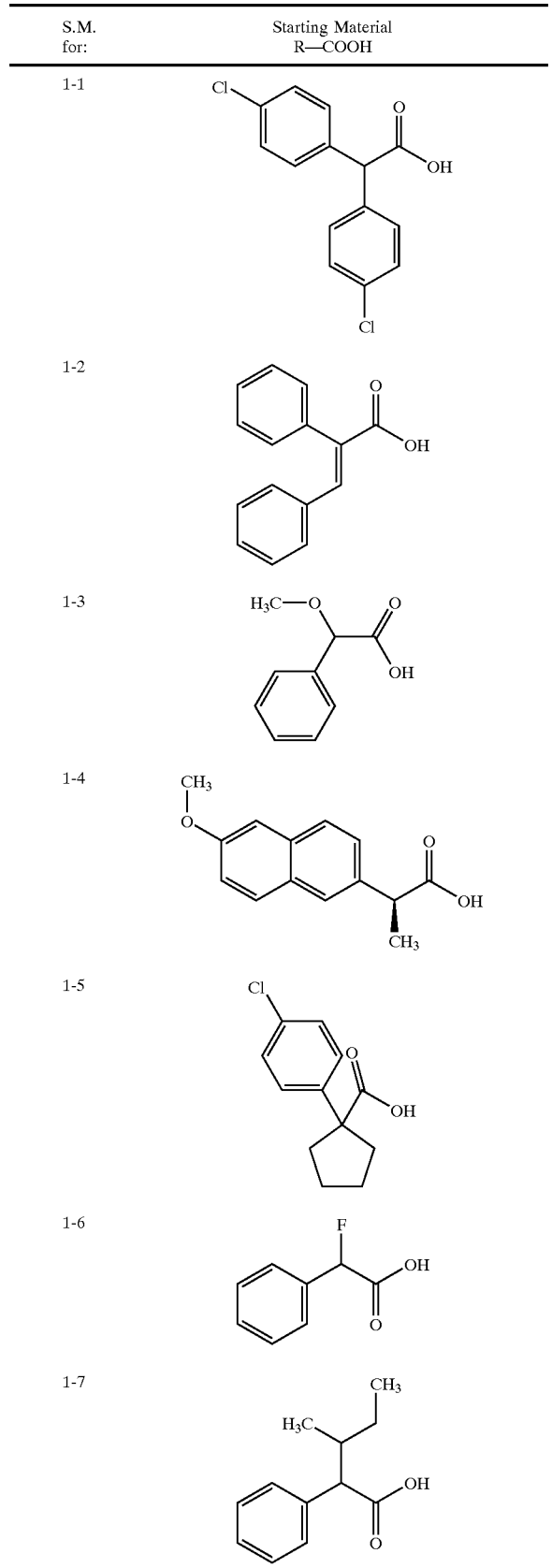

| S.M. for: | Starting Material R—COOH |
|---|---|
| 1-1 | |
| 1-2 | |
| 1-3 | |
| 1-4 | |
| 1-5 | |
| 1-6 | |
| 1-7 | |

-continued

| S.M. for: | Starting Material R—COOH |
|---|---|
| 1-8 | 2-(4-isobutylphenyl)propanoic acid (ibuprofen) |
| 1-9 | 2-(ethylthio)-2,2-diphenylacetic acid with pyridine |
| 1-10 | (S)-2-phenylpropanoic acid |
| 1-11 | (S)-2-phenylbutanoic acid |
| 1-12 | 2-(2-fluoro-biphenyl-4-yl)propanoic acid (flurbiprofen) |

-continued

| S.M. for: | Starting Material R—COOH |
|---|---|
| 1-13 | (S)-2-(2-fluoro-biphenyl-4-yl)propanoic acid |
| 1-14 | (S)-2-(4-isobutylphenyl)propanoic acid |
| 1-15 | (S)-2-phenylpropanoic acid |
| 1-16 | (S)-2-phenylbutanoic acid |

| Cpd | Structure (parent) | Name | Retention Time (min) | MS ESI (m/z) |
|---|---|---|---|---|
| 1-1 | 3-[bis(4-chlorophenyl)methyl]-5,6,7,8,9,10-hexahydro[1,2,4]triazolo[4,3-α]azocine trifluoroacetate salt | | 1.986 | 386.20 |

-continued

| Cpd | Structure (parent) | Name | Retention Time (min) | MS ESI (m/z) |
|---|---|---|---|---|
| 1-2 | | 3-[(E)-1,2-diphenylethenyl]-5,6,7,8,9,10-hexahydro[1,2,4]triazolo[4,3-α]azocine trifluoroacetate salt | 1.812 | 330.25 |
| 1-3 | | 3-[methoxy(phenyl)methyl]-5,6,7,8,9,10-hexahydro[1,2,4]triazolo[4,3-α]azocine trifluoroacetate salt | 1.377 | 272.2 |
| 1-4 | | 3-[(1S)-1-(6-methoxy-2-naphthyl)ethyl]-5,6,7,8,9,10-hexahydro[1,2,4]triazolo[4,3-α]azocine trifluoroacetate salt | 1.668 | 336.25 |
| 1-5 | | 3-[1-(4-chlorophenyl)cyclopentyl]-5,6,7,8,9,10-hexahydro[1,2,4]triazolo[4,3-α]azocine trifluoroacetate salt | 1.77 | 329.87 |
| 1-6 | | 3-[fluoro(phenyl)methyl]-5,6,7,8,9,10-hexahydro[1,2,4]triazolo[4,3-α]azocine trifluoroacetate salt | 1.45 | 259.33 |

-continued

| Cpd | Structure (parent) | Name | Retention Time (min) | MS ESI (m/z) |
|---|---|---|---|---|
| 1-7 | | 3-(2-methyl-1-phenylbutyl)-5,6,7,8,9,10-hexahydro[1,2,4]triazolo[4,3-α]azocine trifluoroacetate salt | 1.73 | 297.4 |
| 1-8 | | 3-[1-(4-isobutylphenyl)ethyl]-5,6,7,8,9,10-hexahydro[1,2,4]triazolo[4,3-α]azocine trifluoroacetate salt | 1.93 | 311.5 |
| 1-9 | | 3-[(ethylthio)(diphenyl)methyl]-5,6,7,8,9,10-hexahydro[1,2,4]triazolo[4,3-α]azocine trifluoroacetate salt | 1.99 | 377.6 |
| 1-10 | | 3-[(1S)-1-phenylethyl]-5,6,7,8,9,10-hexahydro[1,2,4]triazolo[4,3-α]azocine trifluoroacetate salt | 1.37 | 255.4 |
| 1-11 | | 3-[(1S)-1-phenylpropyl]-5,6,7,8,9,10-hexahydro[1,2,4]triazolo[4,3-α]azocine trifluoroacetate salt | 1.48 | 269.4 |

-continued

| Cpd | Structure (parent) | Name | Retention Time (min) | MS ESI (m/z) |
|---|---|---|---|---|
| 1-12 | | 3-[1-(2-fluoro-1,1'-biphenyl-4-yl)ethyl]-5,6,7,8,9,10-hexahydro[1,2,4]triazolo[4,3-α]azocine trifluoroacetate salt | 1.83 | 349.5 |
| 1-13 | | 3-[(1S)-1-(2-fluoro-1,1'-biphenyl-4-yl)ethyl]-5,6,7,8,9,10-hexahydro[1,2,4]triazolo[4,3-α]azocine trifluoroacetate salt | 1.82 | 349.5 |
| 1-14 | | 3-[(1S)-1-(4-isobutylphenyl)ethyl]-5,6,7,8,9,10-hexahydro[1,2,4]triazolo[4,3-α]azocine trifluoroacetate salt | 1.91 | 311.5 |
| 1-15 | | 3-[(1R)-1-phenylethyl]-5,6,7,8,9,10-hexahydro[1,2,4]triazolo[4,3-α]azocine trifluoroacetate salt | 1.37 | 255.4 |
| 1-16 | | 3-[(1R)-1-phenylpropyl]-5,6,7,8,9,10-hexahydro[1,2,4]triazolo[4,3-α]azocine trifluoroacetate salt | 1.51 | 269.4 |

EXAMPLE 2

Procedure 2A

General Scheme

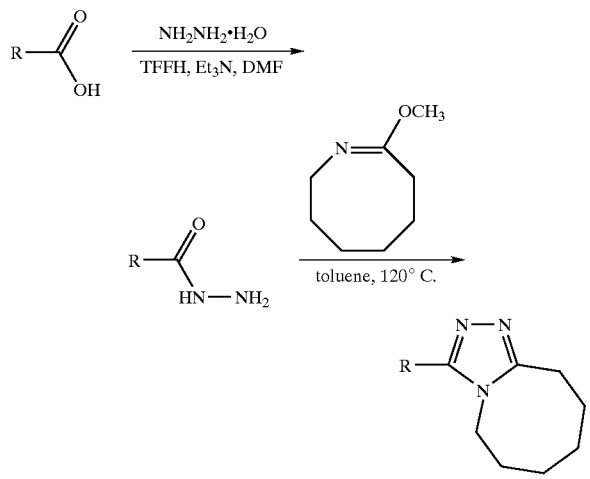

Preparation of 3-Trityl-5,6,7,8,9,10-hexahydro[1,2,4]triazolo[4,3-α]azocine (2-1)

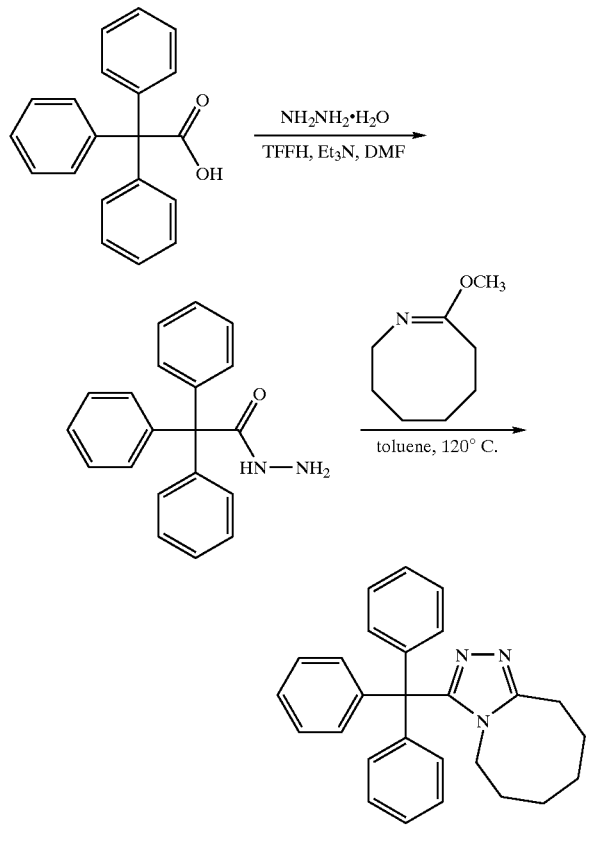

Triphenylacetic acid (499.6 mg, 1.73 mmol) was dissolved in N,N-dimethylformamide (DMF, 3.46 mL). Fluoro-N,N,N',N'-tetramethylformamidinium hexafluorophosphate (TFFH, 460.1 mg, 1.742 mmol) and anhydrous triethylamine (480 μl, 3.44 mmol) were added and the solution was cooled to 0° C. After 10 minutes hydrazine monohydrate (168 μl, 3.46 mmol) was added. The reaction was allowed to warm, and after stirring at room temperature for 30 minutes, it was worked up by adding water and filtering the resulting precipitate. The precipitate was dried under vacuum to give 2,2,2-triphenylacetohydrazide (340.1 mg).

2,2,2-Triphenylacetohydrazide (48.2 mg, 0.159 mmol) was dissolved in anhydrous toluene (3 mL) and stirred at room temperature under nitrogen. 8-Methoxy-2,3,4,5,6,7-hexahydroazocine (24.7 mg, 0.175 mmole) was added and the solution was stirred at 120° C. overnight and 200° C. for two days. After cooling, the toluene was removed by evaporation and crude product was purified by silica gel chromatography (100% ethyl acetate→5% methanol in ethyl acetate→10% methanol in ethyl acetate) to give the product (2-1) as a white solid (12.4 mg).

Compounds 2-2, 2-3, 2-4 and 2-5 were prepared by essentially the same procedure using the appropriate carboxylic acid, except that the final triazole-forming reaction was usually complete after stirring at 120° C. overnight (monitored by HPLC/MS). The acyl hydrazide of compound 2-5 did not precipitate, so the DMF and water were removed under vacuum.

| S.M. for: | Starting Material R—COOH |
|---|---|
| 2-1 | (triphenylacetic acid structure) |
| 2-2 | (1-(p-tolyl)cyclohexanecarboxylic acid structure) |
| 2-3 | (1-(4-chlorophenyl)cyclohexanecarboxylic acid structure) |
| 2-4 | (2,2-diphenylpropanoic acid structure) |

-continued

| S.M. for: | Starting Material R—COOH |
|---|---|
| 2-5 | 4-F-C6H4-C(cyclohexyl)(COOH) |

| Cpd | Structure (parent) | Name | Retention Time (min) | MS ESI (m/z) |
|---|---|---|---|---|
| 2-1 | | 3-trityl-5,6,7,8,9,10-hexahydro[1,2,4]triazolo[4,3-α]azocine | 2.98 | 394.3 |
| 2-2 | | 3-[1-(4-methylphenyl)cyclohexyl]-5,6,7,8,9,10-hexahydro[1,2,4]triazolo[4,3-α]azocine | 2.68 | 324.3 |
| 2-3 | | 3-[1-(4-chlorophenyl)cyclohexyl]-5,6,7,8,9,10-hexahydro[1,2,4]triazolo[4,3-α]azocine | 2.71 | 344.2 |
| 2-4 | | 3-(1,1-diphenylethyl)-5,6,7,8,9,10-hexahydro[1,2,4]triazolo[4,3-α]azocine | 2.72 | 332.2 |

| Cpd | Structure (parent) | Name | Retention Time (min) | MS ESI (m/z) |
|---|---|---|---|---|
| 2-5 | 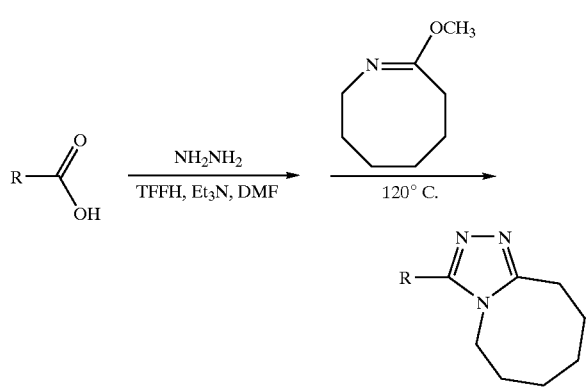 | 3-[1-(4-fluorophenyl)cyclohexyl]-5,6,7,8,9,10-hexahydro[1,2,4]triazolo[4,3-α]azocine | 2.54 | 328.3 |

Procedure 2B

General Scheme

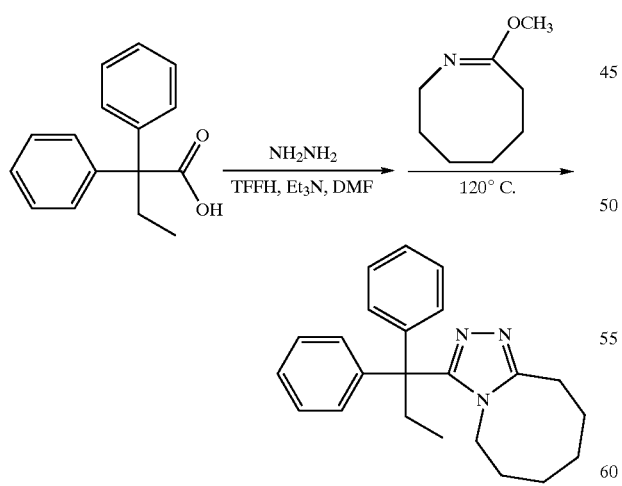

Preparation of 3-(1,1-Diphenylpropyl)-5,6,7,8,9,10-hexahydro[1,2,4]triazolo[4,3-α]azocine (2-6)

2,2-Diphenylbutanoic acid (39.6 mg, 0.166 mmol) was dissolved in DMF (0.33 mL). Fluoro-N,N,N',N'-tetramethylformamidinium hexafluorophosphate (TFFH, 43.6 mg) and anhydrous triethylamine (46.4 μl) were added and the solution was cooled to 0° C. After 10 minutes, hydrazine monohydrate (6.5 μL) was added. After stirring at room temperature for 30 minutes, HPLC/MS showed complete conversion to 2,2-diphenylbutanohydrazide. 8-Methoxy-2,3,4,5,6,7-hexahydroazocine (38 μL, 0.249 mmole, 1.6 eq.) was added, and the solution was stirred at 120° C. overnight. After warming to room temperature, the product was purified by preparative HPLC and isolated as the trifluoroacetate salt. The salt was added to a saturated sodium bicarbonate solution and extracted with ethyl acetate to give the freebase. The extract was dried over magnesium sulfate, filtered and concentrated to give the purified triazole (2-6) as a white solid (29.5 mg).

Compounds 2-7 to 2-33, 2-49 and 2-50 were prepared by essentially the same procedure using the appropriate carboxylic acid S.M. Product formation was monitored by HPLC/MS. The duration of the hydrazide-forming reaction was changed for 2-11 (1 hour), 2-13 (overnight), 2-14 (2 hours). The duration of the triazole-forming reaction was changed for 2-22 (2 hours), 2-25 (3 hours), 2-31 (overnight at 120° C. and 4 hours at 180° C.), 2-33 (3 hours), and 249 (1.5 hours).

| S.M. for: | Starting Material R—COOH |
|---|---|
| 2-6 | |
| 2-7 | |

-continued

| S.M. for: | Starting Material R—COOH |
|---|---|
| 2-8 | 2-phenyl-2-methylbutanoic acid |
| 2-9 | 8-phenyl-1,4-dioxaspiro[4.5]decane-8-carboxylic acid |
| 2-10 | 2-(4-cyclohexylphenyl)-2-methylpropanoic acid |
| 2-11 | 1-(naphthalen-1-yl)cyclobutanecarboxylic acid |
| 2-12 | 1-(tert-butoxycarbonyl)-4-phenylpiperidine-4-carboxylic acid |
| 2-13 | 1-phenylcyclopropanecarboxylic acid |
| 2-14 | 1-(2-fluorophenyl)cyclopentanecarboxylic acid |

-continued

| S.M. for: | Starting Material R—COOH |
|---|---|
| 2-15 | 1-phenylcyclopentanecarboxylic acid |
| 2-16 | 3-methyl-2-phenylbutanoic acid |
| 2-17 | 2-methyl-2-phenylpropanoic acid |
| 2-18 | 2-cyclopentyl-2-phenylacetic acid |
| 2-19 | 1-phenylcyclobutanecarboxylic acid |
| 2-20 | 2-phenyl-2-butenoic acid |
| 2-21 | 1-(4-methylphenyl)cyclopropanecarboxylic acid |
| 2-22 | 2-(4-methylphenyl)-3-methylbutanoic acid |
| 2-23 | 2-(4-fluorophenyl)-3-methylbutanoic acid |

-continued

| S.M. for: | Starting Material R—COOH |
|---|---|
| 2-24 | 2-phenyl-2-cyclobutyl propanoic acid (α-methyl, α-cyclobutyl phenylacetic acid) |
| 2-25 | 1-(3-methylphenyl)cyclopentane-1-carboxylic acid |
| 2-26 | 1-(4-chlorophenyl)cyclobutane-1-carboxylic acid |
| 2-27 | 1-(4-methylphenyl)cyclopentane-1-carboxylic acid |
| 2-28 | 1-(4-fluorophenyl)cyclopentane-1-carboxylic acid |
| 2-29 | 1-phenyl-2-methylcyclobutane-1-carboxylic acid |

-continued

| S.M. for: | Starting Material R—COOH |
|---|---|
| 2-30 | 1-phenyl-2-vinylcyclopropane-1-carboxylic acid |
| 2-31 | 1-(3-hydroxyphenyl)cyclopentane-1-carboxylic acid |
| 2-32 | 2-(4-chlorophenyl)-2-methylpropanoic acid |
| 2-33 | 2-(3-hydroxyphenyl)-2-methylpropanoic acid |
| 2-49 | 1-(4-chlorophenyl)cyclopropane-1-carboxylic acid |
| 2-50 | 1-(2,4-dichlorophenyl)cyclopropane-1-carboxylic acid |

| Cpd | Structure (parent) | Name | Retention Time (min) | MS ESI (m/z) |
|---|---|---|---|---|
| 2-6 | | 3-(1,1-diphenylpropyl)-5,6,7,8,9,10-hexahydro[1,2,4]triazolo[4,3-α]azocine | 2.77 | 346.3 |
| 2-7 | | 3-(1,1-diphenylhexyl)-5,6,7,8,9,10-hexahydro[1,2,4]triazolo[4,3-α]azocine | 3.31 | 388.3 |
| 2-8 | | (3-(1-methyl-1-phenylpropyl)-5,6,7,8,9,10-hexahydro[1,2,4]triazolo[4,3-α]azocine | 2.24 | 284.3 |
| 2-9 | | 3-(8-phenyl-1,4-dioxaspiro[4.5]dec-8-yl)-5,6,7,8,9,10-hexahydro[1,2,4]triazolo[4,3-α]azocine | 2.22 | 368.2 |
| 2-10 | | 3-[1-(4-cyclohexylphenyl)-1-methylethyl]-5,6,7,8,9,10-hexahydro[1,2,4]triazolo[4,3-α]azocine | 3.16 | 352.3 |

-continued
| Cpd | Structure (parent) | Name | Retention Time (min) | MS ESI (m/z) |
|---|---|---|---|---|
| 2-11 | 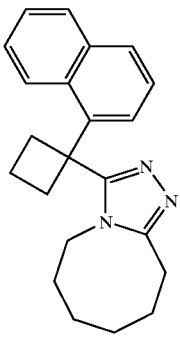 | 3-[1-(1-naphthyl)cyclobutyl]-5,6,7,8,9,10-hexahydro[1,2,4]triazolo[4,3-α]azocine | 2.51 | 332.3 |
| 2-12 | 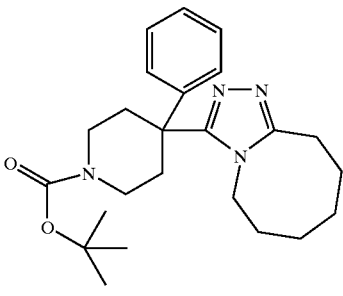 | tert-butyl 4-(5,6,7,8,9,10-hexahydro[1,2,4]triazolo[4,3-α]azocin-3-yl)-4-phenylpiperidine-1-carboxylate | 2.58 | 355.2 |
| 2-13 | 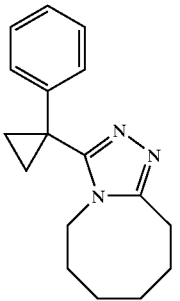 | 3-(1-phenylcyclopropyl)-5,6,7,8,9,10-hexahydro[1,2,4]triazolo[4,3-α]azocine | 1.91 | 268.2 |
| 2-14 | 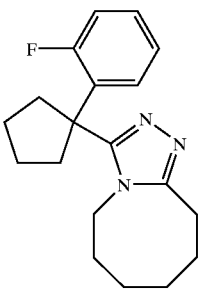 | 3-[1-(2-fluorophenyl)cyclopentyl]-5,6,7,8,9,10-hexahydro[1,2,4]triazolo[4,3-α]azocine | 2.15 | 314.2 |
| 2-15 | 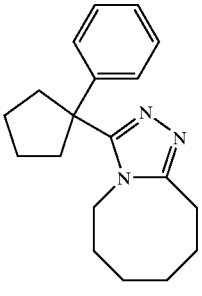 | 3-(1-phenylcyclopentyl)-5,6,7,8,9,10-hexahydro[1,2,4]triazolo[4,3-α]azocine | 2.29 | 296.3 |

-continued
| Cpd | Structure (parent) | Name | Retention Time (min) | MS ESI (m/z) |
|---|---|---|---|---|
| 2-16 | 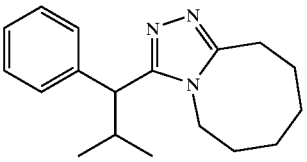 | 3-(2-methyl-1-phenylpropyl)-5,6,7,8,9,10-hexahydro[1,2,4]triazolo[4,3-α]azocine | 2.23 | 284.2 |
| 2-17 | 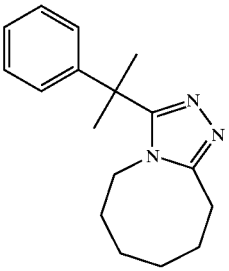 | 3-(1-methyl-1-phenylethyl)-5,6,7,8,9,10-hexahydro[1,2,4]triazolo[4,3-α]azocine | 1.97 | 270.3 |
| 2-18 | 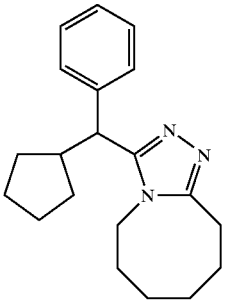 | 3-[cyclopentyl(phenyl)methyl]-5,6,7,8,9,10-hexahydro[1,2,4]triazolo[4,3-α]azocine | 2.47 | 310.3 |
| 2-19 | 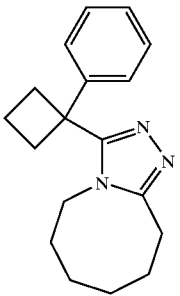 | 3-(1-phenylcyclobutyl)-5,6,7,8,9,10-hexahydro[1,2,4]triazolo[4,3-α]azocine | 2.13 | 282.3 |
| 2-20 | 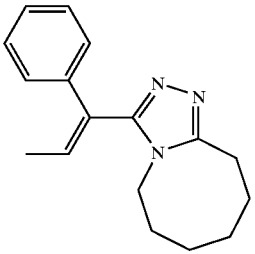 | 3-[(1E)-1-phenylprop-1-enyl]-5,6,7,8,9,10-hexahydro[1,2,4]triazolo[4,3-α]azocine | 2.02 | 268.2 |

-continued

| Cpd | Structure (parent) | Name | Retention Time (min) | MS ESI (m/z) |
|---|---|---|---|---|
| 2-21 | | 3-[1-(4-methylphenyl)cyclopropyl]-5,6,7,8,9,10-hexahydro[1,2,4]triazolo[4,3-α]azocine | 2.21 | 282.2 |
| 2-22 | | 3-[2-methyl-1-(4-methylphenyl)propyl]-5,6,7,8,9,10-hexahydro[1,2,4]triazolo[4,3-α]azocine | 2.49 | 298.3 |
| 2-23 | | 3-[1-(4-fluorophenyl)-2-methylpropyl]-5,6,7,8,9,10-hexahydro[1,2,4]triazolo[4,3-α]azocine | 2.35 | 302.3 |
| 2-24 | | 3-(1-cyclobutyl-1-phenylethyl)-5,6,7,8,9,10-hexahydro[1,2,4]triazolo[4,3-α]azocine | 2.54 | 310.3 |
| 2-25 | | 3-[1-(3-methylphenyl)cyclopentyl]-5,6,7,8,9,10-hexahydro[1,2,4]triazolo[4,3-α]azocine | 2.53 | 310.2 |
| 2-26 | | 3-[1-(4-chlorophenyl)cyclobutyl]-5,6,7,8,9,10-hexahydro[1,2,4]triazolo[4,3-α]azocine | 2.47 | 316.2 |

-continued

| Cpd | Structure (parent) | Name | Retention Time (min) | MS ESI (m/z) |
|---|---|---|---|---|
| 2-27 | | 3-[1-(4-methylphenyl)cyclopentyl]-5,6,7,8,9,10-hexahydro[1,2,4]triazolo[4,3-α]azocine | 2.53 | 310.2 |
| 2-28 | | 3-[1-(4-fluorophenyl)cyclopentyl]-5,6,7,8,9,10-hexahydro[1,2,4]triazolo[4,3-α]azocine | 2.45 | 314.2 |
| 2-29 | | 3-(2-methyl-1-phenylcyclobutyl)-5,6,7,8,9,10-hexahydro[1,2,4]triazolo[4,3-α]azocine | 2.27 | 296.2 |
| 2-30 | | 3-(1-phenyl-2-vinylcyclopropyl)-5,6,7,8,9,10-hexahydro[1,2,4]triazolo[4,3-α]azocine | 2.25 | 294.2 |
| 2-31 | | 3-[1-(5,6,7,8,9,10-hexahydro[1,2,4]triazolo[4,3-α]azocin-3-yl)cyclopentyl]phenol | 1.91 | 312.2 |

-continued
| Cpd | Structure (parent) | Name | Retention Time (min) | MS ESI (m/z) |
|---|---|---|---|---|
| 2-32 | | 3-[1-(4-chlorophenyl)-1-methylethyl]-5,6,7,8,9,10-hexahydro[1,2,4]triazolo[4,3-α]azocine | 2.09 | 304.2 |
| 2-33 | | 3-[1-(5,6,7,8,9,10-hexahydro[1,2,4]triazolo[4,3-α]azocin-3-yl)-1-methylethyl]phenol | 1.63 | 286.2 |
| 2-49 | | 3-[1-(4-chlorophenyl)cyclopropyl]-5,6,7,8,9,10-hexahydro[1,2,4]triazolo[4,3-α]azocine | 2.25 | 302.2 |
| 2-50 | | 3-[1-(2,4-dichlorophenyl)cyclopropyl]-5,6,7,8,9,10-hexahydro[1,2,4]triazolo[4,3-α]azocine | 2.32 | 336.2 |
Procedure 2C
General Scheme
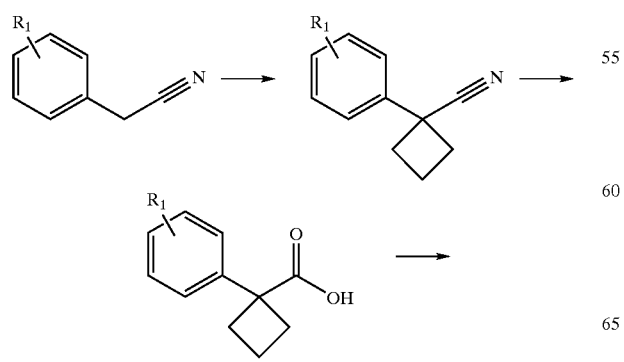
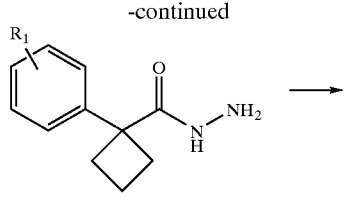
-continued
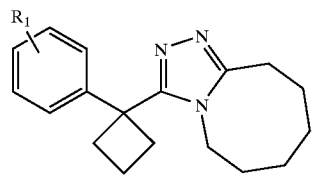

Preparation of 3-[1-(2-Fluorophenyl)cyclobutyl]-5,6,7,8,9,10-hexahydro[1,2,4]triazolo[4,3-α]azocine (2-34)

Part 1

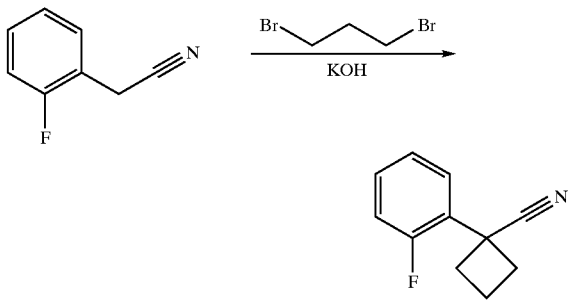

Potassium hydroxide (1.78 g) was dissolved in dimethyl sulfoxide (5.8 mL) [1]. (2-Fluorophenyl)acetonitrile (0.97 g, 7.2 mmol) and 1,3-dibromopropane (0.95 mL, 9.3 mmol) were dissolved in ethyl ether (2 mL), and this mixture was added dropwise to the potassium hydroxide solution while vigorously stirring at room temperature. Reaction color change was observed (colorless to yellow to orange). After stirring at room temperature for one hour, the reaction was quenched by adding ice-cold water (3.8 mL). The mixture was filtered through a pad of celite which was washed with ether (20 mL). The filtrate was added to a separatory funnel, and the aqueous layer was extracted with ether (3×10 mL). The organic layers were combined, dried over magnesium sulfate, filtered, and concentrated to give a light yellow oil (1.0 g). Pure 1-(2-Fluorophenyl)cyclobutanecarbonitrile (0.45 g) was obtained after silica gel chromatography.

Part 2

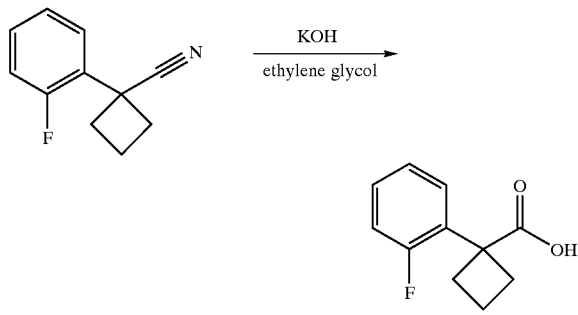

1-(2-Fluorophenyl)cyclobutanecarbonitrile (0.21 g, 1.15 mmole, 1 eq.) and potassium hydroxide (0.194 g, 3 eq.) were dissolved in ethylene glycol (2 mL). After refluxing for three hours at 198° C., the reaction mixture was poured into water (5 mL) and extracted with ether (2×5 mL). The aqueous solution was acidified with HCl and extracted with ether (3×5 mL). The extracts were combined, dried over magnesium sulfate, filtered and concentrated to provide the crude carboxylic acid.

Part 3

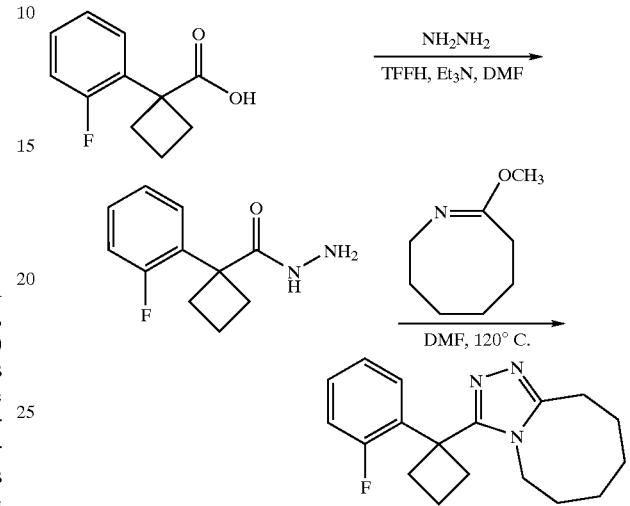

1-(2-Fluorophenyl)cyclobutanecarboxylic acid (51.3 mg, 0.264 mmol) was dissolved in DMF (0.52 mL). Fluoro-N,N,N',N'-tetramethylformamidinium hexafluorophosphate (TFFH, 74.6 mg, 0.282 mmol) and anhydrous triethylamine (71.0 μL, 0.509 mmol) were added at room temperature. After 5 minutes, anhydrous hydrazine (10 μl, 0.319 mmol) was added. After stirring at room temperature for 30 minutes, HPLC-MS showed the formation of 1-(2-fluorophenyl)cyclobutanecarbohydrazide in good yield.

8-Methoxy-2,3,4,5,6,7-hexahydroazocine (47 μl, 0.412 mmol) was added to the solution of 1-(2-fluorophenyl)cyclobutanecarbohydrazide, and the reaction was stirred at 120° C. overnight. After cooling, the solution was concentrated, and the product was purified by preparative HPLC as the trifluoroacetate salt. The salt was added to a saturated sodium bicarbonate solution and extracted with ethyl acetate to give the freebase. The extract was dried over magnesium sulfate, filtered and evaporated to give the purified triazole (2-34) as a solid (12.5 mg).

Compounds 2-35 to 2-42 were prepared by essentially the same procedure using the appropriate phenyl acetonitrile. Product formation was monitored by HPLC/MS. The duration of the triazole-forming reaction was changed for 2-42 (3 hours).

-continued
| | | | | Retention Time (min) | MS ESI (m/z) |
|---|---|---|---|---|---|
| 2-34 | 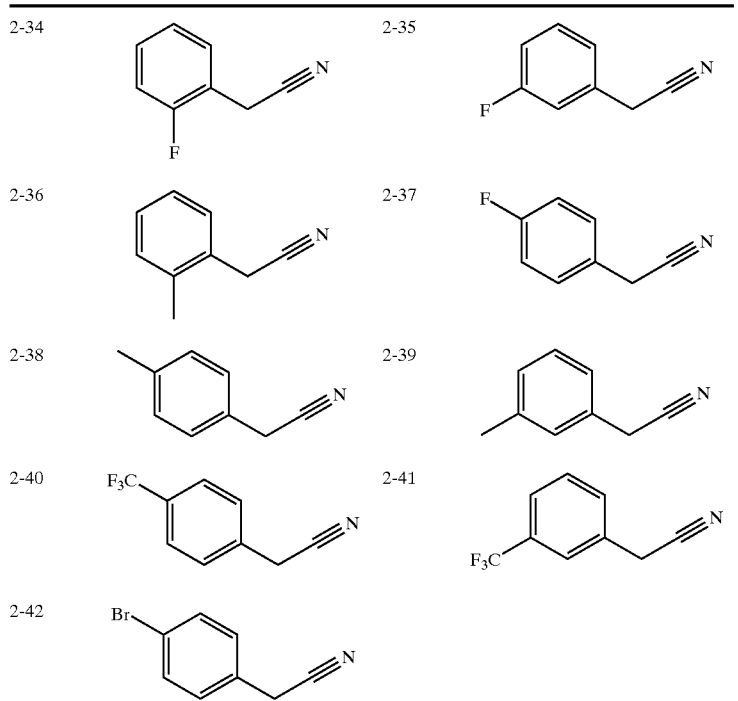 | | | | |
| 2-35 | | | | | |
| 2-36 | | | | | |
| 2-37 | | | | | |
| 2-38 | | | | | |
| 2-39 | | | | | |
| 2-40 | | | | | |
| 2-41 | | | | | |
| 2-42 | | | | | |
| Cpd | Structure | Name | Retention Time (min) | MS ESI (m/z) |
|---|---|---|---|---|
| 2-34 | 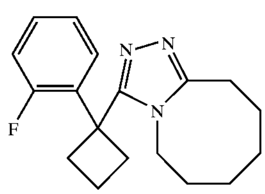 | 3-[1-(2-fluorophenyl)cyclobutyl]-5,6,7,8,9,10-hexahydro[1,2,4]triazolo[4,3-a]azocine | 2.10 | 300.2 |
| 2-35 | 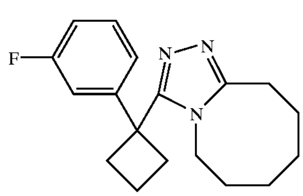 | 3-[1-(3-fluorophenyl)cyclobutyl]-5,6,7,8,9,10-hexahydro[1,2,4]triazolo[4,3-a]azocine | 2.24 | 300.2 |
| 2-36 | 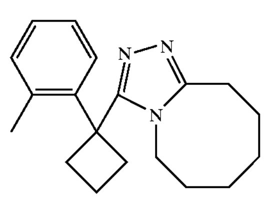 | 3-[1-(2-methylphenyl)cyclobutyl]-5,6,7,8,9,10-hexahydro[1,2,4]triazolo[4,3-a]azocine | 2.32 | 296.2 |
| 2-37 | 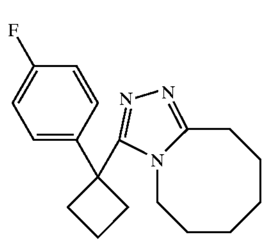 | 3-[1-(4-fluorophenyl)cyclobutyl]-5,6,7,8,9,10-hexahydro[1,2,4]triazolo[4,3-a]azocine | 2.26 | 300.2 |

-continued

| | | | | |
|---|---|---|---|---|
| 2-38 | | 3-[1-(4-methylphenyl)cyclobutyl]-5,6,7,8,9,10-hexahydro[1,2,4]triazolo[4,3-a]azocine | 2.44 | 296.2 |
| 2-39 | | 3-[1-(3-methylphenyl)cyclobutyl]-5,6,7,8,9,10-hexahydro[1,2,4]triazolo[4,3-a]azocine | 2.45 | 296.2 |
| 2-40 | | 3-{1-[4-(trifluoromethyl)phenyl]cyclobutyl}-5,6,7,8,9,10-hexahydro[1,2,4]triazolo[4,3-a]azocine | 2.62 | 350.3 |
| 2-41 | | 3-{1-[2-(trifluoromethyl)phenyl]cyclobutyl}-5,6,7,8,9,10-hexahydro[1,2,4]triazolo[4,3-a]azocine | 2.29 | 350.3 |
| 2-42 | | 3-[1-(4-bromophenyl)cyclobutyl]-5,6,7,8,9,10-hexahydro[1,2,4]triazolo[4,3-a]azocine | 2.50 | 360.2 |

Procedure 2D

General Scheme

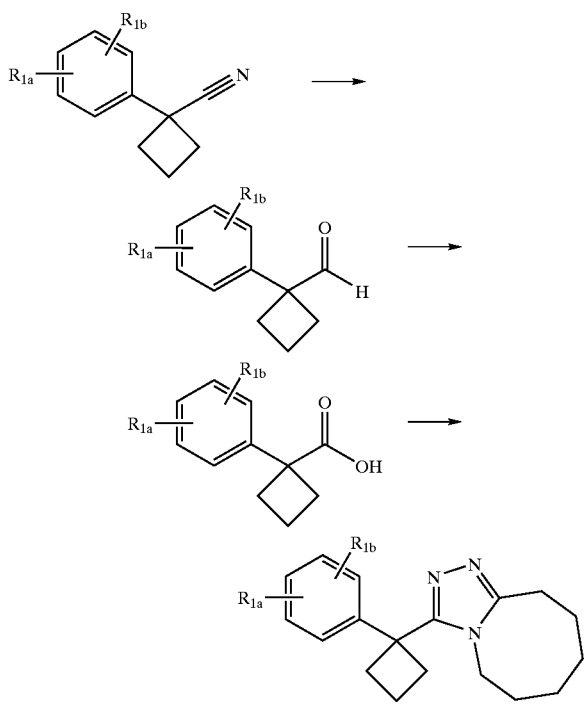

Preparation of 3-[1-(3,4-Difluorophenyl)
cyclobutyl]-5,6,7,8,9,10-hexahydro[1,2,4]triazolo[4,
3-a]azocine(2-43)

Part 1

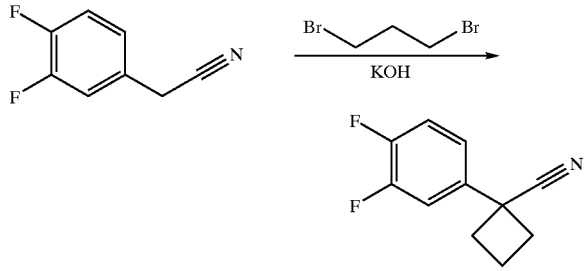

(3,4-Difluorophenyl)acetonitrile was converted to 1-(3,4-Difluorophenyl)cyclobutanecarbonitrile following the method described in Procedure 2C, Part 1.

Part 2

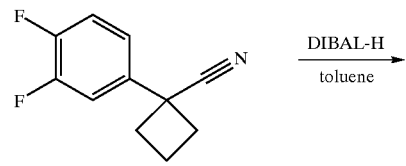

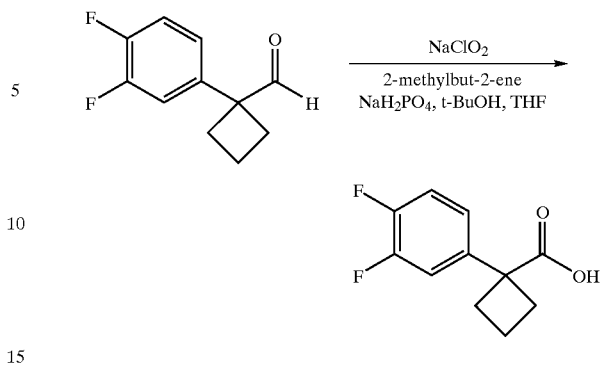

1-(3,4-Difluorophenyl)cyclobutanecarbonitrile (384.5 mg, 1.99 mmol) was dissolved in toluene (30 mL), and cooled to −78° C. Diisobutylaluminum hydride (DEBAL-H) (1.0 M solution in hexanes) (3.98 mL, 3.98 mmol) was added dropwise. The reaction was monitored by TLC (hexanes:ethyl acetate, 9:1). After stirring at −78° C. for 30 minutes, 5% sulfuric acid (2 mL) was added. The reaction was warmed to room temperature, stirred for 20 minutes, and filtered through a pad of celite. The pad was washed with ethyl acetate, and the entire filtrate was added to a separatory funnel and washed with water. The organic layer was dried over sodium sulfate and concentrated to give the desired aldehyde.

1-(3,4-Difluorophenyl)cyclobutanecarbaldehyde (240.0 mg, 1.22 mmol) was dissolved in tert-butanol/tetrahydrofuran/2-methylbut-2-ene (3.0 mL/1.0 mL/1.0 mL) and stirred vigorously at room temperature. Sodium chlorite (243.4 mg, 2.69 mmol) and sodium dihydrogenphosphate (370.4 mg, 2.68 mmol) were dissolved in water (1.2 mL) and added dropwise to the above solution. After stirring for one hour, TLC showed the reaction was complete. The volatile solvents were removed under vacuum and the product was diluted with water then washed with hexane (3 mL). The aqueous solution was acidified with 6 N aqueous hydrochloric acid to pH 2. After extraction with ethyl acetate (3×20 mL), the combined organic layers were washed with brine (5 mL), dried over magnesium sulfate, filtered, and concentrated to provide the desired carboxylic acid (125 mg).

Part 3

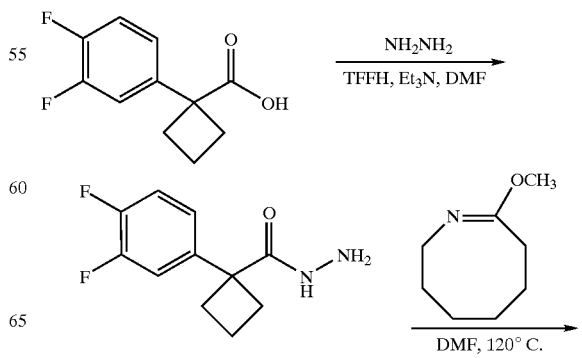

-continued

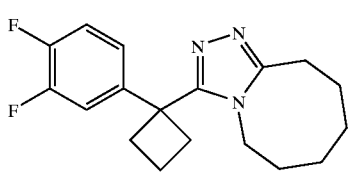

1-(3,4-Difluorophenyl)cyclobutanecarboxylic acid was converted to of 3-[1-(3,4-difluorophenyl)cyclobutyl]-5,6,7,8,9,10-hexahydro[1,2,4]triazolo[4,3-α]azocine (2-43) following the method described in Procedure 2C, Part 3.

Compounds 2-44 to 2-48 were prepared by essentially the same procedure using the appropriate disubstituted phenylacetonitrile. Product formation was monitored by HPLC/MS.

| S.M. for: | Starting Material | S.M. for: | Starting Material |
|---|---|---|---|
| 2-43 | 3,4-difluoro (F at 3,4) | 2-44 | 2,4-difluoro |
| 2-45 | 2,4-dichloro | 2-46 | 3,4-dichloro |
| 2-47 | 2-Cl, 4-F | 2-48 | 2-Cl, 3-CF$_3$ |

| Cpd | Structure | Name | Retention Time (min) | MS ESI (m/z) |
|---|---|---|---|---|
| 2-43 | 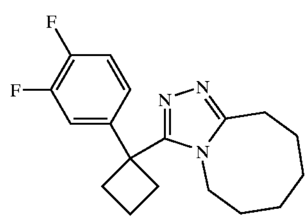 | 3-[1-(3,4-difluorophenyl)cyclobutyl]-5,6,7,8,9,10-hexahydro[1,2,4]triazolo[4,3-a]azocine | 2.31 | 318.2 |
| 2-44 | 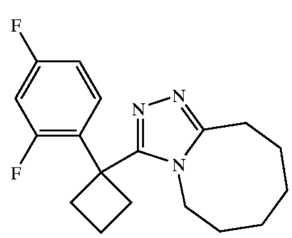 | 3-[1-(2,4-difluorophenyl)cyclobutyl]-5,6,7,8,9,10-hexahydro[1,2,4]triazolo[4,3-a]azocine | 2.16 | 318.2 |

| | | | | |
|---|---|---|---|---|
| 2-45 | 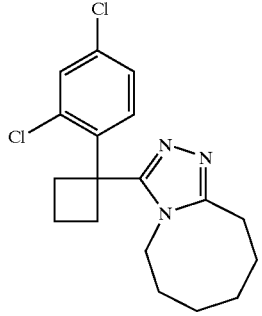 | 3-[1-(2,4-dichlorophenyl)cyclobutyl]-5,6,7,8,9,10-hexahydro[1,2,4]triazolo[4,3-a]azocine | 2.51 | 350.1 |
| 2-46 | 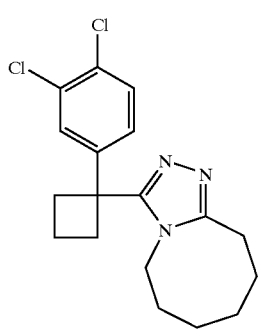 | 3-[1-(3,4-dichlorophenyl)cyclobutyl]-5,6,7,8,9,10-hexahydro[1,2,4]triazolo[4,3-a]azocine | 2.65 | 350.1 |
| 2-47 | 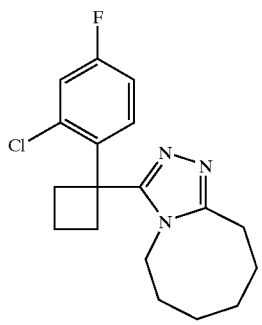 | 3-[1-(2-chloro-4-fluorophenyl)cyclobutyl]-5,6,7,8,9,10-hexahydro[1,2,4]triazolo[4,3-a]azocine | 2.29 | 334.2 |
| 2-48 | 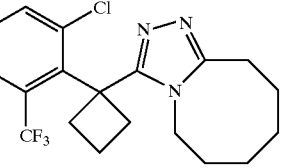 | 3-{1-[2-chloro-6-(trifluoromethyl)phenyl]cyclobutyl}-5,6,7,8,9,10-hexahydro[1,2,4]triazolo[4,3-a]azocine | 2.56 | 384.2 |

Procedure 2E

General Scheme

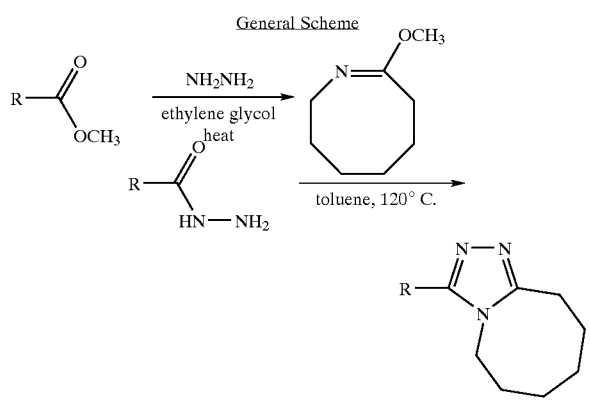

Preparation of 3-(1-Phenylcyclohexyl)-5,6,7,8,9,10-hexahydro[1,2,4]triazolo[4,3-α]azocine (3-51)

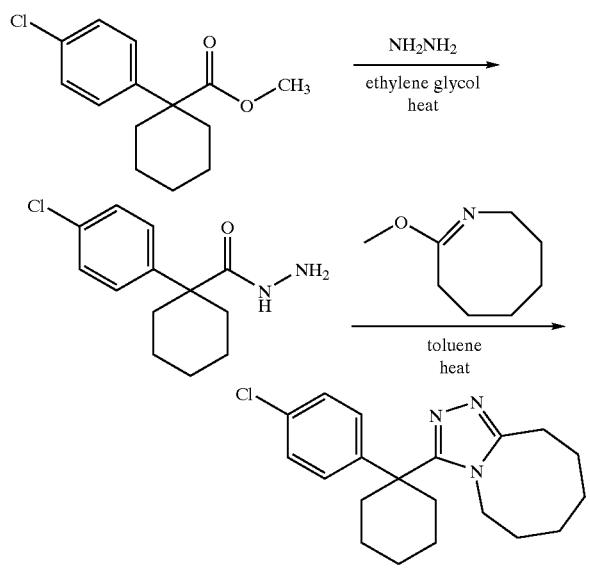

Methyl 1-(4-chlorophenyl)cyclohexanecarboxylate (277 mg) and hydrazine hydrate (0.30 mL) were dissolved in ethylene glycol (5 mL) and heated to 150° C. for 15 hours. The solution was cooled and water was added (5 mL). The resulting precipitate was collected by filtration and dried under vacuum to give the acyl hydrazide (108 mg) as a white solid.

Anhydrous toluene was added to a mixture of 1-(4-chlorophenyl)cyclohexanecarbohydrazide (62 mg) and 8-methoxy-2,3,4,5,6,7-hexahydroazocine (40.1 mg). The reaction vessel was heated to 120° C. overnight, whereupon it was cooled to room temperature and the solvent was evaporated. The crude product was purified by column chromatography to give 3-(1-phenylcyclohexyl)-5,6,7,8,9,10-hexahydro[1,2,4]triazolo[4,3-α]azocine (2-51) as a white solid.

3-Benzhydryl-6,7,8,9-tetrahydro-5H-[1,2,4]triazolo[4,3-α]azepine (2-52) was prepared by essentially the same procedure starting with methyl diphenylacetate.

Preparative LC Method for Example 2:

| | |
|---|---|
| Column: | YMC - PACK ODS, 100 mm × 20 mm, 5.0 μm |
| Eluent A: | 0.05% TFA in Water |
| Eluent B: | 0.05% TFA in Acetonitrile |
| Pre-inject Equilibration: | 1.0 min |
| Post-Inject Hold: | 1.0 min |
| Gradient: | 10% B to 100% B: Between 1 and 16 minutes ramp to 50% B; between 16 and 21 minutes ramp to 100% B and hold at 100% B for 2 minutes; ramp back from 100% B to 10% B over 1 minute. |
| Flow: | 20 mL/min. |
| Column Temperature: | ambient |
| Injection amount: | 5.0 ml |
| Detection: | photodiode array |

Analytical LC Method for Example 2:

| | |
|---|---|
| Column: | Waters- XTerra C18, 5μm, 4.6 × 50 mm |
| Eluent A: | 0.60% TFA in Water |
| Eluent B: | 0.50% TFA in Acetonitrile |
| Gradient: | 10% B to 90% B in 4.5 minutes, hold for 0.5 minute, ramp back to 10% B in 0.5 min |
| Flow: | 2.5 mL/min (going into the MS = 250 μl) |
| Column Temperature: | 30° C. |
| Injection amount: | 10 μL of undiluted crude reaction mixture. |
| Detection: | DAD: 190–600 nm. MS: API-ES positive ionization mode, Variable mass scan range: |

LC1–XLo = 50–500 amu
LC1–Low = 150–750 amu
LC1–Med = 300–1000 amu
LC1–High = 500–2000 amu

| S.M. for Cpd: | Starting Material R—CO₂Me | S.M. for: | Starting Material R—CO₂Me |
|---|---|---|---|

-continued

| Cpd | Structure | Name | Retention Time (min) | MS ESI (m/z) |
|---|---|---|---|---|
| 2-51 | 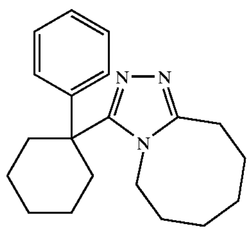 | 3-(1-phenylcyclohexyl)-5,6,7,8,9,10-hexahydro[1,2,4]triazolo[4,3-a]azocine | 2.53 | 310.2 |
| 2-52 | 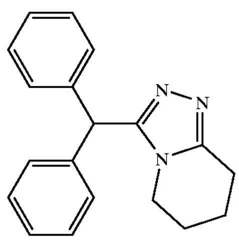 | 3-benzhydryl-6,7,8,9-tetrahydro-5H-[1,2,4]triazolo[4,3-a]azepine | 2.45 | 318.2 |

EXAMPLE 3

Procedure 3A

Preparation of 1-(4-Chlorophenyl)cyclobutanecarbohydrazide

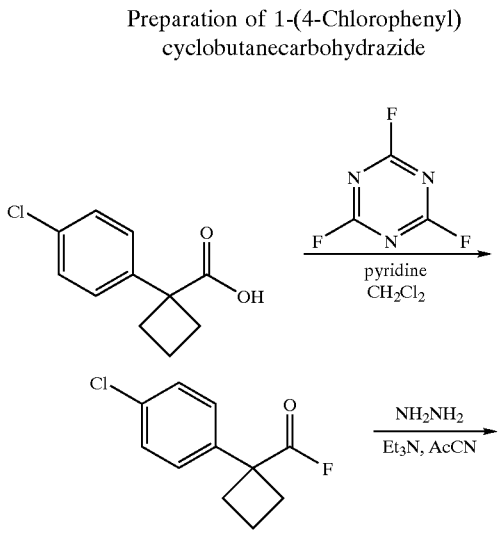

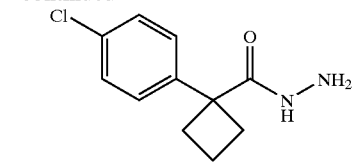

1-(4-Chlorophenyl)cyclobutane carboxylic acid (10.0 g) was dissolved in dichloromethane (150 mL) and cooled to −10° C. in an icelbrine bath. Pyridine (3.84 mL) was added followed by cyanuric fluoride (8.9 mL in 25 mL dichloromethane). After stirring at room temperature for one hour, TLC showed that the reaction was complete. The solution was added to a separatory funnel containing ice (150 mL). After vigorous shaking, the organic layer was removed, dried over magnesium sulfate, filtered and concentrated to give the carbonyl fluoride.

Anhydrous hydrazine (2.02 mL, 1.4 eq) was dissolved in acetonitrile (100 μL) and cooled to 0° C. Triethylamine (12.8 mL, 2.0 eq.) was added followed by 1-(4-chlorophenyl)cyclobutanecarbonyl fluoride (10 g, 1.0 eq) in acetonitrile (25 mL). After stirring at room temperature for one hour the acetonitrile was removed by evaporation. Product was obtained after silica gel chromatography.

Procedure 3B

Preparation of 1-(4-Chlorophenyl)cyclopropanecarbohydrazide

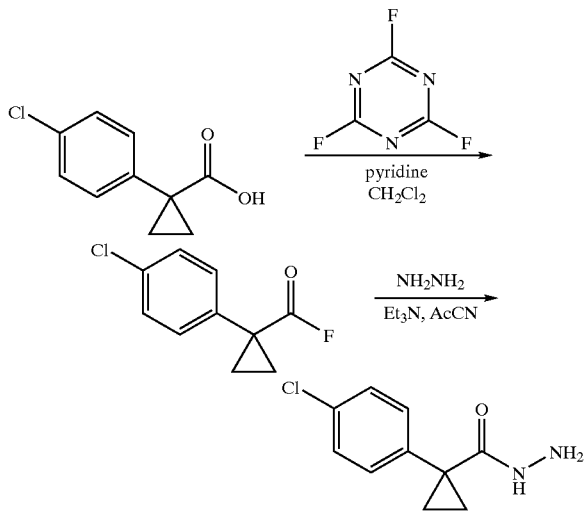

1-(4-Chlorophenyl)cyclopropanecarbohydrazide was made following Procedure 3A, using 1-(4-chlorophenyl)cyclopropanecarboxylic acid.

Procedure 3C

Preparation of 1-(4-Fluorophenyl)cyclobutanecarbohydrazide

Part 1

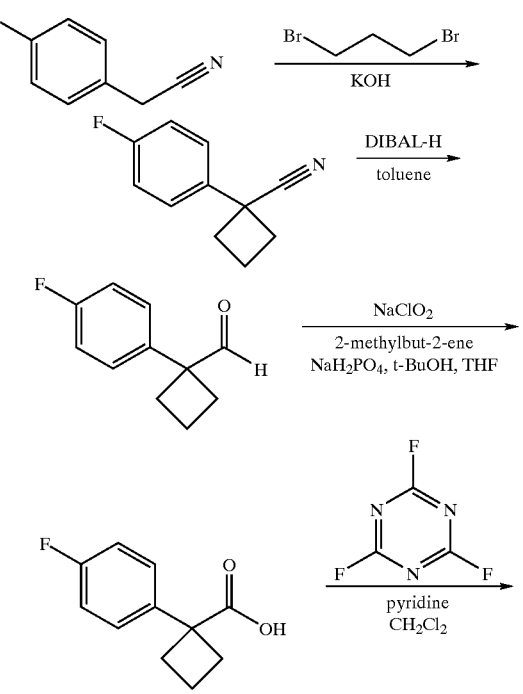

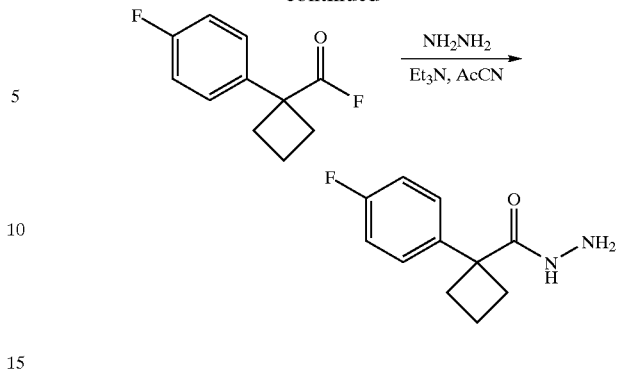

Potassium hydroxide (8.2 g, 146.1 mmol) was dissolved in dimethyl sulfoxide (100 mL) [1]. (4-Fluorophenyl)acetonitrile (6.87 g, 50.8 mmol) and 1,3-dibromopropane (5.4 mL, 53.3 mmol) were dissolved in ethyl ether (10 mL), and this mixture was added dropwise to the vigorously stirred potassium hydroxide solution at room temperature. Reaction color change was observed (colorless to yellow to orange). After stirring for two hours, the reaction was quenched by adding ice-cold water (10 mL). The mixture was filtered through a pad of celite which was washed with ether (100 mL). The filtrate was added to a separatory funnel, and the aqueous layer was extracted with ether (3×100 mL). The organic layers were combined, dried over magnesium sulfate, filtered and concentrated to provide the product (8.85 g) as a pale yellow oil.

Part 2

Crude 1-(4-Fluorophenyl)cyclobutanecarbonitrile (8.85 g, 50.5 mmol) was dissolved in anhydrous toluene (100 mL), and cooled to −78° C. Diisobutylaluminum hydride (DIBAL-H) (1.0 M solution in hexanes, 60.6 mL) was added dropwise. The reaction was monitored by TLC (Hexane:Ethyl acetate 9:1). After stirring at −78° C. for one hour, 5% sulfuric acid (20 mL) was added. The reaction was warmed to room temperature, stirred for 20 minutes, and filtered through a pad of celite. The pad was washed with ethyl acetate, and the entire filtrate was added to a separatory funnel and washed with water. The organic layer was dried over sodium sulfate, filtered and concentrated to dryness to give the desired aldehyde.

1-(4-Difluorophenyl)cyclobutanecarbaldehyde (8.8 g, 49.4 mmol) was dissolved in tert-butanol (90 mL), tetrahydrofuran (30 mL) and 2-methylbut-2-ene (30 ml) and stirred vigorously at room temperature. Sodium chlorite (9.8 g, 108.7 mmol) and sodium dihydrogenphosphate (15.0 g, 108.7 mmol) were dissolved in water (54 mL) and added dropwise to the above solution. After stirring for one hour, TLC showed the reaction was complete. The volatile solvents were removed under vacuum and the product was diluted with water then washed with hexane (3 mL). The aqueous solution was acidified with 6N aqueous hydrochloric acid to pH 2. After extraction with ethyl acetate (3×150 mL), the combined the organic layers were washed with brine (20 mL), dried over magnesium sulfate, filtered and concentrated to provide 1-(4-fluorophenylcarboxylic acid (8.0 g).

This carboxylic acid was converted to 1-(4-fluorophenyl)cyclobutanecarbohydrazide using Procedure 3A.

Procedure 3D

Preparation of 1-(4-Fuorophenyl)cyclopropanecarbohydrazide

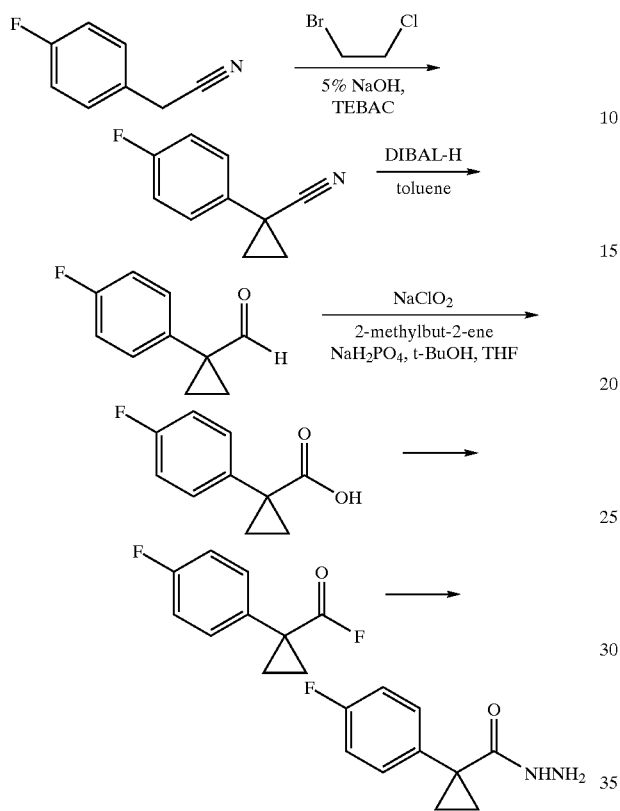

1-(4-Fluorophenyl)acetonitrile (3.77 g, 27.9 mmol), 1-bromo-2-chloroethane (5.0 g, 34.9 mmol) and benzyltriethylammonium chloride (TEBAC, 127.6 mg 0.56 mmol) were added to a flask and stirred vigorously [2]. Potassium hydroxide (50% in water, 195 mmol) was added dropwise. After stirring at 40° C. for 5 hours and then at room temperature overnight, the reaction was diluted with water and extracted with dichloromethane. The organic layer was collected, washed with IN aqueous hydrochloric acid, washed with water, and dried over magnesium sulfate. After filtration and evaporation of dichloromethane, the crude product (4.5 g) was obtained.

1-(4-fluorophenyl)cyclopropanecarboxylic acid was prepared from the crude 1-(4-fluorophenyl)cyclopropanecarbonitrile using the method described in Procedure 3C Part 2. This carboxylic acid was converted into 1-(4-fluorophenyl)cyclopropanecarbohydrazide), using Procedure 3A.

Procedure 3E

General Scheme

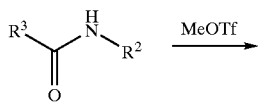

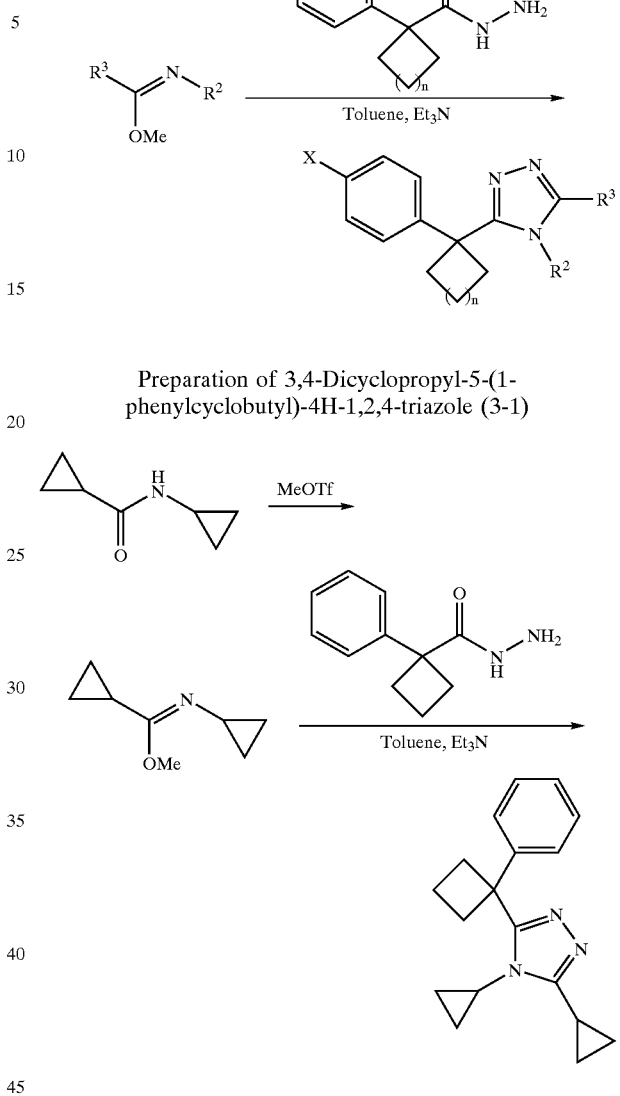

Preparation of 3,4-Dicyclopropyl-5-(1-phenylcyclobutyl)-4H-1,2,4-triazole (3-1)

Methyl trifluoromethanesulfonate (89.1 μL) was added to N-cyclopropylcyclopropanecarboxamide (98.6 mg, 0.788 mmole). After stirring at 60° C. for 30 minutes, NoM showed clean conversion to methyl N-cyclopropylcyclopropanecarboximidoate.

Toluene (2 mL), triethylamine (223 μL) and 1-phenylcyclobutanecarbohydrazide (90 mg) were added to methyl N-cyclopropylcyclopropanecarboximidoate and stirred at 60° C. for 3 hours and 110° C. for 1 hour. After cooling, the reaction was concentrated, and the residue was purified by preparative HPLC and isolated as the trifluoroacetate salt. The salt was added to a saturated sodium bicarbonate solution and extracted with ethyl acetate to give the freebase. The organic extract was dried over magnesium sulfate, filtered and concentrated to give 3,4-dicyclopropyl-5-(1-phenylcyclobutyl)-4H-1,2,4-triazole (3-1).

Compounds 3-2 to 3-18, 3-20 to 3-22, 3-24 to 3-27, and 3-30 to 3-40 were prepared by essentially the same procedure using the corresponding carboxamide and acyl hydrazide. Acetonitrile was used as solvent in the preparation of 3-2. Compound 3-19 was isolated as a byproduct in the synthesis of 3-18. The methyl amides were prepared from their corresponding methyl esters and methylamine using well established protocols. The other amides were conveniently prepared from commercially available carboxylic acids and amines using 1-(dimethylaminopropyl)-3-ethylcarbodiimide hydrochloride as the reagent and published procedures. Preparation of the acyl hydrazides was described in Procedures 3A, 3B, 3C and 3D.

| S.M. for: | Starting Carboxamide | Acyl Hydrazide X | n | S.M. for: | Starting Carboxamide | Acyl Hydrazide X | n |
|---|---|---|---|---|---|---|---|
| 3-1 | cyclopropyl-C(O)-NH-cyclopropyl | H | 1 | 3-2 | cyclopropyl-C(O)-NH-cyclopropyl | Cl | 1 |
| 3-3 | phenyl-C(O)-NH-Me | Cl | 1 | 3-4 | 4-F₃CO-phenyl-C(O)-NH-Me | Cl | 1 |
| 3-5 | 1-Me-cyclopropyl-C(O)-NH-cyclopropyl | Cl | 1 | 3-6 | 4-F₃CO-phenyl-C(O)-NH-CH₂CF₃ | Cl | 1 |
| 3-7 | 1-Me-cyclopropyl-C(O)-NH-cyclopropyl | F | 1 | 3-8 | 4-F₃CO-phenyl-C(O)-NH-Me | F | 1 |
| 3-9 | cyclopropyl-C(O)-NH-cyclopropyl | F | 0 | 3-10 | 1-Me-cyclopropyl-C(O)-NH-cyclopropyl | F | 0 |
| 3-11 | 1-Me-cyclopropyl-C(O)-NH-cyclopropyl | Cl | 0 | 3-12 | 4-F₃CO-phenyl-C(O)-NH-Me | Cl | 0 |
| 3-13 | 4-F₃CO-phenyl-C(O)-NH-Me | F | 0 | 3-14 | 4-HO-phenyl-C(O)-NH-Me | Cl | 1 |
| 3-15 | 2-OH-phenyl-C(O)-NH-Me | Cl | 1 | 3-16 | 2-naphthyl-C(O)-NH-Me | Cl | 1 |

-continued
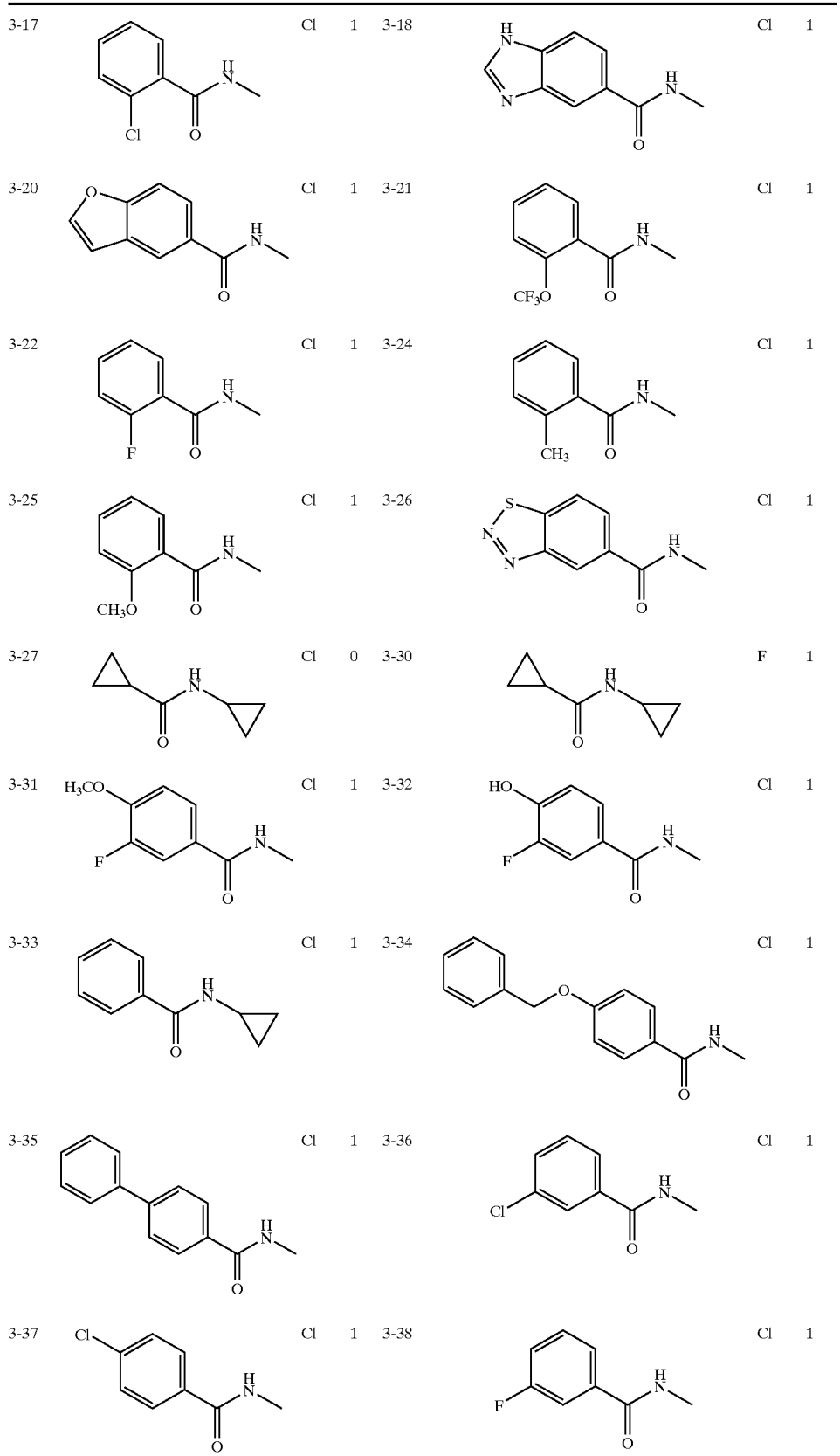

-continued
| Cpd | Structure | | | | |
|---|---|---|---|---|---|
| 3-39 | 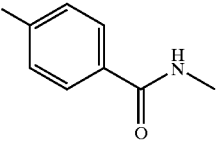 | Cl 1 | 3-40 | 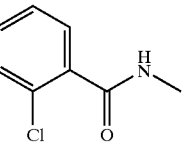 | Cl 1 |
| Cpd | Structure | Name | Retention Time (min) | MS ESI (m/z) |
|---|---|---|---|---|
| 3-1 | 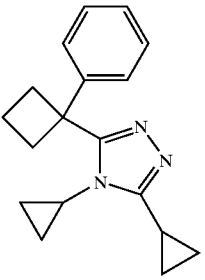 | 3,4-dicyclopropyl-5-(1-phenylcyclobutyl)-4H-1,2,4-triazole | 2.17 | 280.2 |
| 3-2 | 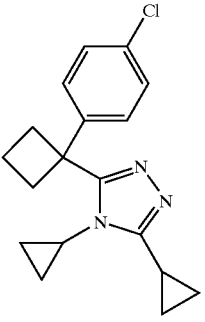 | 3-[1-(4-chlorophenyl)cyclobutyl]-4,5-dicyclopropyl-4H-1,2,4-triazole | 2.52 | 314.2 |
| 3-3 | 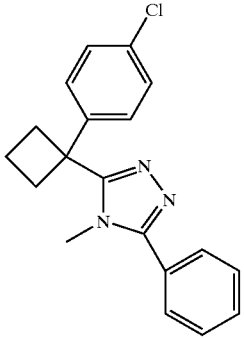 | 3-[1-(4-chlorophenyl)cyclobutyl]-4-methyl-5-phenyl-4H-1,2,4-triazole | 2.75 | 324.2 |
| 3-4 | 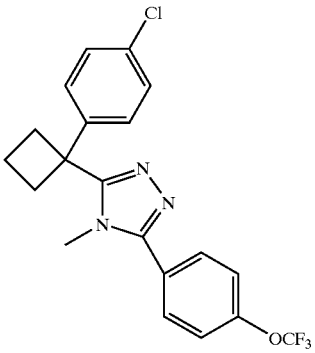 | 3-[1-(4-chlorophenyl)cyclobutyl]-4-methyl-5-[4-(trifluoromethoxy)phenyl]-4H-1,2,4-triazole | 3.33 | 408.1 |

-continued
| | | | | |
|---|---|---|---|---|
| 3-5 | 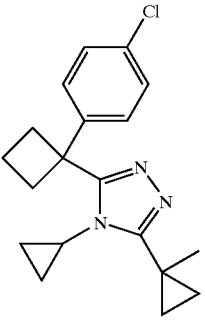 | 3-[1-(4-chlorophenyl)cyclo-butyl]-4-cyclopropyl-5-(1-methylcyclopropyl)-4H-1,2,4-triazole | 2.59 | 328.3 |
| 3-6 | 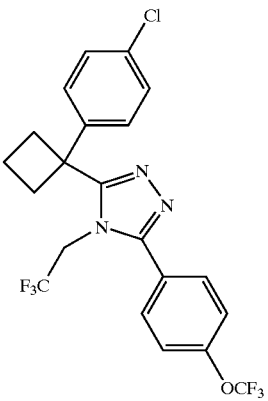 | 3-[1-(4-chlorophenyl)cyclo-butyl]-4-(2,2,2-trifluoroethyl)-5-[4-(trifluoromethoxy)-phenyl]-4H-1,2,4-triazole | 3.85 | 476.0 |
| 3-7 | 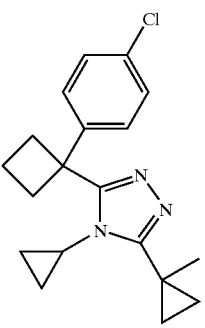 | 4-cyclopropyl-3-[1-(4-fluorophenyl)cyclo-butyl]-5-(1-methylcyclopropyl)-4H-1,2,4-triazole | 2.34 | 312.3 |
| 3-8 | 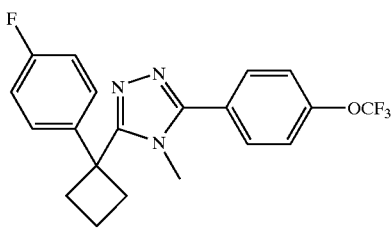 | 3-[1-(4-fluorophenyl)cyclo-butyl]-4-methyl-5-[4-(trifluoromethoxy)-phenyl]-4H-1,2,4-triazole | 3.04 | 392.1 |
| 3-9 | 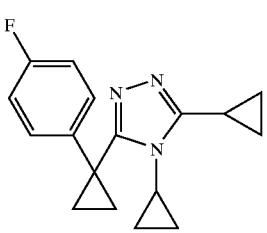 | 3,4-dicyclopropyl-5-[1-(4-fluorophenyl)cyclo-propyl]-4H-1,2,4-triazole | 2.07 | 284.2 |

-continued

| | | | | |
|---|---|---|---|---|
| 3-10 | 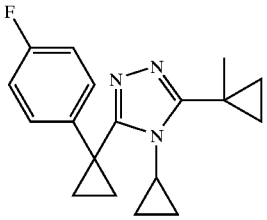 | 4-cyclopropyl-3-[1-(4-fluorophenyl)cyclopropyl]-5-(1-methylcyclopropyl)-4H-1,2,4-triazole) | 2.28 | 298.2 |
| 3-11 | 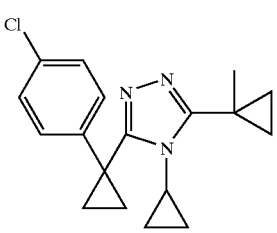 | 3-[1-(4-chlorophenyl)cyclopropyl]-4-cyclopropyl-5-(1-methylcyclopropyl)-4H-1,2,4-triazole | 2.47 | 314.1 |
| 3-12 | 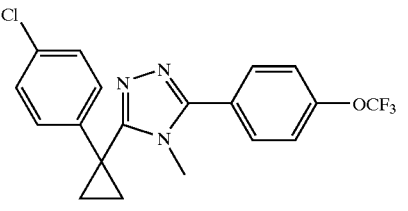 | 3-[1-(4-chlorophenyl)cyclopropyl]-4-methyl-5-[4-(trifluoromethoxy)phenyl]-4H-1,2,4-triazole | 3.16 | 394.1 |
| 3-13 | 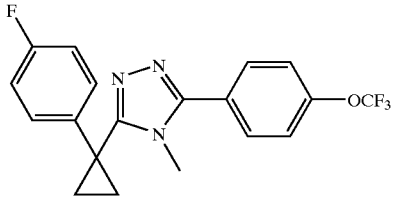 | 3-[1-(4-fluorophenyl)cyclopropyl]-4-methyl-5-[4-(trifluoromethoxy)phenyl]-4H-1,2,4-triazole | 2.49 | 378.1 |
| 3-14 | 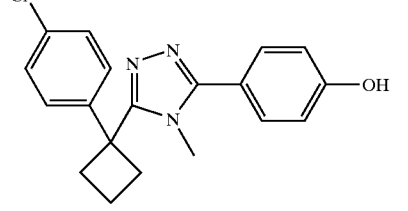 | 4-{5-[1-(4-chlorophenyl)cyclobutyl]-4-methyl-4H-1,2,4-triazol-3-yl}phenol | 2.41 | 340.1 |
| 3-15 | 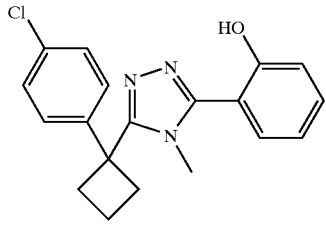 | 2-{5-[1-(4-chlorophenyl)cyclobutyl]-4-methyl-4H-1,2,4-triazol-3-yl}phenol | 2.48 | 340.1 |
| 3-16 | 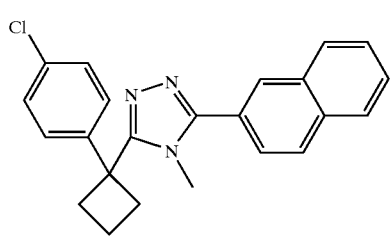 | 3-[1-(4-chlorophenyl)cyclobutyl]-4-methyl-5-(2-naphthyl)-4H-1,2,4-triazole | 3.12 | 374.1 |

-continued

| | | | | |
|---|---|---|---|---|
| 3-17 | | 3-(2-chlorophenyl)-5-[1-(4-chlorophenyl)cyclobutyl]-4-methyl-4H-1,2,4-triazole | 2.94 | 358.0 |
| 3-18 | | 6-{5-[1-(4-chlorophenyl)cyclobutyl]-4-methyl-4H-1,2,4-triazol-3-yl}-1H-benzimidazole | 2.01 | 364.1 |
| 3-19 | | 6-{5-[1-(4-chlorophenyl)cyclobutyl]-4-methyl-4H-1,2,4-triazol-3-yl}-1-methyl-1H-benzimidazole | 2.37 | 378.1 |
| 3-20 | | 3-[1-(4-chlorophenyl)cyclobutyl]-5-(2,3-dihydro-1-benzofuran-5-yl)-4-methyl-4H-1,2,4-triazole | 2.55 | 366.1 |
| 3-21 | | 3-[1-(4-chlorophenyl)cyclobutyl]-4-methyl-5-[2-(trifluoromethoxy)phenyl]-4H-1,2,4-triazole | 3.11 | 408.11 |

-continued
| | | | | |
|---|---|---|---|---|
| 3-22 | 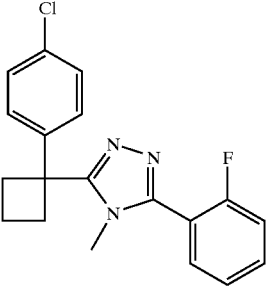 | 3-[1-(4-chlorophenyl)cyclobutyl]-5-(2-fluorophenyl)-4-methyl-4H-1,2,4-triazole | 2.66 | 342.1 |
| 3-24 | 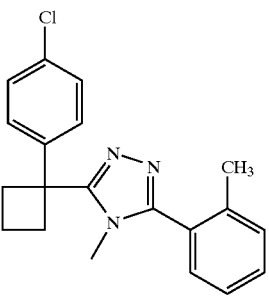 | 3-[1-(4-chlorophenyl)cyclobutyl]-4-methyl-5-(2-methylphenyl)-4H-1,2,4-triazole | 2.84 | 338.1 |
| 3-25 | 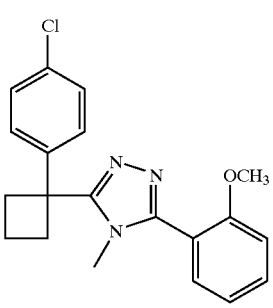 | 3-[1-(4-chlorophenyl)cyclobutyl]-5-(2-methoxyphenyl)-4-methyl-4H-1,2,4-triazole | 2.70 | 354.1 |
| 3-26 | 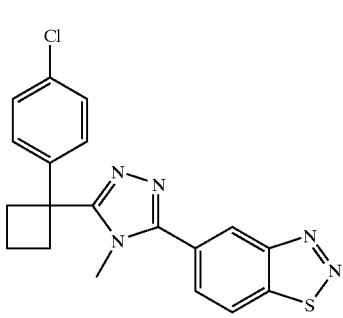 | 5-{5-[1-(4-chlorophenyl)cyclobutyl]-4-methyl-4H-1,2,4-triazol-3-yl}-1,2,3-benzothiadiazole | 2.82 | 382.1 |
| 3-27 | 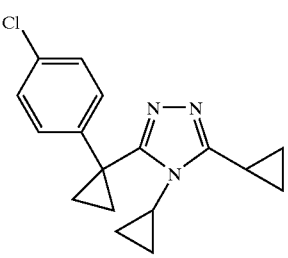 | 3-[1-(4-chlorophenyl)cyclopropyl]-4,5-dicyclopropyl-4H-1,2,4-triazole | 2.33 | 300.1 |

-continued

| | | | | |
|---|---|---|---|---|
| 3-30 | | 3,4-dicyclopropyl-5-[1-(4-fluorophenyl)cyclobutyl]-4H-1,2,4-triazole | 2.17 | 298.2 |
| 3-31 | | 3-[1-(4-chlorophenyl)cyclobutyl]-5-(3-fluoro-4-methoxyphenyl)-4-methyl-4H-1,2,4-triazole | 2.80 | 372.1 |
| 3-32 | | 4-{5-[1-(4-chlorophenyl)cyclobutyl]-4-methyl-4H-1,2,4-triazol-3-yl}-2-fluorophenyl | 2.51 | 358.1 |
| 3-33 | | 3-[1-(4-chlorophenyl)cyclobutyl]-4-cyclopropyl-5-phenyl-4H-1,2,4-triazole | 2.92 | 350.2 |
| 3-34 | | 3-[4-(benzyloxy)phenyl]-5-[1-(4-chlorophenyl)cyclobutyl]-4-methyl-4H-1,2,4-triazole | 3.32 | 430.1 |
| 3-35 | | 3-(1,1'-biphenyl-4-yl)-5-[1-(4-chlorophenyl)cyclobutyl]-4-methyl-4H-1,2,4-triazole | 3.30 | 400.1 |

| | | | | |
|---|---|---|---|---|
| | | -continued | | |
| 3-36 | 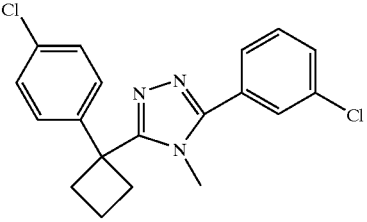 | 3-(3-chlorophenyl)-5-[1-(4-chlorophenyl)cyclobutyl]-4-methyl-4H-1,2,4-triazole | 3.09 | 358.1 |
| 3-37 | 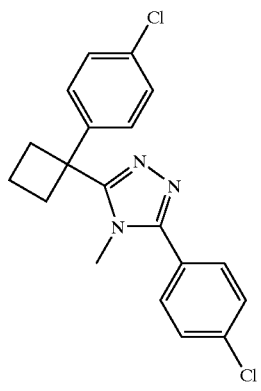 | 3-(4-chlorophenyl)-5-[1-(4-chlorophenyl)cyclobutyl]-4-methyl-4H-1,2,4-triazole | 3.04 | 358.1 |
| 3-38 | 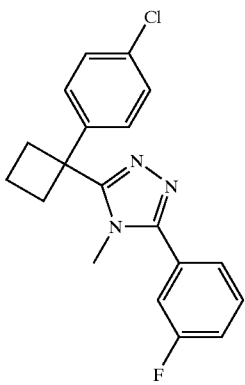 | 3-[1-(4-chlorophenyl)cyclobutyl]-5-(3-fluorophenyl)-4-methyl-4H-1,2,4-triazole | 2.78 | 342.1 |
| 3-39 | 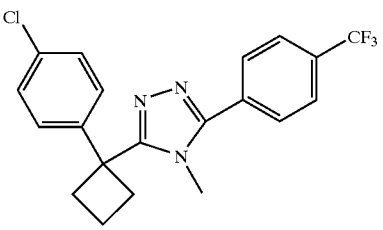 | 3-[1-(4-chlorophenyl)cyclobutyl]-4-methyl-5-[4-(trifluoromethyl)phenyl]-4H-1,2,4-triazole | 3.30 | 392.1 |

| | | | Retention Time (min) | MS ESI (m/z) |
|---|---|---|---|---|
| 3-40 | 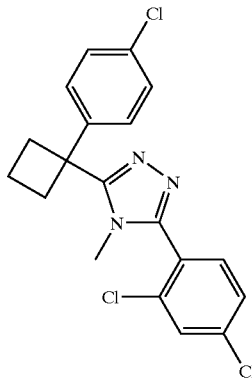 | 3-[1-(4-chlorophenyl)cyclobutyl]-5-(2,4-dichlorophenyl)-4-methyl-4H-1,2,4-triazole | 3.40 | 392.1 |

Procedure 3F

Preparation of 3-(1-Benzofuran-5-yl)-5-[1-(4-chlorophenyl)cyclobutyl]-4-methyl-4H-1,2,4-triazole (3-23)

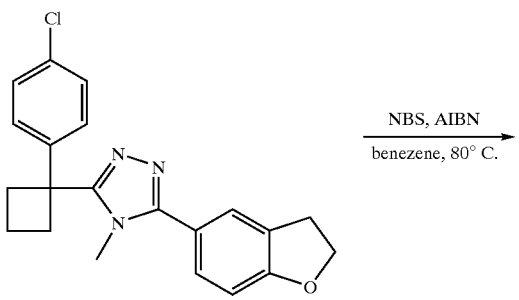

3-[1-4-Chlorophenyl)cyclobutyl]-5-(2,3-dihydro-1-benzofuran-5-yl)-4-methyl-4H-1,2,4-triazole (3-20, 9.7 mg) was dissolved in benzene (0.25 mL) [3]. N-Bromosuccinimide (7 mg) and catalytic 2,2'-azobisisobutyronitrile (ca. 1 mg) were added. After stirring at 80° C. overnight, the reaction was concentrated and the residue was purified by preparative TLC (5:15:80 Methanol/CH₂Cl₂/Ethyl acetate) to give the product (3-23) as a white solid (3.4 mg).

| Cpd | Structure | Name | Retention Time (min) | MS ESI (m/z) |
|---|---|---|---|---|
| 3-23 | 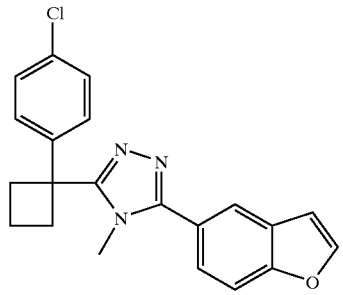 | 3-(1-benzofuran-5-yl)-5-[1-(4-chlorophenyl)cyclobutyl]-4-methyl-4H-1,2,4-triazole | 2.81 | 364.1 |

Procedure 3G

General Scheme

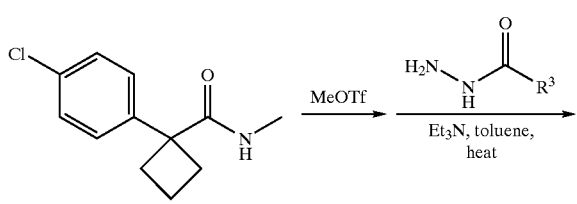

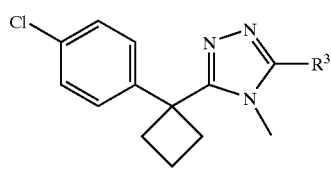

Preparation of 5-{5-[1-(4-Chlorophenyl)cyclobutyl]-4-methyl-4H-1,2,4-triazol-3-yl}-1H-indole (3-28)

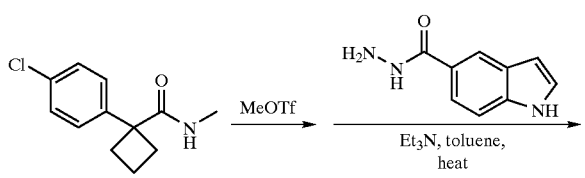

Methyl trifluoromethanesulfonate (33 μL) was added to 1-(4-chlorophenyl)-N-methylcyclobutanecarboxamide (65.9 mg, 0.295 mmole). After stirring at 60° C. for 30 minutes, NMR showed good conversion to methyl 1-(4-chlorophenyl)-N-methylcyclobutanecarboximidoate. Toluene (2 mL), triethylamine (82.3 μL) and 1H-indole-5-carbohydrazide (39.0 mg, 0.177 mmole) were added to the carboximidoate and stirred at 60° C. for 3 hours and 110° C. for 1 hour. After cooling, the reaction was concentrated and the residue was purified by preparative HPLC and isolated as the trifluoroacetate salt. The salt was added to a saturated sodium bicarbonate solution and extracted with ethyl acetate to give the freebase. The organic extract was dried over magnesium sulfate, filtered and concentrated to give 5-{5-[1-(4-chlorophenyl)cyclobutyl]-4-methyl-4H-1,2,4-triazol-3-yl}-1H-indole (3-28).

Compound 3-29 was prepared by essentially the same procedure using 2-(trifluoromethyl)benzohydrazide. The acyl hydrazides for 3-28 and 3-29 were prepared from their respective methyl esters using well established methods (anhydrous hydrazine, toluene, heat).

| Cpd | Structure | Name | Retention Time (min) | MS ESI (m/z) |
|---|---|---|---|---|
| 3-28 | 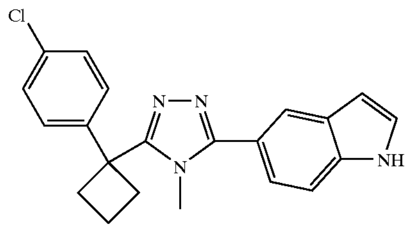 | 5-{5-[1-(4-chlorophenyl)cyclobutyl]-4-methyl-4H-1,2,4-triazol-3-yl}-1H-indole | 2.63 | 363.0 |
| 3-29 | 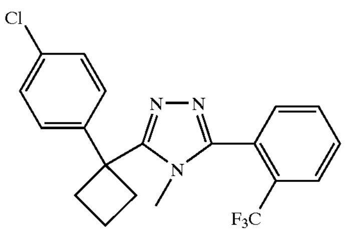 | 3-[1-(4-chlorophenyl)cyclobutyl]-4-methyl-5-[2-(trifluoromethyl)phenyl]-4H-1,2,4-triazole | 3.21 | 392.1 |

Procedure 3H

Preparation of 3,5-bis[1-(4-Chlorophenyl)cyclobutyl]-4-methyl-4H-1,2,4-triazole (3-41)

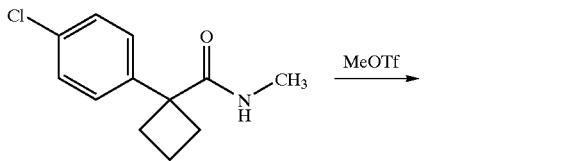

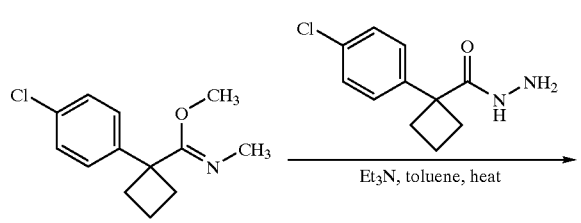

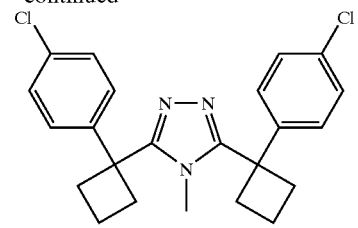

-continued

Methyl trifluoromethanesulfonate (52.0 μL, 0.460 mmole) was added to 1-(4-chlorophenyl)-N-methylcyclobutanecarboxamide (102.3 mg, 0.459 mmole). After stirring at 60° C. for 30 minutes, NMR showed good conversion to methyl 1-(4-chlorophenyl)cyclobutanecarboximidoate.

Toluene (2 mL), triethylamine (128 μL, 0.918 mmole) and 1-(4-chlorophenyl)cyclobutane carbohydrazide (76.2 mg, 0.340 mmole) were added to the methyl carboximidate and stirred at 60° C. for 12 hours and 110° C. for 1 hour. After cooling, the reaction was concentrated and the residue was purified by preparative HPLC and isolated as the trifluoroacetate salt. The salt was added to a saturated sodium bicarbonate solution and extracted with ethyl acetate to give the freebase. The organic extract was dried over magnesium sulfate, filtered and concentrated to provide 3,5-bis[1-(4-chlorophenyl)cyclobutyl]-4-methyl-4H-1,2,4-triazole (3-41).

| Cpd | Structure | Name | Retention Time (min) | MS ESI (m/z) |
|---|---|---|---|---|
| 3-41 | 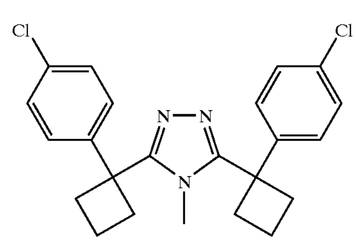 | 3,5-bis[1-(4-chlorophenyl)cyclobutyl]-4-methyl-4H-1,2,4-triazole | 3.40 | 412.2 |

Procedure 3I

Preparation of 3,5-bis[1-(4-Chlorophenyl)cyclopropyl]-4-methyl-4H-1,2,4-triazole (3-42)

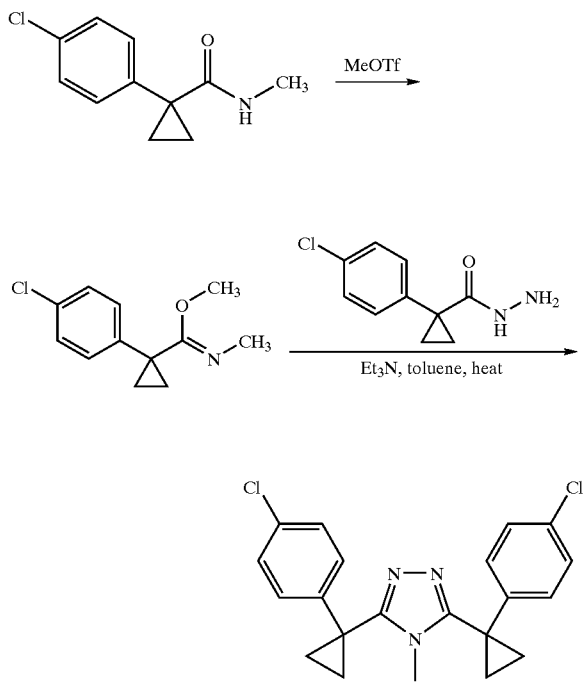

Methyl trifluoromethanesulfonate (54.0 μL, 0.478 mmole) was added to 1-(4-chlorophenyl)-N-methylcyclopropanecarboxamide (100.2 mg, 0.479 mmole). After stirring at 60° C. for 30 minutes, NMR showed the conversion to methyl 1-(4-chlorophenyl) cyclopropanecarboximidoate.

Toluene (2 mL), triethylamine (133.5 μL, 0.958 mmole) and 1-(4-chlorophenyl)cyclopropane carbohydrazide (60.7 mg, 0.289 mmole) were added to the methyl carboximidate and stirred at 60° C. for 12 hours and 110° C for 1 hour. After cooling, the reaction was concentrated, and the residue was purified by preparative HPLC and isolated as the trifluoroacetate salt. The salt was added to a saturated sodium bicarbonate solution and extracted with ethyl acetate to give the freebase. The organic extract was dried over magnesium sulfate, filtered and concentrated to give 3,5-bis[-(4-chlorophenyl)cyclopropyl]-4-methyl-4H-1,2,4-triazole (3-42).

Preparative HPLC Method for Example 3:
The procedure described in Example 2 was used.
Analytical LC Method for Exdample 3:
The procedures used were identical to those described in Example 2.

EXAMPLE 4

Procedure 4A

Preparation of 3-[1-(4-Chlorophenyl)-(Z)-3-(methoxymethoxy)cyclobutyl]-5,6,7,8,9,10-hexahydro[1,2,4]triazolo[4,3-a]azocine (4-1) and 3-[1-(4-chlorophenyl)-(E)-3-(methoxymethoxy)cyclobutyl]-5,6,7,8,9,10-hexahydro[1,2,4]triazolo[4,3-a]azocine (4-2)

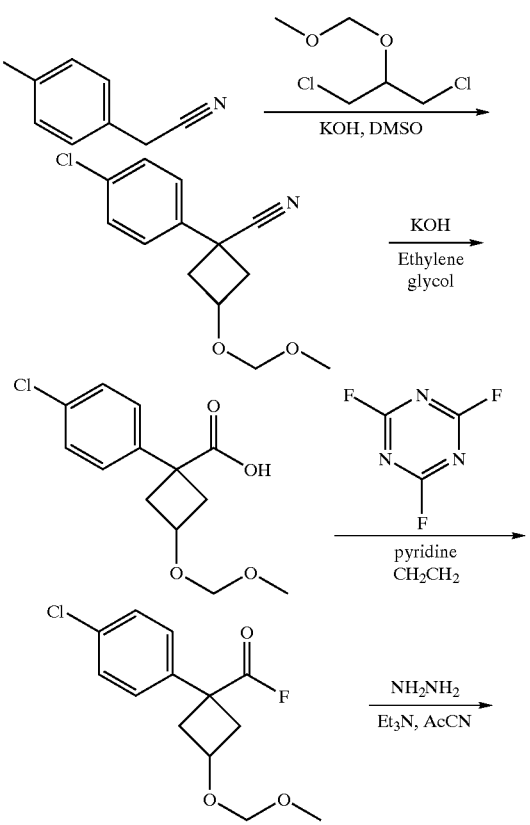

| Cpd | Structure | Name | Retention Time (min) | MS ESI (m/z) |
|---|---|---|---|---|
| 3-42 | 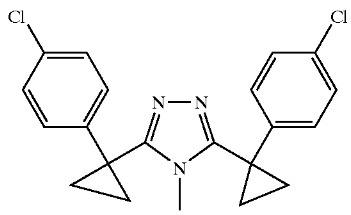 | 3,5-bis[1-(4-chlorophenyl)cyclopropyl]-4-methyl-4H-1,2,4-triazole | 3.20 | 384.2 |

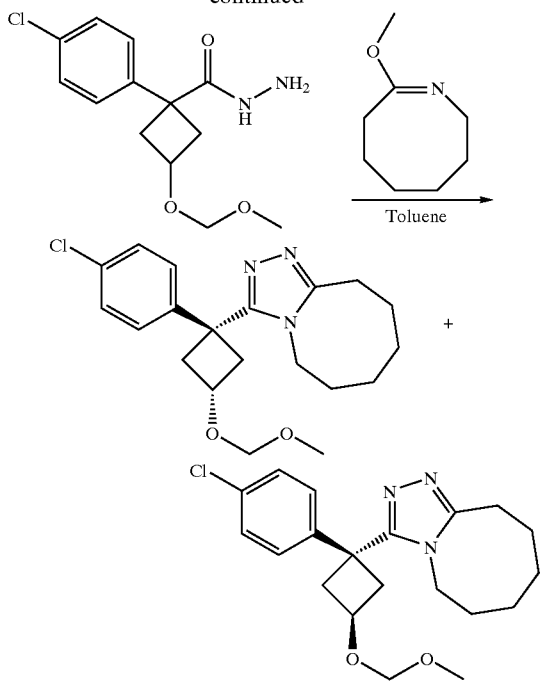

Potassium hydroxide (2.57 g) was dissolved in dimethyl sulfoxide (8.0 mL). (4-Chlorophenyl)acetonitrile (1.58 g, 10.4 mmol) and 1,3-dichloro-2-(methoxymethoxy)propane (1.993 g) were dissolved in ethyl ether (3 mL), and this mixture was added dropwise to the vigorously stirred potassium hydroxide solution at room temperature. After stirring at room temperature for one hour, the reaction was quenched by adding ice-cold water (5.5 mL). The mixture was filtered through a pad of celite which was washed with ether (30 mL). The filtrate was added to a separatory funnel, and the aqueous layer was extracted with ether (3×15 mL). The organic layers were combined, dried over magnesium sulfate, filtered, and concentrated. The product was purified by silica gel chromatography to provide 1-(4-chlorophenyl)-3-(methoxymethoxy)cyclobutanecarbonitrile (1.28 g) as a mixture of isomers (ca. 2:1).

The nitrile (1.28 g) and potassium hydroxide (2.2 g) were dissolved in ethylene glycol (13 mL). After heating for six hours at 198° C., the reaction mixture was cooled to room temperature, poured into water (15 mL), and washed with ether (2×20 mL). The aqueous solution was carefully acidified with aqueous hydrochloric acid and extracted with ether (2×20 mL). The organic layers were combined, dried over magnesium sulfate, filtered and concentrated to give the product as a brown oil (0.9068 g).

1-(4-Chlorophenyl)-3-(methoxymethoxy)cyclobutanecarboxylic acid (0.9068 g) and pyridine (0.40 mL) were dissolved in dichloromethane (12 mL) and cooled to −10° C. Cyanuric fluoride (1.0 mL) was dissolved in dichloromethane (2 mL) and added dropwise to the reaction mixture. After 30 minutes the reaction was added to a separatory funnel containing ice (10 μL). After vigorous shaking, the dichloromethane layer was removed, dried over magnesium sulfate, filtered and concentrated.

The crude acid fluoride was dissolved in acetonitrile (3 mL) and added to a stirring solution of anhydrous hydrazine (140 μL), triethylamine (1.0 mL), and acetonitrile (15 mL) at 0° C. After 10 minutes the reaction was complete by HPLC/MS and dried under vacuum.

A portion of the crude 1-(4-chlorophenyl)-3-(methoxymethoxy)cyclobutanecarbohydrazide (456.1 mg) was dissolved in anhydrous toluene (7 mL) and mixed with 8-methoxy-2,3,4,5,6,7-hexahydroazocine (228 μl). The solution was heated to 120° C. for three hours then slowly cooled to room temperature. The product was partially purified by silica gel chromatography (100% ethyl acetate→5% methanol in ethyl acetate→10% methanol in ethyl acetate) to give a mixture of 4-1 and 4-2 in a 62:38 ratio, respectively. The isomers were separated by preparative HPLC and isolated as their trifluoroacetate salts. Each salt was individually added to a saturated sodium bicarbonate solution and extracted with ethyl acetate. The purified freebases 3-[1-(4-chlorophenyl)-cis-3-(methoxymethoxy)cyclobutyl]-r-5,6,7,8,9,10-hexahydro[1,2,4]triazolo[4,3-α]azocine (4-1) and 3-[1-(4-chlorophenyl)-trans-3-(methoxymethoxy)cyclobutyl]-r-5,6,7,8,9,10-hexahydro[1,2,4]triazolo[4,3-α]azocine (4-2), were dried over magnesium sulfate, filtered and concentrated. The isomers, 4-1 and 4-2, were more efficiently separated by chiral preparative HPLC (ChiralPak OD (Daicel Chemical Industries) 2 cm×25 cm column, 20% isopropanol/heptane, 6 mL/min).

| Cpd | Structure | Name | Ret. Time (min) | MS ESI (m/z) |
|---|---|---|---|---|
| 4-1 | 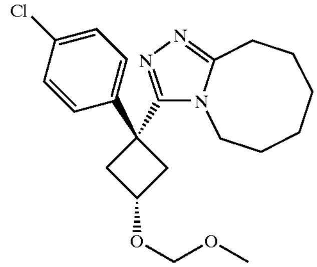 | 3-[1-(4-chlorophenyl)-cis-3-(methoxymethoxy)cyclobutyl]-r-5,6,7,8,9,10-hexahydro[1,2,4]triazolo[4,3-α]azocine | 2.56 | 376.2 |

-continued

| Cpd | Structure | Name | Ret. Time (min) | MS ESI (m/z) |
|---|---|---|---|---|
| 4-2 | 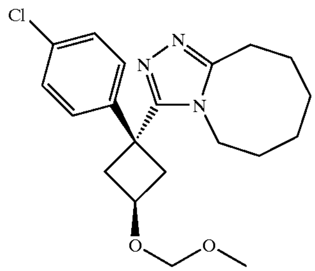 | 3-[1-(4-chlorophenyl)-trans-3-(methoxymethoxy)cyclobutyl]-r-5,6,7,8,9,10-hexahydro[1,2,4]triazolo[4,3-α]azocine | 2.45 | 376.2 |

Procedure 4B

Preparation of 3-(4-Chlorophenyl)-cis-3-(5,6,7,8,9,10-hexahydro[1,2,4]triazolo[4,3-a]azocin-3-yl)-cyclobutan-r-ol (4-3)

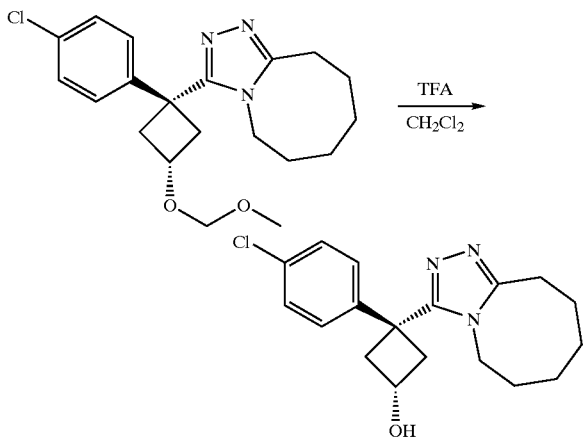

3-[1-(4-Chlorophenyl)-cis-3-(methoxymethoxy)cyclobutyl]-r-5,6,7,8,9,10-hexahydro[1,2,4]triazolo[4,3-a]azocine (4-1) (53 mg) was dissolved in dichloromethane (1 mL) and stirred at room temperature. Trifluoroacetic acid (0.2 mL) was added, and the solution was stirred overnight at room temperature. The volatiles were removed under vacuum, and the residue was purified by silica gel chromatography to give 3-(4-chlorophenyl)-cis-3-(5,6,7,8,9,10-hexahydro[1,2,4]triazolo[4,3-a]azocin-3-yl)-cyclobutan-r-ol (4-3) as a white solid (44 mg).

3-(4-chlorophenyl)-trans-3-(5,6,7,8,9,10-hexahydro[1,2,4]triazolo[4,3-a]azocin-3-yl)-cyclobutan-r-ol (4-4) was prepared by essentially the same procedure using the epimeric starting material (4-2).

| S.M. for: | Starting Material | S.M. for: | Starting Material |
|---|---|---|---|
| 4-3 | | 4-4 | |

| Cpd | Structure | Name | Ret. Time (min) | MS ESI (m/z) |
|---|---|---|---|---|

-continued

| | | | | |
|---|---|---|---|---|
| 4-3 | (structure) | 3-(4-chlorophenyl)-cis-3-(5,6,7,8,9,10-hexahydro[1,2,4]triazolo[4,3-α]azocin-3-yl)-cyclobutan-r-ol | 1.95 | 332.2 |
| 4-4 | (structure) | 3-(4-chlorophenyl)-trans-3-(5,6,7,8,9,10-hexahydro[1,2,4]triazolo[4,3-α]azocin-3-yl)-cyclobutan-r-ol | 1.97 | 332.2 |

Procedure 4C

Preparation of 3-(4-chlorophenyl)-3-(5,6,7,8,9,10-hexahydro[1,2,4]triazolo[4,3-a]azocin-3-yl)cyclobutanone (4-5)

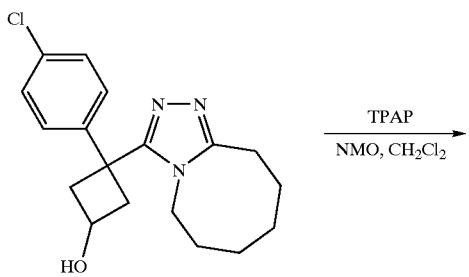

$\xrightarrow{\text{TPAP}}_{\text{NMO, CH}_2\text{Cl}_2}$

-continued

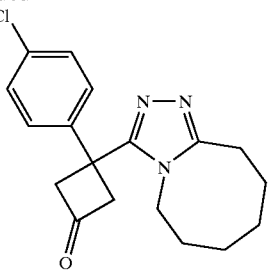

A mixture of alcohols (4-3 and 4-4) (114.1 mg) was dissolved in dichloromethane (5 mL) and cooled to 0° C. Tetrapropylammonium perruthenate (TPAP, 12.1 mg) and 4-methylmorpholine N-oxide (60.4 mg) were added, and the reaction was warmed to room temperature. After three hours, the crude reaction was added directly onto a silica gel column and purified (100% dichloromethane 5% methanol in dichloromethane 10% methanol in dichloromethane) to give 3-(4-chlorophenyl)-3-(5,6,7,8,9,10-hexahydro[1,2,4]triazolo[4,3-a]azocin-3-yl)cyclobutanone (4-5) (93 mg).

| Cpd | Structure | Name | Ret. Time (min) | MS ESI (m/z) |
|---|---|---|---|---|
| 4-5 | (structure) | 3-(4-chlorophenyl)-3-(5,6,7,8,9,10-hexahydro[1,2,4]triazolo[4,3-α]azocin-3-yl)cyclobutanone | 2.18 | 330.1 |

Procedure 4D

Preparation of 3-[1-(4-Chlorophenyl)-3-methylenecyclobutyl]-5,6,7,8,9,10-hexahydro[1,2,4]triazolo[4,3-a]azocine (4-6)

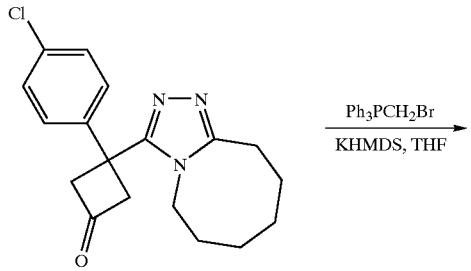

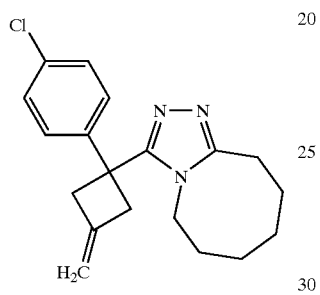

3-(4-Chlorophenyl)-3-(5,6,7,8,9,10-hexahydro[1,2,4]triazolo[4,3-a]azocin-3-yl)cyclobutanone (4-5) (52 mg) was dissolved in freshly distilled tetrahydrofuran (2 mL). Methyltriphenylphosphonium bromide (281 mg) was added followed by potassium bis(trimethylsilyl)amide (KHMDS, 0.5M in toluene, 1.25 mL). After stirring for 24 hours at room temperature, the crude product was added to a saturated sodium bicarbonate solution and extracted with ethyl acetate. The organic layer was collected, dried over magnesium sulfate, filtered and concentrated. The product was purified by silica gel column chromatography to give 3-[1-(4-chlorophenyl)-3-methylenecyclobutyl]-5,6,7,8,9,10-hexahydro[1,2,4]triazolo[4,3-a]azocine (4-6).

Procedure 4E

Preparation of 3-[1-(4-Chlorophenyl)-3,3-difluorocyclobutyl]-5,6,7,8,9,10-hexahydro[1,2,4]triazolo[4,3-a]azocine (4-7)

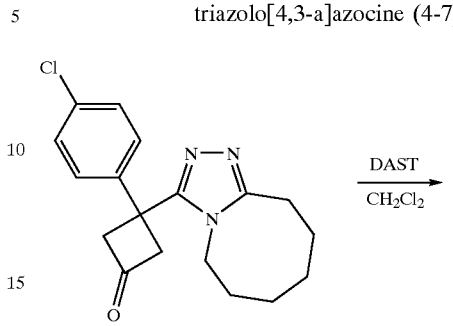

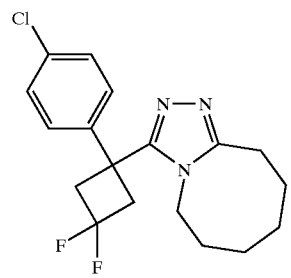

3-(4-Chlorophenyl)-3-(5,6,7,8,9,10-hexahydro[1,2,4]triazolo[4,3-a]azocin-3-yl)cyclobutanone (4-5) (11.4 mg) was dissolved in dichloromethane (1 mL). (Diethylamino)sulfur trifluoride (DAST, 73 µL) was added, and the solution was stirred for 24 hours at room temperature. The solution was poured into saturated aqueous sodium bicarbonate and extracted with dichloromethane. The organic layer was dried over magnesium sulfate, filtered and concentrated. The residue was purified by silica gel chromatography (100% dichloromethane→1% methanol in dichloromethane→5% methanol in dichloromethane) to give 3-[1-(4-chlorophenyl)-3,3-difluorocyclobutyl]-5,6,7,8,9,10-hexahydro[1,2,4]triazolo[4,3-a]azocine (4-7) (6.8 mg).

| Cpd | Structure | Name | Ret. Time (min) | MS ESI (m/z) |
|---|---|---|---|---|
| 4-6 | (structure shown) | 3-[1-(4-chlorophenyl)-3-methylenecyclobutyl]-5,6,7,8,9,10-hexahydro[1,2,4]triazolo[4,3-α]azocine | 2.64 | 328.2 |

| Cpd | Structure | Name | Ret. Time (min) | MS ESI (m/z) |
|---|---|---|---|---|
| 4-7 | 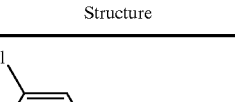 | 3-[1-(4-chlorophenyl)-3,3-difluorocyclobutyl]-5,6,7,8,9,10-hexahydro[1,2,4]triazolo[4,3-α]azocine | 2.56 | 352.1 |

Procedure 4F

Preparation of 3-[1-(4-Chlorophenyl)-trans-3-fluorocyclobutyl]-r-5,6,7,8,9,10-hexahydro[1,2,4]triazolo[4,3-a]azocine (4-8)

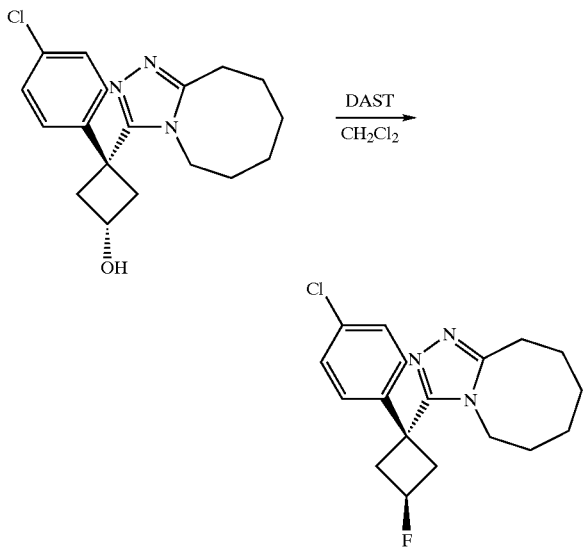

3-(4-Chlorophenyl)-cis-3-(5,6,7,8,9,10-hexahydro[1,2,4]triazolo[4,3-a]azocin-3-yl)-cyclobutan-r-ol (4-3) (21.3 mg) was dissolved in anhydrous dichloromethane (1.5 μL) and cooled to 0° C. (Diethylamino)sulfur trifluoride (DAST, 80 μL) was added. The solution was warmed to room temperature and stirred overnight. The product was poured into saturated aqueous sodium bicarbonate and extracted with dichloromethane. The organic layer was dried over magnesium sulfate, filtered and concentrated. The residue was purified by silica gel chromatography (100% dichloromethane→1% methanol in dichloromethane→5% methanol in dichloromethane) to give 3-[1-(4-chlorophenyl)-trans-3-fluorocyclobutyl]-r-5,6,7,8,9,10-hexahydro[1,2,4]triazolo[4,3-a]azocine (4-8).

3-[1-(4-chlorophenyl)-trans-3-fluorocyclobutyl]-r-5,6,7,8,9,10-hexahydro[1,2,4]triazolo[4,3-a]azocine (4-9) was prepared by essentially the same procedure using the epimeric starting material (4-4).

| S.M. for: | Starting Material | S.M. for: | Starting Material |
|---|---|---|---|
| 4-8 | | 4-9 | |

| Cpd | Structure | Name | Ret. Time (min) | MS ESI (m/z) |
|---|---|---|---|---|

| | | | Ret. Time (min) | MS ESI (m/z) |
|---|---|---|---|---|
| 4-8 | 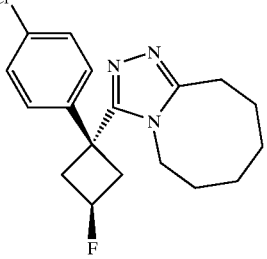 | 3-[1-(4-chlorophenyl)-trans-3-fluorocyclobutyl]-r-5,6,7,8,9,10-hexahydro[1,2,4]triazolo[4,3-α]azocine | 2.47 | 334.1 |
| 4-9 | 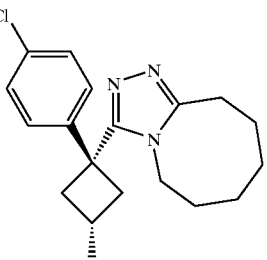 | 3-[1-(4-chlorophenyl)-cis-3-fluorocyclobutyl]-r-5,6,7,8,9,10-hexahydro[1,2,4]triazolo[4,3-α]azocine | 2.39 | 334.1 |

Procedure 4G

Preparation of 3-(3-Methyl-1-phenylcyclobutyl)-5,6,7,8,9,10-hexahydro[1,2,4]triazolo[4,3-a]azocine (4-10)

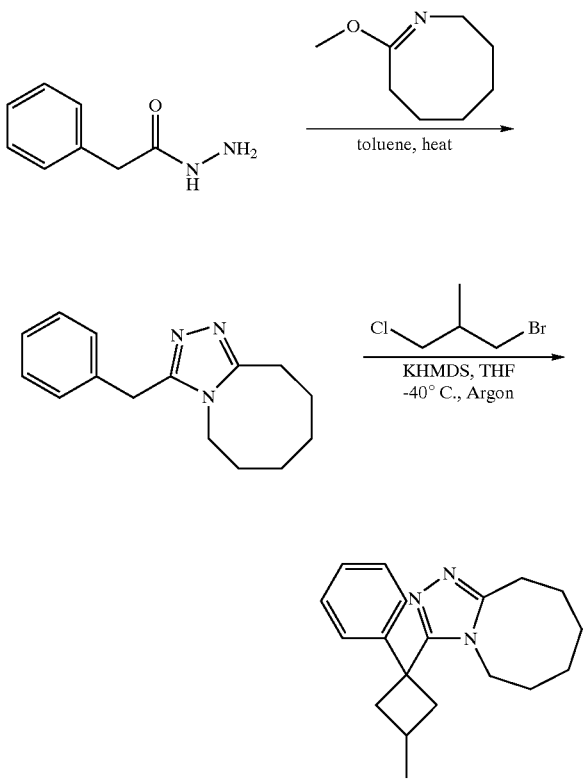

2-Phenylacetohydrazide (1.01 g) was added to a solution of anhydrous toluene (11 mL) and 8-methoxy-2,3,4,5,6,7-hexahydroazocine (0.96 mL). The mixture was warmed to 60° C. for 3 hours and heated to 110° C. overnight. The solution was cooled to room temperature and concentrated. The residue was purified by silica gel chromatography to give 3-benzyl-5,6,7,8,9,10-hexahydro[1,2,4]triazolo[4,3-a]azocine as a white solid.

3-Benzyl-5,6,7,8,9,10-hexahydro[1,2,4]triazolo[4,3-a]azocine (287.6 mg) and 1-bromo-3-chloro-2-methylpropane (140 μL) were dissolved in anhydrous, deoxygenated tetrahydrofuran, and the solution was cooled to −40° C. under an argon atmosphere. Potassium bis(trimethylsilyl)amide (KHMDS, 0.5M in toluene, 2.5 mL) was added dropwise. After 30 minutes, a second aliquot of KHMDS (2.5 mL) was added. After 30 additional minutes, KHMDS (2.15 mL) was added again, and the solution was allowed to slowly warm to room temperature. After one hour, the reaction was quenched with water and added to brine. After extraction with ethyl acetate, the organic layer was dried with magnesium sulfate, filtered, evaporated and purified by silica gel chromatography to give 3-[1-(4-chlorophenyl)-(Z)-3-(methoxymethoxy)cyclobutyl]-5,6,7,8,9,10-hexahydro[1,2,4]triazolo[4,3-a]azocine (4-10) as a ca. 1.2:1 mixture of isomers.

| Cpd | Structure | Name | Ret. Time (min) | MS ESI (m/z) |
|---|---|---|---|---|
| 4-10 | 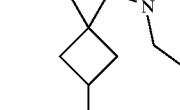 | 3-(3-methyl-1-phenylcyclobutyl)-5,6,7,8,9,10-hexahydro-[1,2,4]triazolo[4,3-a]azocine | 2.32 | 296.2 |

Procedure 4H

Preparation of 1-(4-Chlorophenyl)-trans-3-fluorocyclobutane-r-carbohydrazide

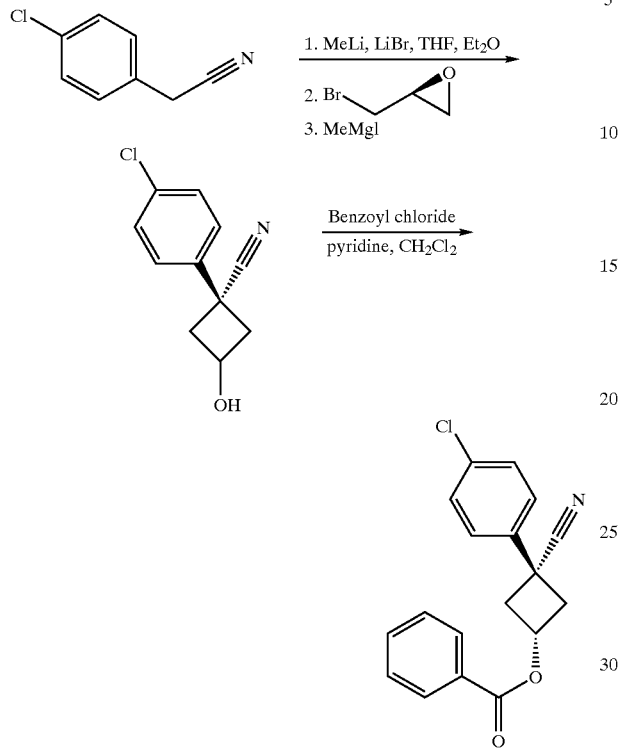

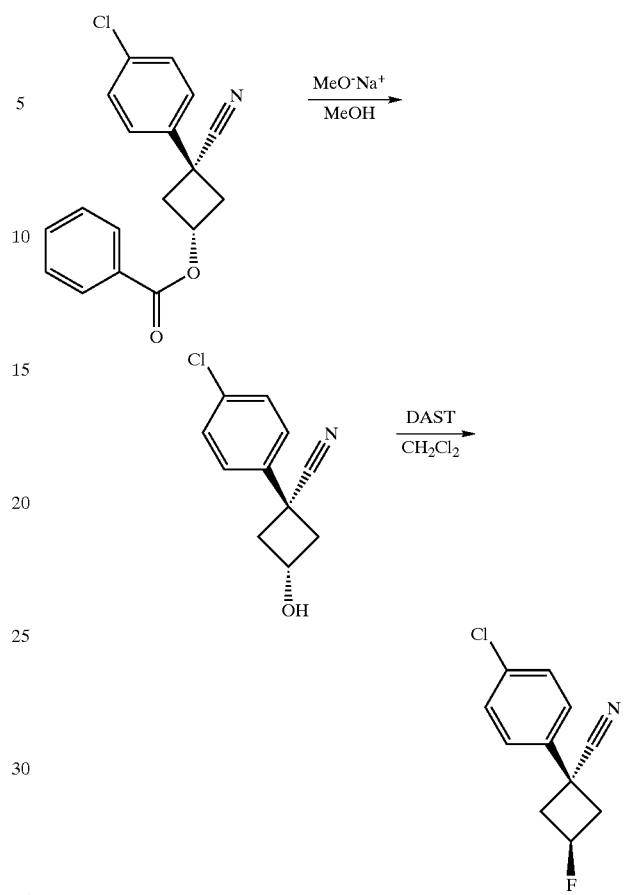

(4-Chlorophenyl)acetonitrile (14.04 g) was dissolved in freshly distilled tetrahydrofuran (250 mL) and stirred at −78° C. under argon [1]. Methyl lithium (LiBr complex, 1.5 M in diethyl ether, 62 mL, 1 eq.) was added dropwise such that the reaction temperature stayed below −66° C. The solution was stirred for one hour at −78° C. and turned from yellow to deep red. Epibromohydrin was added dropwise and the solution was stirred for an additional 90 minutes. Methyl magnesium iodide (3.0M in diethyl ether, 31 mL) was added and the solution turned light brown as it was slowly warmed to room temperature and stirred overnight. The reaction was quenched with water (75 mL) and acidified to pH 2 with 5 N aqueous hydrochloric acid (ca. 30 mL). Brine was added until the layers separated. The organic layer was collected and the aqueous layer was reextracted with diethyl ether (2×50 mL). The organic layers were combined, dried with magnesium sulfate, filtered and concentrated.

The crude 1-(4-chlorophenyl)-3-hydroxycyclobutane-1-carbonitrile (ca. 4.2:1 ratio of cis:trans isomers) was dissolved in dichloromethane (150 mL) and stirred at 0° C. Pyridine (11.3 mL) and then benzoyl chloride (10.8 mL) were added and the solution was warmed to room temperature and stirred for 2.5 hours. Additional pyridine (2 mL) and benzoyl chloride (2 mL) were added and the reaction was stirred at 30° C. overnight. The reaction was added to a saturated sodium bicarbonate solution and extracted with dichloromethane. The organic layer was washed with saturated ammonium chloride, dried over magnesium chloride, filtered and concentrated to give a reddish oil. The two isomers were separated by silica gel chromatography (25% dichloromethane/hexanes→33% dichloromethane/hexanes→50% dichloromethane/hexanes→100% dichloromethane) to give the desired 3-(4-chlorophenyl)-cis-3-cyanocyclobutyl benzoate (18.63 g).

3-(4-Chlorophenyl)-cis-3-cyanocyclobutyl benzoate (6.42 g) was dissolved in methanol/tetrahydrofuran (10 mL/20 mL) and stirred at room temperature. Lithium hydroxide monohydrate (1.1 g) was dissolved in water (10 mL) and added to the benzoate solution. After 10 minutes, solid ammonium chloride (ca. 2 g) was added and the volatile solvents were removed by evaporation. The remaining aqueous mixture was extracted with diethyl ether, and the organic layer was dried with magnesium sulfate, filtered, and concentrated to give the desired cyclobutanol.

A portion of the 1-(4-chlorophenyl)-cis-3-hydroxycyclobutane-r-carbonitrile (1.13 g) was dissolved in anhydrous dichloromethane and stirred at 0° C. (Diethylamino)sulfur trifluoride (DAST, 1.43 g) was added and the solution was warmed to 40° C. for 10 hours. Additional DAST (0.5 mL) was added and the reaction was stirred overnight at 40° C. The solution was cooled, added to saturated aqueous sodium bicarbonate, and extracted twice with dichloromethane. The organic extracts were combined, dried with magnesium sulfate, filtered and concentrated. The crude residue was carefully chromatographed on silica gel (10% ethyl acetate/hexanes→20% ethyl acetate/hexanes→25% ethyl acetate/hexanes) to give 1-(4-chlorophenyl)-trans-3-fluorocyclobutane-r-carbonitrile (1.024 g).

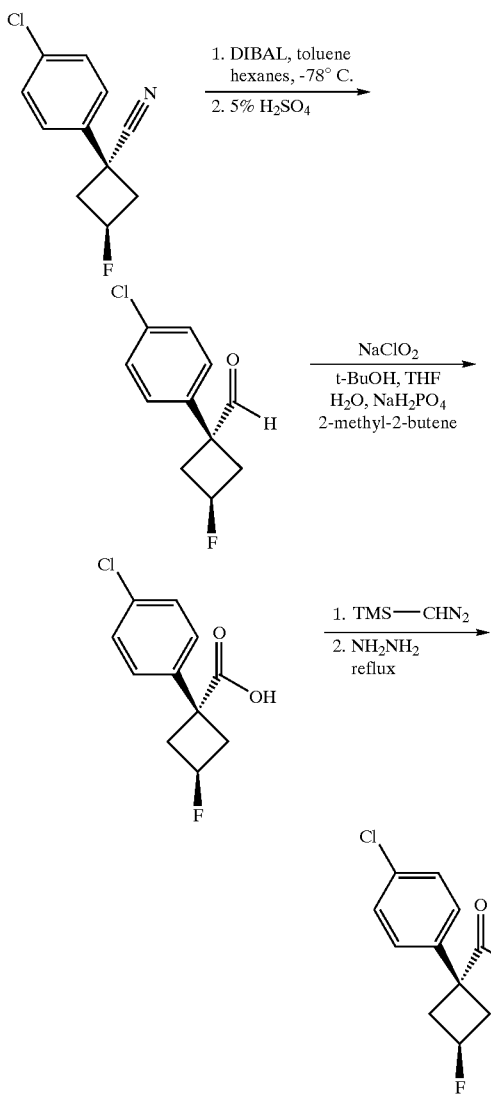

methanol (40 mL/10 mL). (Trimethylsilyl)diazomethane (15 mL, 2.0 M in hexanes) was added until the yellow color remained. After stirring at room temperature for one hour, TLC showed the reaction was complete. Acetic acid (2 mL) was added to quench the (trimethylsilyl)diazomethane, and the solution was concentrated to give methyl 1-(4-chlorophenyl)-trans-3-fluorocyclobutane-r-carboxylate.

The crude methyl ester (5.8 g) was dissolved in toluene (15 mL). Anhydrous hydrazine (3.1 mL, 98.8 mmole) was added and the reaction was refluxed for two days. After cooling to room temperature and removing the toluene under vacuum, the product was purified by silica gel chromatography (100% Ethyl acetate) to give 1-(4-chlorophenyl)-trans-3-fluorocyclobutane-r-carbohydrazide as a white solid (4.82 g).

Procedure 4I

General Scheme

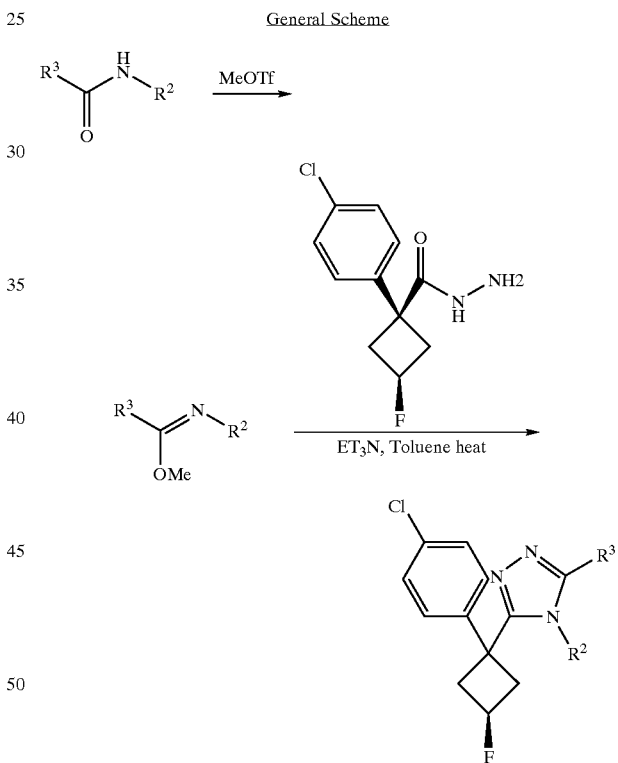

1-(4-Chlorophenyl)-trans-3-fluorocyclobutane-r-carbonitrile (1.65 g) was dissolved in anhydrous toluene (30 mL) and cooled to −78° C. A solution of diisobutylaluminum hydride (DIBAL, 1 M in hexanes, 9.4 mL) was added over 10 minutes, and the solution was stirred for 30 minutes. The reaction was quenched by adding 5% sulfuric acid (2.5 mL) and warmed to room temperature. After one hour, the mixture was filtered through a pad of celite. The pad was washed with ethyl acetate, and the entire filtrate was poured into water (20 mL). After separating the layers, the aqueous solution was extracted with ethyl acetate. The organic layers were combined, dried with magnesium sulfate, filtered and concentrated.

The crude aldehyde was dissolved in t-butanol/tetrahydrofuran/2-methylbut-2-ene (15 mL/5 mL/5 mL) and stirred at room temperature. Sodium chlorite (1.56 g) and sodium dihydrogenphosphate (2.39 g) were dissolved in water (7 mL), and added to the vigorously stirring solution. After 80 minutes, the volatile solvents were removed under vacuum and the mixture was acidified to pH 2 with aqueous 1N hydrochloric acid. The product was extracted with ethyl acetate (3×30 mL). The extracts were combined, dried over magnesium sulfate, filtered, and evaporated to give the desired carboxylic acid.

1-(4-Chlorophenyl)-trans-3-fluorocyclobutane-r-carboxylic acid (5.68 g) was dissolved in dichloromethane/

Preparation of 3-[1-(4-Chlorophenyl)-trans-3-fluorocyclobutyl]4,5-dicyclopropyl-r-4H-1,2,4-triazole (4-11)

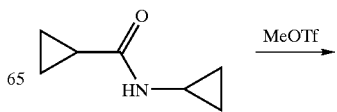

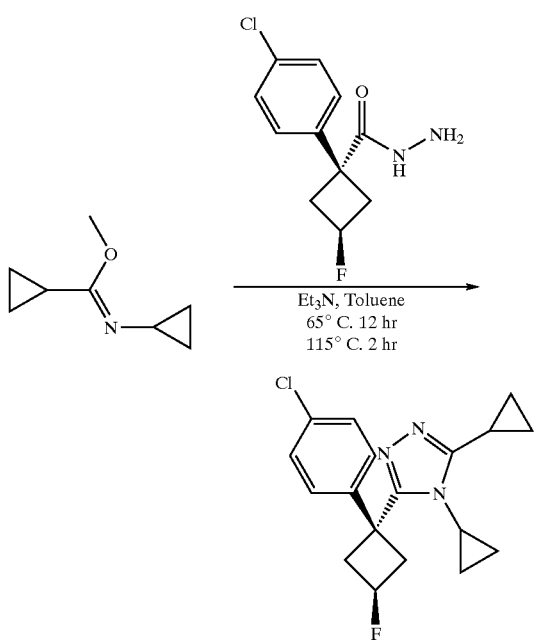

Methyl trifluoromethanesulfonate (84.1 μl) was added to N-cyclopropylcyclopropanecarboxamide (93.0 mg). After warming to 65° C. for 2 minutes, the reaction was cooled to room temperature. Toluene (1 mL), triethylamine (207 μL), and 1-(4-chlorophenyl)-trans-3-fluorocyclobutane-r-carbohydrazide (108 mg) were added to the methyl N-cyclopropylcyclopropanecarboximidoate and stirred at 60° C. for overnight and 115° C. for 2 hours. After cooling, the solution was concentrated and the residue was purified by silica gel chromatography (100% ethyl acetate→1% methanol in ethyl acetate→3% methanol in ethyl acetate→5% methanol in ethyl acetate) to give the purified 3-[1-(4-chlorophenyl)-trans-3-fluorocyclobutyl]-4,5-dicyclopropyl-r-4H-1,2,4-triazole (4-11) (57.2 mg).

Compounds 4-12 to 4-15 were prepared by essentially the same procedure using the corresponding carboxamide starting material and 1-(4-chlorophenyl)-trans-3-fluorocyclobutane-r-carbohydrazide.

-continued

| | | | RT | MS | Method |
|---|---|---|---|---|---|
| 4-11 | | 3-[1-(4-chlorophenyl)-trans-3-fluorocyclobutyl]-4,5-dicyclopropyl-r-4H-1,2,4-triazole | 2.45 | 332.1 | 51 |
| 4-12 | | 3-[1-(4-chlorophenyl)-trans-3-fluorocyclobutyl]-4-cyclopropyl-5-(1-methylcyclopropyl)-r-4H-1,2,4-triazole | 2.60 | 346.1 | 51 |
| 4-13 | | 3-[1-(4-chlorophenyl)-trans-3-fluorocyclobutyl]-4-methyl-5-[4-(trifluoromethoxy)-phenyl]-r-4H-1,2,4-triazole | 3.58 | 426.0 | 51 |
| 4-14 | | 3-[1-(4-chlorophenyl)-trans-3-fluorocyclobutyl]-4-methyl-5-[2-(trifluoromethoxy)-phenyl]-r-4H-1,2,4-triazole | 3.32 | 426.2 | 51 |
| 4-15 | | 3-(2-chlorophenyl)-5-[1-(4-chlorophenyl)-trans-3-fluorocyclobutyl]-4-methyl-r-4H-1,2,4-triazole | 3.14 | 376.1 | 51 |

Preparative HPLC Method for EXAMPLE 4:

The preparative HPLC method used was the same as that described in Example 2.

The Analytical LC Method was identical to that described in Example 2.

References

1. Jeffery, J. E.; Kerrigan, F.; Miller, T. K.; Smith, G. J.; Tometzki, G. B.; J. Chem. Soc., Perkin Trans 1, 1996, (21), 2583–2589
2. Fedorynski, M.; Jonczyk, A. Org Prep. Proced Int., 1995, 27 (3), 355–359

3. Suzuki, H.; Tsutsui, H.; Kano, A.; Katoh, S.; Morita, T.; Matsuda, K.; Iibuchi, N.; Ogawa, M. Heterocycles, 1997, 45 (9), 1657–61

While certain preferred embodiments of the invention have been described herein in detail, numerous alternative embodiments are contemplated as falling within the scope of the claims. Consequently, the invention is broader than the specific embodiments provided herein.

What is claimed is:

1. A compound represented by Formula I:

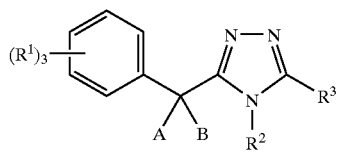

or a pharmaceutically acceptable salt or solvate thereof, wherein:

A and B together represents $C_{2-5}$alkanediyl such that they form a 3–6 membered ring with the carbon atom to which they are attached, said ring optionally containing 1 double bond or 1–2 heteroatoms selected from O, S and N, said 3–6 membered ring being optionally substituted with $C_{1-4}$alkylene, oxo, ethylenedioxy or propylenedioxy, and being further optionally substituted with 1–4 groups selected from halo, $C_{1-4}$alkyl, halo$C_{1-4}$alkyl, $C_{1-3}$acyl, $C_{1-3}$acyloxy, $C_{1-3}$alkoxy, $C_{1-6}$alkylOC(O)—, $C_{2-4}$alkenyl, $C_{2-4}$alkynyl, $C_{1-3}$alkoxy$C_{1-3}$alkyl, $C_{1-3}$alkoxy$C_{1-3}$alkoxy, phenyl, CN, OH, D, $NH_2$, $NHR^a$ and $N(R^a)_2$ wherein $R^a$ represents $C_{1-3}$alkyl, $OC_{1-3}$alkyl, $C_{6-10}$ar$C_{1-6}$alkylene or phenyl optionally substituted with 1–3 halo groups;

each $R^1$ represents H or is independently selected from the group consisting of: OH, halo, $C_{1-10}$alkyl, $C_{1-6}$alkoxy and $C_{6-10}$aryl, said $C_{1-10}$alkyl, $C_{6-10}$aryl and the alkyl portion of $C_{1-6}$alkoxy being optionally substituted with 1–3 halo, OH, $OC_{1-3}$alkyl, phenyl or naphthyl groups, said phenyl and naphthyl being optionally substituted with 1–3 substituents independently selected from halo, $OCH_3$, $OCF_3$, $CH_3$, $CF_3$ and phenyl, wherein said phenyl is optionally substituted with 1–3 halo groups, or two $R^1$ groups taken together represent a fused $C_{5-6}$alkyl or aryl ring, which may be optionally substituted with 1–2 OH or $R^a$ groups, wherein $R^a$ is as defined above;

$R^2$ is selected from the group consisting of (a) $C_{1-14}$alkyl optionally substituted with 1–6 halo groups and 1–3 substituents selected from OH, $OC_{1-3}$alkyl, and phenyl, said phenyl being optionally substituted with 1–4 groups independently selected from halo, $OCH_3$, $OCF_3$, $CH_3$ and $CF_3$, and said $C_{1-3}$alkyl portion of $OC_{1-3}$alkyl being optionally substituted with 1–3 halo groups; (b) phenyl or pyridyl optionally substituted with 1–3 halo, OH or $R^a$ groups, with $R^a$ as previously defined; (c) $C_{2-10}$ alkenyl, optionally substituted with 1–3 substituents independently selected from halo, OH and $OC_{1-3}$alkyl, said $C_{1-3}$alkyl portion of $OC_{1-3}$alkyl being optionally substituted with 1–3 halo groups; (d) $CH_2CO_2H$; (e) $CH_2CO_2C_{1-6}$alkyl; (f) $CH_2C(O)NHR^a$ wherein $R^a$ is as previously defined; (g) $NH_2$, $NHR^a$ and $N(R^a)_2$ wherein $R^a$ is as previously defined;

$R^3$ is selected from the group consisting of: $C_{1-14}$alkyl, $C_{2-10}$alkenyl, $SC_{1-6}$alkyl, $C_{6-10}$aryl, heterocyclyl and heteroaryl, said alkyl, alkenyl, aryl, heterocyclyl, heteroaryl and the alkyl portion of $SC_{1-6}$alkyl being optionally substituted with (a) R; (b) 1–6 halo groups and (c) 1–3 groups selected from OH, $NH_2$, $NHC_{1-4}$alkyl, $N(C_{1-4}alkyl)_2$, $C_{1-4}$alkyl, $OC_{1-4}$alkyl, CN, $C_{1-4}$alkylS(O)$_x$— wherein x is 0, 1 or 2, $C_{1-4}$alkylSO$_2$NH—, $H_2NSO_2$—, $C_{1-4}$alkylNHSO$_2$— and $(C_{1-4}alkyl)_2NSO_2$—, said $C_{1-4}$alkyl and the $C_{1-4}$alkyl portions of said groups being optionally substituted with phenyl and 1–3 halo groups, and R is selected from heterocyclyl, heteroaryl and aryl, said group being optionally substituted with 1–4 groups selected from halo, $C_{1-4}$alkyl, $C_{1-4}$alkylS(O)$_x$—, with x as previously defined, $C_{1-4}$ alkylSO$_2$NH—, $H_2NSO_2$—, $C_{1-4}$alkylNHSO$_2$—, $(C_{1-4}alkyl)_2NSO_2$—, CN, OH, $OC_{1-4}$alkyl, and, said $C_{1-4}$alkyl and the $C_{1-4}$alkyl portions of said groups being optionally substituted with 1–5 halo and 1 group selected from OH and $OC_{1-3}$alkyl.

2. The compound of claim 1 wherein A and B represent a $C_{2-4}$ membered alkanediyl group such that a 3 to 5 membered ring is formed with the carbon atom to which they are attached, optionally substituted with 1–2 groups selected from halo, $C_{1-4}$alkyl, halo$C_{1-4}$alkyl, $C_{1-3}$alkoxy, $C_{1-3}$alkoxy$C_{1-3}$alkyl, $C_{1-3}$alkoxy$C_{1-3}$alkoxy and phenyl.

3. The compound of claim 2 wherein A and B represent a $C_{2-4}$ alkanediyl group such that a 3–5 membered ring is formed with the carbon atom to which they are attached, said ring being unsubstituted or substituted with 1–2 halo groups.

4. The compound of claim 3 wherein the 1–2 halo groups are fluoro groups.

5. The compound of claim 1 wherein two $R^1$ groups represent H and one $R^1$ is selected from the group consisting of: OH, halo, $C_{1-10}$alkyl, $C_{1-6}$alkoxy and $C_{6-10}$aryl, said $C_{1-10}$alkyl, $C_{6-10}$aryl and the alkyl portion of $C_{1-6}$alkoxy being optionally substituted with 1–3 halo, OH, $OC_{1-3}$alkyl, phenyl or naphthyl groups, said phenyl and naphthyl being optionally substituted with 1–3 substituents selected from: halo, $OCH_3$, $OCF_3$, $CH_3$, $CF_3$ and phenyl, wherein said phenyl is optionally substituted with 1–3 halo groups.

6. The compound of claim 1 wherein one $R^1$ group represents H and two $R^1$ groups are selected from the group consisting of: OH, halo, $C_{1-10}$alkyl and $C_{1-6}$alkoxy, said $C_{1-10}$alkyl and the alkyl portion of $C_{1-6}$alkoxy being optionally substituted with 1–3 halo groups.

7. The compound of claim 6 wherein two $R^1$ groups represent halo or methyl.

8. The compound of claim 1 wherein $R^2$ is selected from the group consisting of: (a) $C_{1-14}$alkyl optionally substituted with 1–6 halo groups and 1–3 substituents selected from OH, $OC_{1-3}$alkyl, and phenyl, said phenyl being optionally substituted with 1–4 groups independently selected from halo, $OCH_3$, $OCF_3$, $CH_3$ and $CF_3$, and said $C_{1-3}$alkyl portion of $OC_{1-3}$alkyl being optionally substituted with 1–3 halo groups; (b) phenyl or pyridyl optionally substituted with 1–3 halo, OH or $R^a$ groups; (c) $C_{2-10}$ alkenyl, optionally substituted with 1–3 substituents independently selected from halo, OH and $OC_{1-3}$alkyl, said $C_{1-3}$alkyl portion of $OC_{1-3}$alkyl being optionally substituted with 1–3 halo groups; (d) $CH_2CO_2H$; (e) $CH_2CO_2C_{1-6}$alkyl; (f) $CH_2C(O)NHR^a$ and (g) $NH_2$, $NHR^a$ and $N(R^a)_2$, and $R^a$ represents $C_{1-3}$alkyl, $OC_{1-3}$alkyl, $C_{6-10}$ar$C_{1-6}$alkylene or phenyl optionally substituted with 1–3 halo groups.

9. The compound of claim 1 wherein $R^2$ is $C_{1-14}$alkyl optionally substituted with 1–6 halo groups and 1–3 substituents selected from OH, $OC_{1-3}$alkyl and phenyl, said phenyl being optionally substituted with 1–4 groups independently selected from halo, $OCH_3$, $OCF_3$, $CH_3$ and $CF_3$, and the alkyl portion of $C_{1-3}$alkyl being optionally substituted with 1–3 halo groups.

10. The compound of claim 8 wherein R² represents methyl or cyclopropyl.

11. The compound of claim 1 wherein R³ is selected from the group consisting of: $C_{1-14}$alkyl, $C_{2-10}$alkenyl, $SC_{1-6}$alkyl, $C_{6-10}$aryl, heterocyclyl and heteroaryl, said alkyl, alkenyl, aryl, heterocyclyl, heteroaryl and the alkyl portion of $SC_{1-6}$alkyl being optionally substituted with (a) R; (b) 1–6 halo groups and (c) 1–3 groups selected from OH, $NH_2$, $NHC_{1-4}$alkyl, $N(C_{1-4}$alkyl$)_2$, $C_{1-4}$alkyl, $OC_{1-4}$alkyl, CN, $C_{1-4}$alkylS(O)$_x$— wherein x is 0, 1 or 2, $C_{1-4}$alkylSO$_2$NH—, $N_2NSO_2$—, $C_{1-4}$alkylNHSO$_2$— and $(C_{1-4}$alkyl$)_2NSO_2$—, said $C_{1-4}$alkyl and the $C_{1-4}$alkyl portions of said groups being optionally substituted with phenyl and 1–3 halo groups, and R is selected from heterocyclyl, heteroaryl and aryl, said group being optionally substituted with 1–4 groups selected from halo, $C_{1-4}$alkyl, $C_{1-4}$alkylS(O)$_x$—, with x as previously defined, $C_{1-4}$alkylSO$_2$NH—, $H_2NSO_2$—, $C_{1-4}$alkylNHSO$_2$—, $(C_{1-4}$alkyl$)_2NSO_2$—, CN, OH, $OC_{1-4}$alkyl, and, said $C_{1-4}$alkyl and the $C_{1-4}$alkyl portions of said groups being optionally substituted with 1–5 halo and 1 group selected from OH and $OC_{1-3}$ alkyl.

12. The compound of claim 11 wherein R³ is selected from the group consisting of: $C_{1-14}$alkyl, $C_{6-10}$aryl, heterocyclyl and heteroaryl, said groups being optionally substituted with (a) R; (b) 1–6 halo groups and (c) 1–3 groups selected from OH, $NH_2$, $NHC_{1-4}$alkyl, $N(C_{1-4}$alkyl$)_2$, $C_{1-4}$alkyl, $OC_{1-4}$alkyl, CN, $C_{1-4}$alkylS(O)$_x$— wherein x is 0, 1 or 2, $C_{1-4}$alkylSO$_2$NH—, $H_2NSO_2$—, $C_{1-4}$alkylNHSO$_2$—, $(C_{1-4}$alkyl$)_2NSO_2$—, said $C_{1-4}$alkyl and the $C_{1-4}$alkyl portions of said groups being optionally substituted with phenyl and 1–3 halo groups.

13. The compound of claim 11 wherein R³ is selected from the group consisting of: cyclopropyl optionally substituted with methyl or phenyl; phenyl optionally substituted with halo, OH, $OCH_3$ or $OCF_3$; heteroaryl selected from benzimidazolyl, indolyl, benzofuranyl, and dihydrobenzofuranyl, said heteroaryl groups being optionally substituted with: (a) R; (b) 1–6 halo groups or (c) 1–3 groups selected from OH, $NH_2$, $NHC_{1-4}$alkyl, $N(C_{1-4}$alkyl$)_2$, $C_{1-4}$alkyl, $OC_{1-4}$alkyl, CN, $C_{1-4}$alkylS(O)$_x$— wherein x is 0, 1 or 2, $C_{1-4}$alkylSO$_2$NH—, $H_2NSO_2$—, $C_{1-4}$alkylNHSO$_2$—, $(C_{1-4}$alkyl$)_2NSO_2$—, said $C_{1-4}$alkyl and the $C_{1-4}$alkyl portions of said groups being optionally substituted with phenyl and 1–3 halo groups, and R is selected from heterocyclyl, heteroaryl and aryl, said group being optionally substituted with 1–4 groups selected from halo, $C_{1-4}$alkyl, OH, $OC_{1-4}$alkyl, and, said $C_{1-4}$alkyl and the $C_{1-4}$alkyl portions of said groups being optionally substituted with 1–5 halo groups and 1 group selected from OH and $OC_{1-3}$alkyl.

14. The compound of claim 1 wherein R is selected from heterocyclyl, heteroaryl and aryl, said group being optionally substituted with 1–4 halo groups and 1–2 groups selected from $C_{1-4}$alkyl, $C_{1-4}$alkylS(O)$_x$—, wherein x is 0, 1 or 2, $C_{1-4}$alkylSO$_2$NH—, $H_2NSO_2$—, $C_{1-4}$alkylNHSO$_2$—, $(C_{1-4}$ alkyl$)_2NSO_2$—, CN, OH and $OC_{1-4}$alkyl, said $C_{1-4}$alkyl and the $C_{1-4}$alkyl portions of said groups being optionally substituted with 1–3 halo groups and 1 group selected from OH and $OC_{1-3}$alkyl.

15. A compound selected from the group consisting of:

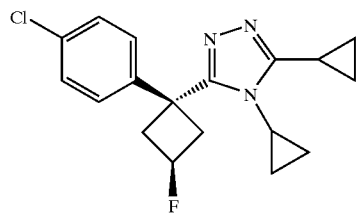

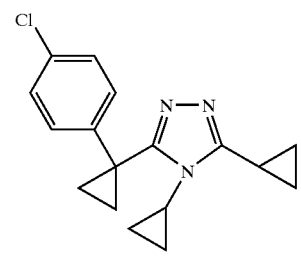

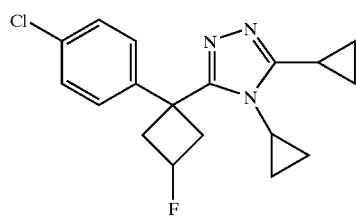

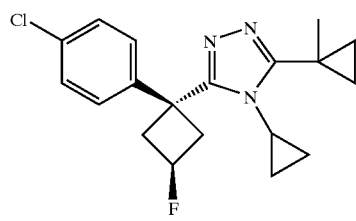

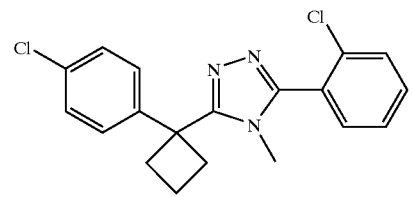

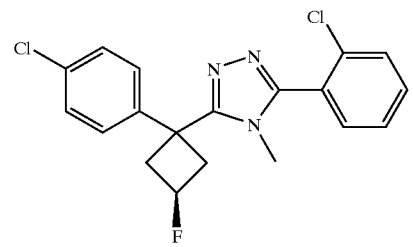

-continued

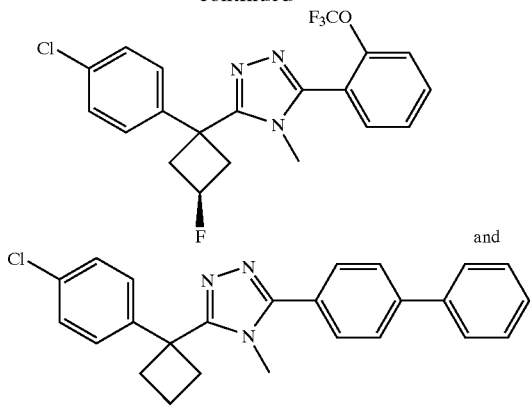

or a pharmaceutically acceptable salt or solvate thereof.

16. The compound of claim 15 of the structural formula:

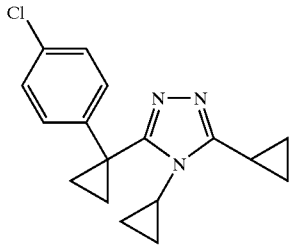

or a pharmaceutically acceptable salt or solvate thereof.

17. The compound of claim 15 of the structural formula:

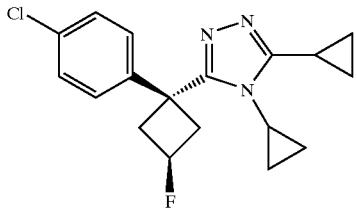

or a pharmaceutically acceptable salt or solvate thereof.

18. The compound of claim 15 of the structural formula:

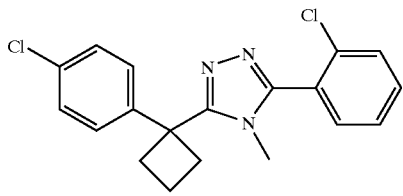

or a pharmaceutically acceptable salt or solvate thereof.

19. The compound of claim 15 of the structural formula:

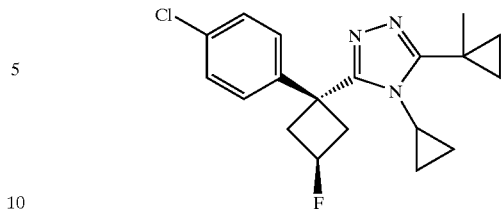

or a pharmaceutically acceptable salt or solvate thereof.

20. A pharmaceutical composition comprising a compound in accordance with claim 1 in combination with a pharmaceutically acceptable carrier.

21. A method of treating hyperglycemia, diabetes or insulin resistance in a mammalian patient in need of such treatment which comprises administering to said patient an effective amount of a compound in accordance with claim 1.

22. A method of treating non-insulin dependent diabetes mellitus in a mammalian patient in need of such treatment comprising administering to the patient an anti-diabetic effective amount of a compound in accordance with claim 1.

23. A method of treating obesity in a mammalian patient in need of such treatment compriseing administering to said patient a compound in accordance with claim 1 in an amount that is effective to treat obesity.

24. A method of treating Syndrome X in a mammalian patient in need of such treatment, comprising administering to said patient a compound in accordance with claim 1 in an amount that is effective to treat Syndrome X.

25. A method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound in accordance with claim 1 in an amount that is effective to treat said lipid disorder.

26. A method of treating atherosclerosis in a mammalian patient in need of such treatment, comprising administering to said patient a compound in accordance with claim 1 in an amount effective to treat atherosclerosis.

27. A method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with claim 1 in an amount that is effective to treat said condition.

28. A method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with claim 1 in an amount that is effective to delay the onset of said condition.

29. A method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with claim 1 in an amount that is effective to reduce the risk of developing said condition.

30. A method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient an effective amount of a compound as defined in claim 1, and a compound selected from the group consisting of:
  (a) DP-IV inhibitors;
  (b) insulin sensitizers selected from the group consisting of (i) PPAR agonists and (ii) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 mimetics, and GLP-1 receptor agonists;
  (h) GIP, GIP mimetics, and GIP receptor agonists;
  (i) PACAP, PACAP mimetics, and PACAP receptor 3 agonists;
  (j) cholesterol lowering agents selected from the group consisting of
    (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
  (k) PPAR δ agonists;
  (l) antiobesity compounds;
  (m) ileal bile acid transporter inhibitors;
  (n) anti-inflammatory agents excluding glucocorticoids; and
  (o) protein tyrosine phosphatase-1B (PTP-1B) inhibitors,
said compounds being administered to the patient in an amount that is effective to treat said condition.

31. A method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a therapeutically effective amount of a compound as defined in claim 1 and an HMG-CoA reductase inhibitor.

32. The method of claim 31 wherein the EMG-CoA reductase inhibitor is a statin.

33. The method of claim 32 wherein the statin is selected from the group consisting of lovastatin, simvastatin, pravastatin, fluvastatin, atorvastatin, itavastatin, ZD-4522 and rivastatin.

34. A method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound as defined in claim 1 and an HMG-CoA reductase inhibitor.

35. A method for delaying the onset or reducing the risk of developing atherosclerosis in a human patient in need of such treatment comprising administering to said patient an effective amount of a compound as defined in claim 1, and an HMG-CoA reductase inhibitor.

36. The method of claim 34 wherein the HMG-CoA reductase inhibitor is a statin.

37. The method of claim 36 wherein the statin is selected from the group consisting of lovastatin, simvastatin, pravastatin, fluvastatin, atorvastatin, itavastatin, ZD-4522 and rivastatin.

38. The method of claim 37 wherein the statin is simvastatin.

39. The method of claim 38 further comprising administering a cholesterol absorption inhibitor.

40. The method of claim 39 wherein the cholesterol absorption inhibitor is ezetimibe.

41. A pharmaceutical composition comprising
  (1) a compound according to claim 1,
  (2) a compound selected from the group consisting of:
    (a) DP-IV inhibitors:
    (b) insulin sensitizers selected from the group consisting of (i) PPAR agonists and (ii) biguanides;
    (c) insulin and insulin mimetics;
    (d) sulfonylureas and other insulin secretagogues;
    (e) α-glucosidase inhibitors;
    (f) glucagon receptor antagonists;
    (g) GLP-1, GLP-1 mimetics, and GLP-1 receptor agonists;
    (h) GIP, GIP mimetics, and GIP receptor agonists;
    (i) PACAP, PACAP mimetics, and PACAP receptor 3 agonists;
    (j) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
    (k) PPAR δ agonists;
    (l) antiobesity compounds;
    (m) ileal bile acid transporter inhibitors;
    (n) anti-inflammatory agents other than glucocorticoids; and
    (o) protein tyrosine phosphatase-1B (PTP-1B) inhibitors; and
  (3) a pharmaceutically acceptable carrier.

42. The compound of claim 1 selected from the group consisting of:
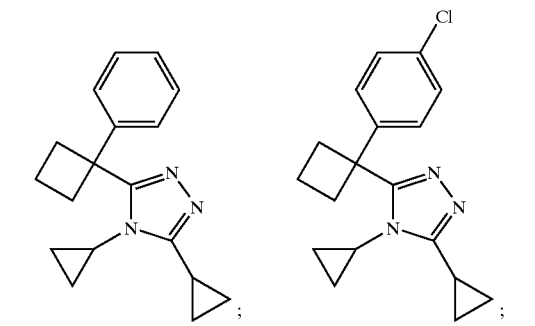
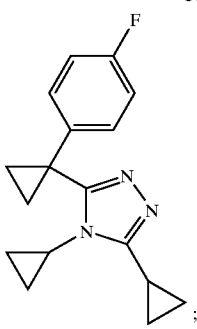
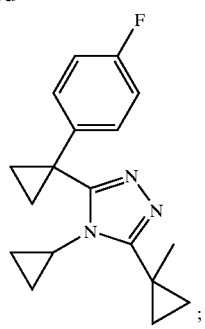
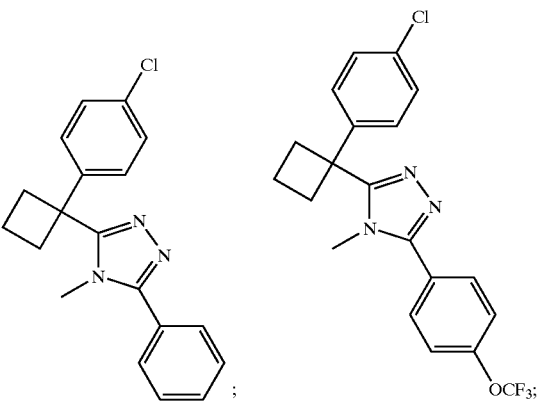
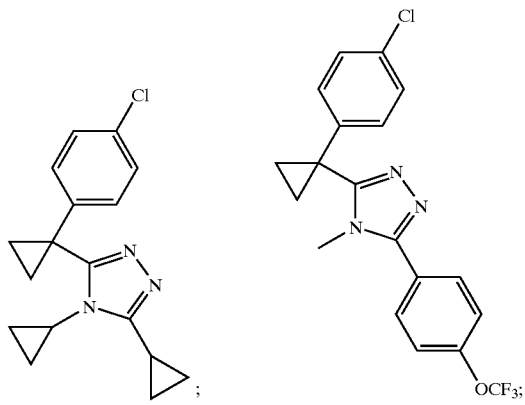
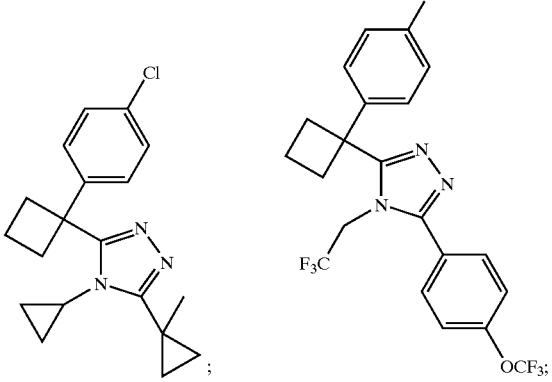
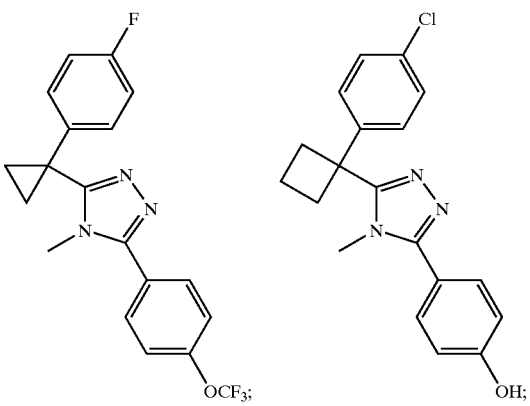
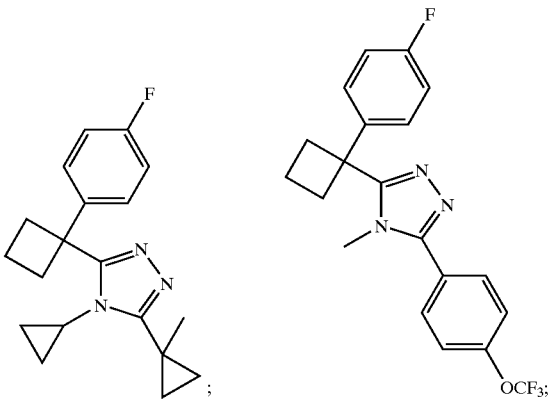
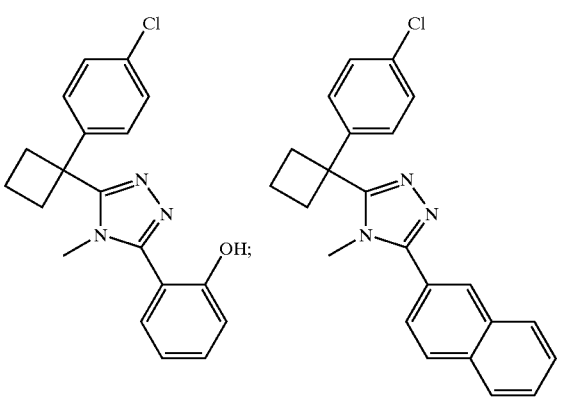

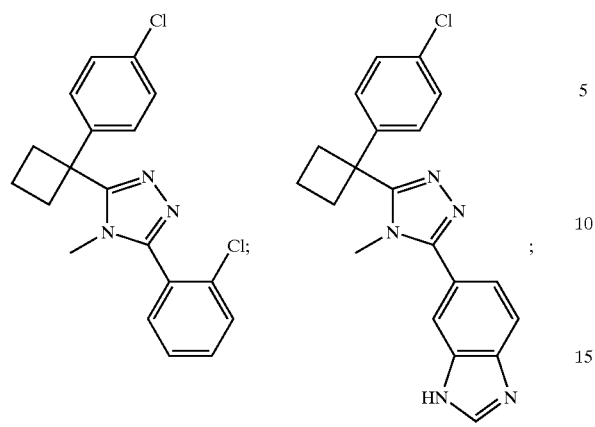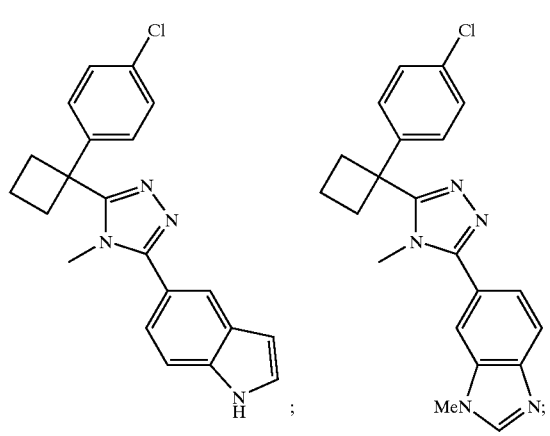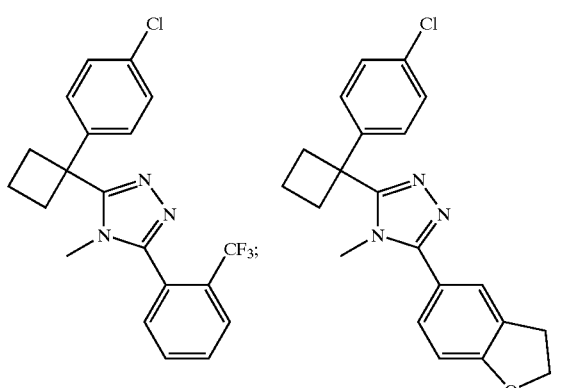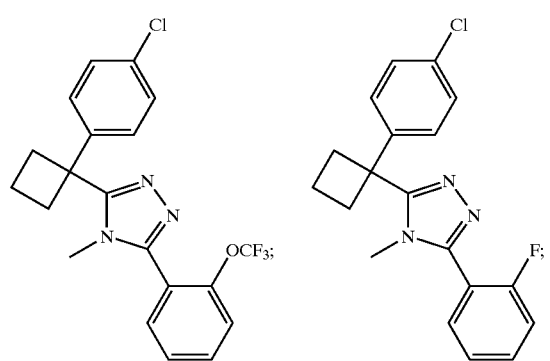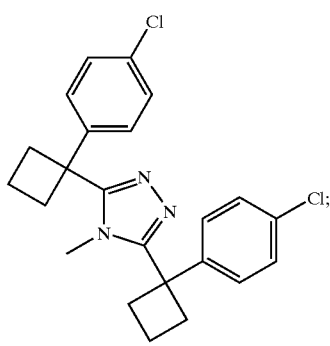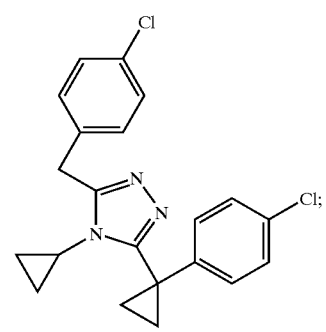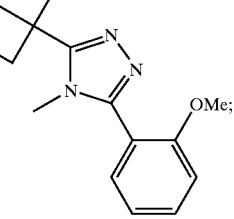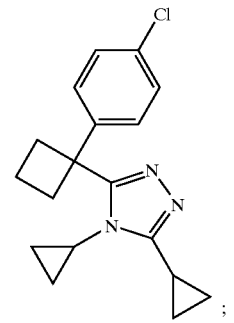

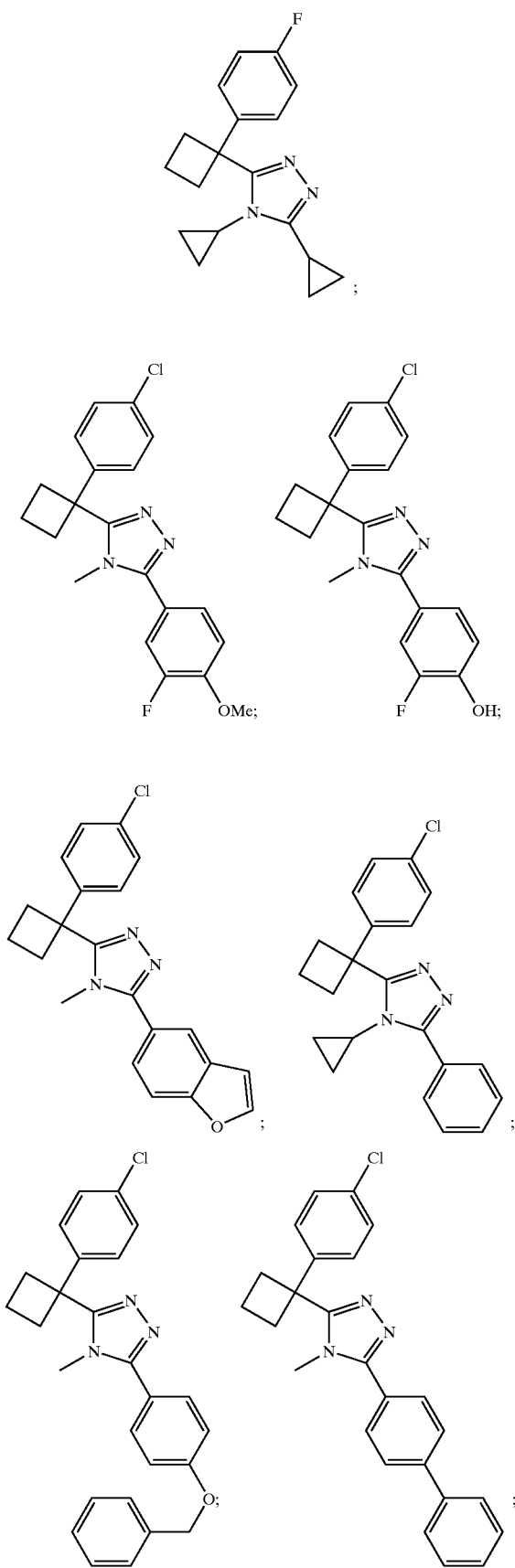
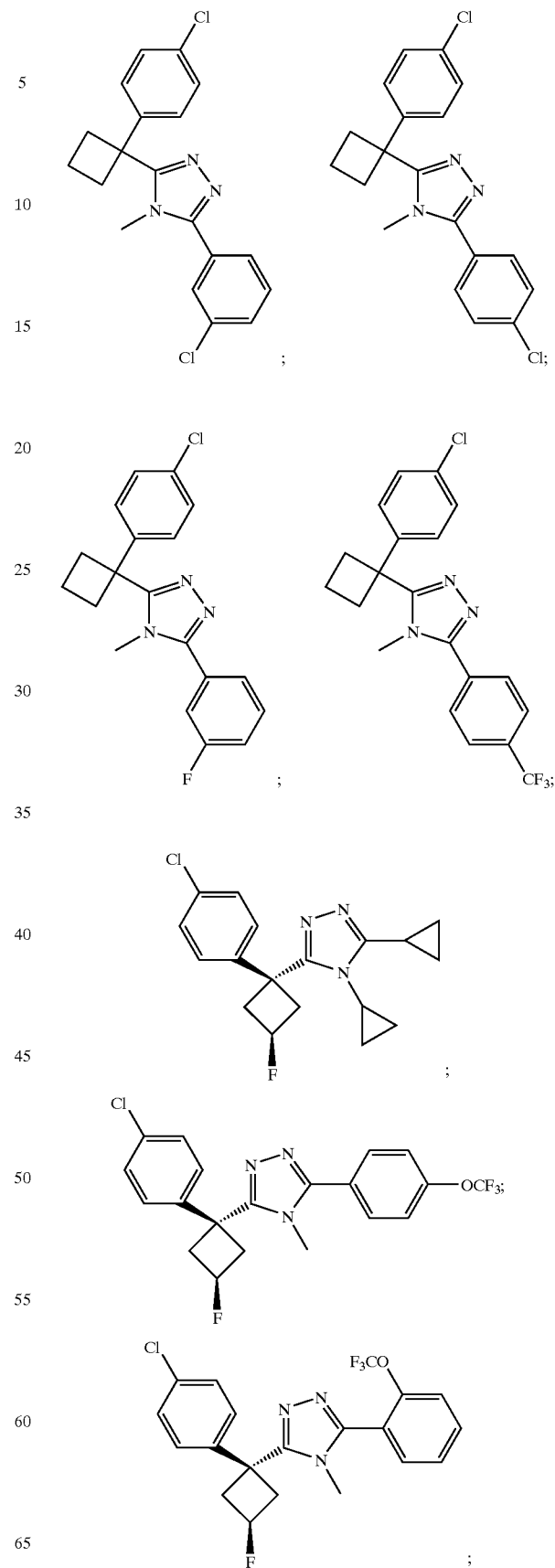

-continued
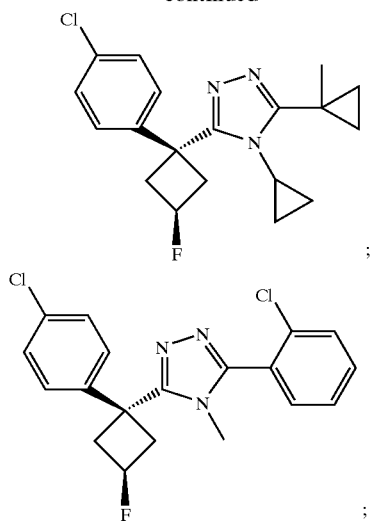
;
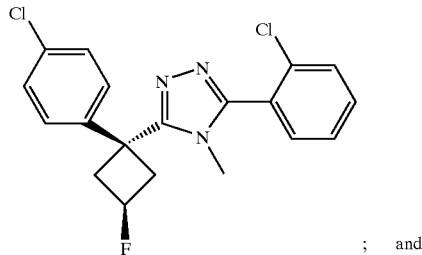
; and
-continued
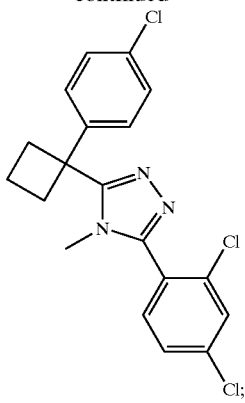
or a pharmaceutically acceptable salt or solvate thereof.
* * * * *